US010669539B2

(12) United States Patent
Yates et al.

(10) Patent No.: US 10,669,539 B2
(45) Date of Patent: Jun. 2, 2020

(54) METHODS AND COMPOSITIONS FOR GENERATING CRISPR GUIDE RNA LIBRARIES

(71) Applicant: Brigham Young University, Provo, UT (US)

(72) Inventors: Joshua Yates, Spanish Fork, UT (US); Jonathon Hill, Provo, UT (US)

(73) Assignee: Pioneer Biolabs, LLC, Provo, UT (US)

( * ) Notice: Subject to any disclaimer, the term of this patent is extended or adjusted under 35 U.S.C. 154(b) by 0 days.

(21) Appl. No.: 15/727,279

(22) Filed: Oct. 6, 2017

(65) Prior Publication Data

US 2018/0100147 A1  Apr. 12, 2018

Related U.S. Application Data

(60) Provisional application No. 62/405,070, filed on Oct. 6, 2016.

(51) Int. Cl.
| | | |
|---|---|---|
| *C12N 15/11* | (2006.01) | |
| *C12N 15/10* | (2006.01) | |
| *C12N 15/113* | (2010.01) | |

(52) U.S. Cl.
CPC .......... *C12N 15/11* (2013.01); *C12N 15/1082* (2013.01); *C12N 15/113* (2013.01); *C12N 2310/20* (2017.05); *C12N 2310/531* (2013.01); *C12N 2330/31* (2013.01)

(58) Field of Classification Search
None
See application file for complete search history.

(56) References Cited

U.S. PATENT DOCUMENTS

| | | | |
|---|---|---|---|
| 5,766,891 | A | 6/1998 | Shuman |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 9,725,717 | B2 | 8/2017 | Collard et al. |
| 2014/0068797 | A1 | 3/2014 | Doudna et al. |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0242702 | A1 | 8/2014 | Chen et al. |
| 2014/0248702 | A1 | 9/2014 | Zhang et al. |
| 2014/0256046 | A1 | 9/2014 | Zhang et al. |
| 2014/0273037 | A1 | 9/2014 | Wu |
| 2014/0273226 | A1 | 9/2014 | Wu |
| 2014/0273230 | A1 | 9/2014 | Chen et al. |
| 2014/0273231 | A1 | 9/2014 | Zhang et al. |
| 2014/0273232 | A1 | 9/2014 | Zhang et al. |
| 2014/0273233 | A1 | 9/2014 | Chen et al. |
| 2014/0273234 | A1 | 9/2014 | Zhang et al. |
| 2014/0273235 | A1 | 9/2014 | Voytas et al. |
| 2014/0287938 | A1 | 9/2014 | Zhang et al. |
| 2014/0295556 | A1 | 10/2014 | Joung et al. |
| 2014/0295557 | A1 | 10/2014 | Joung et al. |
| 2014/0298547 | A1 | 10/2014 | Sastry-Dent et al. |
| 2014/0304853 | A1 | 10/2014 | Ainley et al. |
| 2014/0309487 | A1 | 10/2014 | Lee et al. |
| 2014/0310828 | A1 | 10/2014 | Lee et al. |
| 2014/0310830 | A1 | 10/2014 | Zhang et al. |
| 2014/0315985 | A1 | 10/2014 | May et al. |
| 2014/0335063 | A1 | 11/2014 | Cannon et al. |
| 2014/0335620 | A1 | 11/2014 | Zhang et al. |
| 2014/0342456 | A1 | 11/2014 | Mali et al. |
| 2014/0342457 | A1 | 11/2014 | Mali et al. |
| 2014/0342458 | A1 | 11/2014 | Mali et al. |
| 2014/0349400 | A1 | 11/2014 | Jakimo et al. |
| 2014/0349405 | A1 | 11/2014 | Sontheimer et al. |
| 2014/0356867 | A1 | 12/2014 | Peter et al. |
| 2014/0356956 | A1 | 12/2014 | Church et al. |
| 2014/0356958 | A1 | 12/2014 | Mali et al. |
| 2014/0356959 | A1 | 12/2014 | Church et al. |
| 2014/0357523 | A1 | 12/2014 | Zeiner et al. |
| 2014/0357530 | A1 | 12/2014 | Zhang et al. |
| 2014/0364333 | A1 | 12/2014 | Wu et al. |
| 2014/0377868 | A1 | 12/2014 | Joung et al. |
| 2016/0046961 | A1 | 2/2016 | Jinek et al. |
| 2016/0060653 | A1 | 3/2016 | Doudna et al. |
| 2016/0060654 | A1 | 3/2016 | Doudna et al. |
| 2016/0068864 | A1 | 3/2016 | Doudna et al. |
| 2016/0130608 | A1 | 5/2016 | Doudna et al. |

(Continued)

FOREIGN PATENT DOCUMENTS

| | | |
|---|---|---|
| WO | WO2015065964 A1 | 5/2015 |
| WO | WO2015100929 A1 | 7/2015 |
| WO | WO2016196805 A1 | 12/2016 |

OTHER PUBLICATIONS

Svitashev et al., "Targeted Mutagenesis, Precise Gene Editing, and Site-Specific Gene Insertion in Maize Using Cas9 and Guide RNA" 169 Plant Physiology 931-945 (Aug. 12, 2015).*

(Continued)

*Primary Examiner* — Nancy J Leith

(57) ABSTRACT

The disclosure generally relates to compositions, polynucleotides, kits, methods, and systems for generating clustered regularly interspaced short palindromic repeats (CRISPR) libraries. Disclosed are polynucleotides encoding for a constant region of a CRISPR single guide RNA (sgRNA) or CRISPR targeting RNA (crRNA) having a non-palindromic recognition site for a type II restriction enzyme oriented in a manner recognized by the type II restriction enzyme for cutting a site past an end of the polynucleotide. The methods include using the polynucleotide to prepare CRISPR libraries.

16 Claims, 8 Drawing Sheets

Specification includes a Sequence Listing.

(56) References Cited

U.S. PATENT DOCUMENTS

| | | |
|---|---|---|
| 2016/0130609 A1 | 5/2016 | Doudna et al. |
| 2016/0138008 A1 | 5/2016 | Doudna et al. |
| 2016/0289675 A1* | 10/2016 | Ryan .................. C12N 15/907 |
| 2017/0051312 A1 | 2/2017 | Jinek et al. |
| 2017/0166893 A1 | 6/2017 | Doudna et al. |

OTHER PUBLICATIONS

Zhu, "Overview of guide RNA design tools for CRISPR-Cas9 genome editing technology" 10(4) Frontiers in Biology 289-296 (Aug. 16, 2015).*

Doench et al.: "Rational design of highly active sgRNAs for CRISPR-Cas9-mediated gene inactivation", Nature Biotechnology, vol. 32, Sep. 3, 2014 (Sep. 3, 2014), pp. 1262-1267, XP055294825, DOI: doi:10.1038/nbt.3026.

Nishimasu, Hiroshi, et al. "Crystal structure of Cas9 in complex with guide RNA and target DNA." Cell 156.5 (2014): 935-949.

Zhang, Jian-Ping, et al. "Different effects of sgRNA length on CRISPR-mediated gene knockout efficiency." Scientific reports 6 (2016): 1-10.

Burstein, David, et al. "New CRISPR-Cas systems from uncultivated microbes." Nature 542.7640 (2017): 237-241.

Zetsche, Bernd, et al. "Cpf1 is a single RNA-guided endonuclease of a class 2 CRISPR-Cas system." Cell 163.3 (2015): 759-771.

Morgan, Richard D., et al. "The MmeI family: type II restriction-modification enzymes that employ single-strand modification for host protection." Nucleic acids research 37.15 (2009): 5208-5221.

Jiang et al.: "Demonstration of CRISPR/Cas9/sgRNA-mediated targeted gene modification in *Arabidopsis*, tobacco, sorghum and rice", Nucleic Acids Research, vol. 41, No. 20, Sep. 2, 2013 (Sep. 2, 2013), pp. 1-12.

* cited by examiner

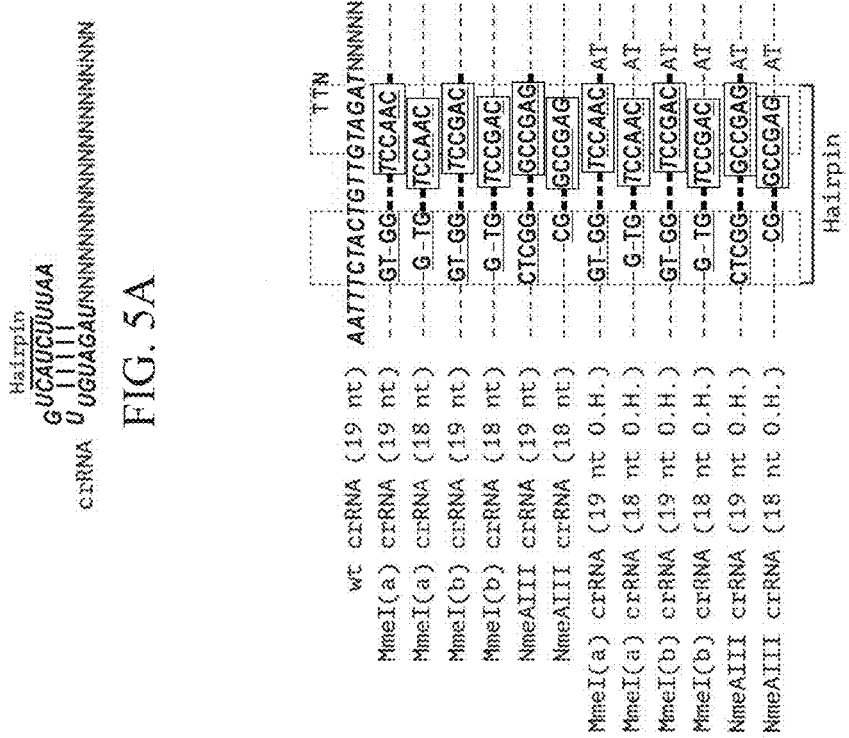
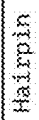
FIG. 5A
FIG. 5B

METHODS AND COMPOSITIONS FOR GENERATING CRISPR GUIDE RNA LIBRARIES

CROSS-REFERENCE TO RELATED APPLICATIONS

This application claims the benefit of U.S. provisional application Ser. No. 62/405,070 filed 6 Oct. 2016, the disclosure of which is hereby incorporated in its entirety by reference herein.

SEQUENCE LISTING

The text file Sequences_001_ST25.txt of size 94.5 KB created 6 Oct. 2017, filed herewith, is incorporated in its entirety by reference herein.

TECHNICAL FIELD

The disclosure generally relates to compositions, polynucleotides, kits, methods, and systems for generating clustered regularly interspaced short palindromic repeats (CRISPR) libraries.

BACKGROUND

CRISPR-Cas9 technology has greatly improved our ability to target and mutate specific DNA sequences, revolutionizing mutagenesis in many model organisms. There has been recent interest in creating CRISPR guide RNA (gRNA) libraries containing complex mixtures of gRNAs targeting large sets of genes, including comprehensive sets targeting the entire genome. However, because each targeting region must be individually synthesized, these libraries are very expensive to generate. Therefore, the development of rapid, inexpensive methods for creating CRISPR gRNA libraries is desirable. In order to address the costs associated with library development, PCT Patent Application Publication No. WO 2016/196805, which is incorporated in its entirety by reference herein, discloses methods for enzymatically generating CRISPR gRNA libraries. The disclosed methods involve restriction digest of a double stranded DNA starting set created from genomic DNA, PCR products, or RNA and followed by a complex set of adapter ligations and removals with extensive wash steps in between. The complete protocol as disclosed contains over 20 steps, requires several expensive kits and enzymes, and takes at least three days to complete (or approximately twelve hours plus a required overnight incubation). Due to the complex nature of the protocol, it is also hindered by low yields and frequent failures.

SUMMARY

The present invention as disclosed in various embodiments addresses and overcomes the limitations of the current state of the art. The disclosure generally relates to compositions, polynucleotides, kits, methods, and systems for generating clustered regularly interspaced short palindromic repeats (CRISPR) libraries.

In various embodiments are disclosed polynucleotide or polynucleotides encoding for a constant region of a CRISPR single guide RNA (sgRNA) or CRISPR targeting RNA (crRNA) comprising a non-palindromic recognition site for a type II restriction enzyme/restriction endonuclease, the non-palindromic recognition site being oriented in a manner recognized by the type II restriction enzyme for cutting a site that is 17 to 27 base pairs past an end of the polynucleotide. In various embodiments, the polynucleotides encode for a plurality of sgRNAs or crRNAs.

The polynucleotide of various embodiments is double-stranded with sense and antisense strands and the non-palindromic recognition site is oriented in a manner recognized by the type II restriction enzyme for cutting a site that is 17 to 27 base pairs upstream from a 5' end of the sense strand or downstream from a 3' end of the antisense strand. In other embodiments, the polynucleotide is double-stranded with sense and antisense strands and the non-palindromic recognition site is oriented in a manner recognized by the type II restriction enzyme for cutting a site that is 17 to 27 base pairs downstream from a 3' end of the sense strand or upstream from a 5' end of the anti sense strand.

In various embodiments, the polynucleotide(s) further include(s) a modification selected from at least one modified sugar moiety, at least one modified internucleotide linkage, at least one modified nucleotide, or combinations thereof. The modification of various embodiments can be located at or adjacent to the end of the polynucleotide. In various embodiments, the internucleotide linkage is selected from the group including phosphorothioate, alkylphosphonate, phosphorodithioate, alkylphosphonothioate, phosphoramidate, carbamate, carbonate, phosphate triester, acetamidate, carboxymethyl ester, or combinations thereof. In various embodiments, the modified nucleotide is selected from a peptide nucleic acid, a locked nucleic acid (LNA), or combinations thereof. In various embodiments, the modified sugar moiety is selected from: a 2'-O-methoxyethyl modified sugar moiety, a 2'-methoxy modified sugar moiety, a 2'-O-alkyl modified sugar moiety, a bicyclic sugar moiety, or combinations thereof.

In various embodiments, the polynucleotide(s) is/are attached, affixed, or immobilized on a support such as a solid support. The support of various embodiments can include two-dimensional surfaces such as microarray slides or three-dimensional surfaces such as beads or micro-spheres including polystyrene micro-spheres, magnetic microspheres, silica micro-spheres, or fluorescent micro-spheres.

In various embodiments, the non-palindromic recognition site when transcribed is capable of being incorporated within a stem-loop structure of the CRISPR sgRNA or CRISPR crRNA. In various embodiments, the polynucleotide also includes a second site that has a sequence substantially complimentary to the sequence of the non-palindromic recognition site. The second site of various embodiments is capable of being incorporated within a stem-loop structure of the CRISPR sgRNA, CRISPR trans-activating crRNA (tracrRNA), or CRISPR crRNA. In various embodiments, the non-palindromic recognition site and second site when transcribed bond together to form a stem-loop structure of the CRISPR sgRNA or CRISPR crRNA.

In various embodiments, the type II restriction enzyme is a type IIS restriction enzyme. The type IIS restriction enzyme of various embodiments can include, for example, NmeAIII, MmeI, CstMI, EcoP15I, ApyPI, AquII, AquIII, AquIV, CdpI, CstMI, DraRI, DrdIV, EsaSSI, MaqI, NhaXI, NlaCI, PlaDI, PspOMII, PspPRI, RceI, RpaB5I, SdeAI, SpoDI, BsbI, or combinations thereof.

In various embodiments, the non-palindromic recognition site is positioned at any position within the polynucleotide and oriented in a manner recognized by the type II restriction enzyme for cutting a site that is 17 to 27 base pairs past an end of the polynucleotide. In different embodiments, the non-palindromic recognition site starts or ends at a position 0, 1, 2, or 3 base pairs from an end of the polynucleotide.

In various embodiments are disclosed a polynucleotide or polynucleotides encoding for CRISPR sgRNA or CRISPR crRNA including a first polynucleotide, the first polynucleotide encoding for a constant region of a CRISPR sgRNA or CRISPR crRNA and having a non-palindromic recognition site for a type II restriction enzyme being oriented in a manner recognized by the type II restriction enzyme for cutting a site that is 17 to 27 base pairs past an end of the polynucleotide, and a second polynucleotide linked to the end of the first polynucleotide, wherein the second polynucleotide encodes for a variable region of the CRISPR sgRNA or CRISPR crRNA and includes the site 17 to 27 base pairs past the end of the first polynucleotide.

In various embodiments are disclosed expression cassettes, plasmids, vectors, or expression vectors including the polynucleotide encoding for the CRISPR sgRNA or CRISPR crRNA of various embodiments and a promoter polynucleotide operably linked to the polynucleotide of various embodiments, wherein the promoter polynucleotide is recognized by an RNA polymerase and is capable of directing the RNA polymerase to transcribe the CRISPR sgRNA or CRISPR crRNA from the polynucleotide of various embodiments.

In various embodiments are disclosed kits for generating CRISPR guide RNA (gRNA) libraries comprising a polynucleotide or polynucleotides encoding for a constant region(s) of a CRISPR sgRNA or CRISPR crRNA and having a non-palindromic recognition site for a type II restriction enzyme, wherein the non-palindromic recognition site is oriented in a manner recognized by the type II restriction enzyme for cutting a site that is 17 to 27 base pairs past an end of the polynucleotide. The kit of various embodiments can further include the type II restriction enzyme or enzymes; supports such as a solid support, wherein polynucleotides are capable of being immobilized on at least one of the supports or are immobilized on the at least one of the supports; a promoter polynucleotide recognized by a RNA polymerase; or combinations thereof.

In various embodiments are disclosed methods and systems of generating CRISPR gRNA libraries, the methods and systems including the steps of: providing a first polynucleotide encoding for a constant region of a CRISPR sgRNA or CRISPR crRNA and having a non-palindromic recognition site for a type II restriction enzyme, wherein the non-palindromic recognition site is oriented in a manner recognized by the type II restriction enzyme to cut a site that is 17 to 27 base pairs past an end of the first polynucleotide; ligating DNA to the end of the first polynucleotide to form a second polynucleotide; and digesting the second polynucleotide with the type II restriction enzyme to form a third polynucleotide encoding a CRISPR sgRNA or CRISPR crRNA, wherein the type II restriction enzyme cuts the DNA at a site that is 17 to 27 base pairs from the end of the first polynucleotide. The methods/systems of various embodiments can include the first polynucleotide being a plurality of first polynucleotides; at least a portion of the plurality of first polynucleotides being ligated with DNA to form a plurality of second polynucleotides; and the plurality of second polynucleotides being digested with the type II restriction enzyme to form a plurality of third polynucleotides encoding a plurality of sgRNAs, where at least one of the plurality of sgRNAs has a targeting sequence different from the other sgRNAs. In various embodiments, the DNA prior to the ligation step is digested with a nuclease.

In various embodiments, the methods/systems further include the step of ligating a promoter polynucleotide recognized by a RNA polymerase to an end of the third polynucleotide, wherein the promoter polynucleotide when ligated to the third polynucleotide is capable of directing the RNA polymerase to transcribe the sgRNA from the third polynucleotide.

BRIEF DESCRIPTION OF THE DRAWINGS

For a further understanding of the nature, objects, and advantages of the present invention, reference should be had to the following detailed description, read in conjunction with the following drawings, wherein:

FIG. 5A shows the hairpin structure of a wildtype cRNA for CRISPR Cpf1 (SEQ ID NO: 440).

FIG. 5B shows polynucleotides of various embodiments encoding for an sgRNA or crRNA recognized by a CRIPSR Cpf1 protein and having non-palindromic recognition site for MmeI and NmeAIII *F. novicida* crRNA sequence was modified to insert an MmeI binding site while maintaining secondary structure. WT crRNA indicates the previously published CRISPR sgRNA sequence for Cpf1 binding. Areas surrounded by dotted lines indicate the hairpin region. Cpf1-based systems lack a tracrRNA. MmeI and NmeAIII binding sites are shown surrounded by a solid line. Underlined letters indicate bases that do not match the original sequence. O.H. indicates the presence of an overhang added to the crRNA. SEQ ID NOS: 441 to 453 are shown in descending order.

DETAILED DESCRIPTION

Figure 1:
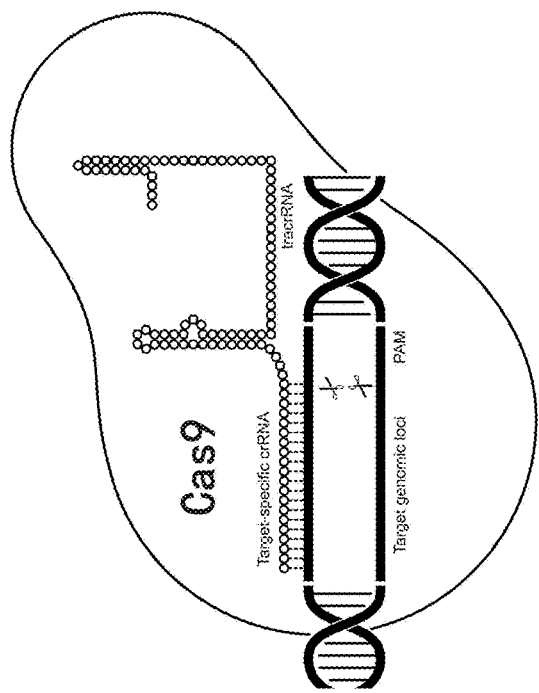
FIG. 1 shows an example of a CRISPR Cas9 protein forming a complex with a guide RNA.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Except in the examples, or where otherwise expressly indicated, all numerical quantities in this description indicating amounts of material or conditions of reaction or use are to be understood as modified by the word "about" in describing the broadest scope of the invention. Practice within the numerical limits stated is generally preferred. The first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

Unless indicated otherwise, all technical and scientific terms used herein have the same meaning as commonly understood by one of ordinary skill in the art to which this invention belongs.

Throughout this application, where publications are referenced, the disclosures of these publications in their entireties are hereby incorporated by reference into this application to more fully describe the state of the art to which this invention pertains.

It is also to be understood that this invention is not limited to the specific embodiments and methods described below, as specific components or conditions may, of course, vary. Furthermore, the terminology used herein is used only for the purpose of describing particular embodiments of the present invention and is not intended to be limiting in any way It must also be noted that, as used in the specification and the appended claims, the singular form "a," "an," and "the" comprise plural referents unless the context clearly indicates otherwise. For example, reference to a component in the singular is intended to comprise a plurality of components.

The term "or" is understood to mean "and/or".

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

The terms "polynucleotide", "nucleotide", "nucleotide sequence", "nucleic acid" and "oligonucleotide" are used interchangeably in this disclosure. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "exogenous" nucleic acid can refer to a nucleic acid that is not normally or naturally found in or produced by a given bacterium, organism, or cell in nature. The term "endogenous" nucleic acid can refer to a nucleic acid that is normally found in or produced by a given bacterium, organism, or cell in nature.

The term "recombinant" is understood to mean that a particular nucleic acid (DNA or RNA) or protein is the product of various combinations of cloning, restriction, or ligation steps resulting in a construct having a structural coding or non-coding sequence distinguishable from endogenous nucleic acids found in natural systems.

The terms "construct", "cassette", "expression cassette", "plasmid", "vector", or "expression vector" is understood to mean a recombinant nucleic acid, generally recombinant DNA, which has been generated for the purpose of the expression or propagation of a nucleotide sequence(s) of interest, or is to be used in the construction of other recombinant nucleotide sequences.

The term "promoter" or "promoter polynucleotide" is understood to mean a regulatory sequence/element or control sequence/element that is capable of binding/recruiting a RNA polymerase and initiating transcription of sequence downstream or in a 3' direction from the promoter. A promoter can be, for example, constitutively active or always on or inducible in which the promoter is active or inactive in the presence of an external stimulus. Example of promoters include T7 promoters or U6 promoters.

The term "operably linked" can mean the positioning of components in a relationship which permits them to function in their intended manner. For example, a promoter can be linked to a polynucleotide sequence to induce transcription of the polynucleotide sequence.

The terms "sequence identity" or "identity" refers to a specified percentage of residues in two nucleic acid or amino acid sequences that are identical when aligned for maximum correspondence over a specified comparison window, as measured by sequence comparison algorithms or by visual inspection. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity.

The term "comparison window" refers to a segment of at least about 20 contiguous positions in which a sequence may be compared to a reference sequence of the same number of contiguous positions after the two sequences are aligned optimally. In a refinement, the comparison window is from 15 to 30 contiguous positions in which a sequence may be compared to a reference sequence of the same number of contiguous positions after the two sequences are aligned optimally. In another refinement, the comparison window is usually from about 50 to about 200 contiguous positions in which a sequence may be compared to a reference sequence of the same number of contiguous positions after the two sequences are aligned optimally.

The terms "complementarity" or "complement" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 4, 5, and 6 out of 6 being 66.67%, 83.33%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 40%, 50%, 60%, 62.5%, 70%, 75%, 80%, 85%, 90%, 95%, 97%, 98%, 99%, or 100%, or percentages in between over a region of 4, 5, 6, 7, and 8 nucleotides, or refers to two nucleic acids that hybridize under stringent conditions.

Other references that are all incorporated in its entirety by reference herein include the following patents, patent application publications, and publications: U.S. Pat. Nos. 8,906,616; 8,895,308; 8,889,418; 8,889,356; 8,871,445; 8,865,406; 8,795,965; 8,771,945; 8,697,359; 9,725,717; U.S. Patent Application Publication No. 2014/0068797; 2014/0170753; 2014/0179006; 2014/0179770; 2014/0186843; 2014/0186919; 2014/0186958; 2014/0189896; 2014/0227787; 2014/0234972; 2014/0242664; 2014/0242699; 2014/0242700; 2014/0242702; 2014/0248702; 2014/0256046; 2014/0273037; 2014/0273226; 2014/0273230; 2014/0273231; 2014/0273232; 2014/0273233; 2014/0273234; 2014/0273235; 2014/0287938; 2014/0295556; 2014/0295557; 2014/0298547; 2014/0304853; 2014/0309487; 2014/0310828; 2014/0310830; 2014/0315985; 2014/0335063; 2014/0335620; 2014/0342456; 2014/0342457; 2014/0342458; 2014/0349400; 2014/0349405; 2014/0356867; 2014/0356956; 2014/0356958; 2014/0356959; 2014/0357523; 2014/0357530; 2014/0364333; 2014/0377868; 2017/0166893; 2014/0068797; 2016/0060654; 2016/0046961; 2016/0060653; 2016/0068864; 2016/0130609; 2016/0130608; 2016/0138008; 2017/0051312; PCT Application Publication No. WO 2016/196805; WO 2015/100929; WO 2015/065964;

DOENCH ET AL.: "Rational design of highly active sgRNAs for CRISPR-Cas9-mediated gene inactivation", NATURE BIOTECHNOLOGY, vol. 32, 3 Sep. 2014 (2014 Sep. 3), pages 1262-1267, XP055294825, DOI: doi:10.1038/nbt.3026;

DOENCH ET AL.: "Rational design of highly active sgRNAs for CRISPR-Cas9-mediated gene inactivation", NATURE BIOTECHNOLOGY, vol. 32, 3 Sep. 2014 (2014 Sep. 3), pages 1262-1267, XP055294825, DOI: doi:10.1038/nbt.3026;

DOENCH ET AL.: "Rational design of highly active sgRNAs for CRISPR-Cas9-mediated gene inactivation", Nat Biotechnol. 2014 December; 32(12): 1262-1267. Published online 2014 Sep. 3. doi: 10.1038/nbt.3026;

Nishimasu, Hiroshi, et al. "Crystal structure of Cas9 in complex with guide RNA and target DNA." Cell 156.5 (2014): 935-949;

Zhang, Jian-Ping, et al. "Different effects of sgRNA length on CRISPR-mediated gene knockout efficiency." Scientific reports 6 (2016);

Burstein, David, et al. "New CRISPR-Cas systems from uncultivated microbes." Nature 542.7640 (2017): 237-241;

Zetsche, Bernd, et al. "Cpf1 is a single RNA-guided endonuclease of a class 2 CRISPR-Cas system." Cell 163.3 (2015): 759-771; and Morgan, Richard D., et al. "The MmeI family: type II restriction-modification enzymes that employ single-strand modification for host protection." Nucleic acids research 37.15 (2009): 5208-5221.

In various embodiments are disclosed polynucleotide or polynucleotides encoding for a constant region of a CRISPR single guide RNA (sgRNA) or CRISPR targeting RNA (crRNA) comprising a non-palindromic recognition site for a type II restriction enzyme, the non-palindromic recognition site being oriented in a manner recognized by the type II restriction enzyme for cutting a site that is 17 to 27 base pairs past an end of the polynucleotide. In various embodiments, the polynucleotides encode for a plurality of sgRNAs or crRNAs. The polynucleotide of various embodiments is double-stranded with sense and antisense strands and the non-palindromic recognition site of various embodiments is oriented in a manner recognized by the type II restriction enzyme for cutting a site that is 17 to 27 base pairs upstream from a 5' end of the sense strand or downstream from a 3' end of the antisense strand. In other embodiments, the polynucleotide is double-stranded with sense and antisense strands and the non-palindromic recognition site of various embodiments is oriented in a manner recognized by the type II restriction enzyme for cutting a site that is 17 to 27 base pairs downstream from a 3' end of the sense strand or upstream from a 5' end of the antisense strand.

As shown in FIG. 1, CRISPR protein forms a complex with a guide RNA and is capable of binding or modifying by, for example, cleaving, nicking, methylating, or demethylating a target nucleic acid or a polypeptide associated with the target nucleic acid. One example of a CRISPR protein, CRISPR/Cas9, is described in PCT Patent Application Publication No. WO 2016/196805 and references referred in WO 2016/196805, which are also incorporated in its entirety by reference herein. The Cas9 protein utilizes variable regions to bind specific sequences of DNA in a genome. Examples of Cas9 proteins are from *Streptococcus pyogenes* or *Staphylococcus Aureus*. The Cas9 protein utilizes guide RNAs to bind specific regions of a DNA sequence. Cpf1 is another protein, which uses a guide RNA in order to bind a specific sequence in genomic DNA. Cpf1 is from *Francisella novicida* and also cuts DNA making a staggered cut.

CRISPR proteins such as Cas9 and Cpf1 utilize variable regions to bind specific sequences of DNA in a genome. Particularly, CRISPR proteins such as Cpf1 and Cas9 use a guide RNA. The guide RNA provides target specificity to the complex by having a nucleotide sequence that is complementary to a sequence of a target nucleic acid. A number of methods have been employed to create guide RNAs. In one example, two RNA segments known as CRISPR RNA (crRNA) and trans-activating crRNA (tracrRNA) have commentary portions allowing them to combine to form an RNA duplex known as a crRNA/tracrRNA complex. The crRNA/tracrRNA complex has structures such as or similar to hairpin/stem-loop structures and are recognized by CRISPR proteins. Another method is using single RNA segments (e.g. single guide RNA or sgRNA) that can form hairpin or stem-loop structures and are recognized by CRISPR proteins. The guide RNA such as crRNA and sgRNA includes two segments: a variable region, which is also known as a targeting region; and a constant region, which is also known as a scaffold region to which the CRISPR protein binds to. The term "region" is understood to mean a segment/section/region of a molecule, e.g., a contiguous stretch of nucleotides in a nucleic acid molecule. A "region" can also mean a region/section of a complex such that a segment may comprise regions of more than one molecule. The guide RNA includes hairpin regions, which are conserved regions which bind to the CRISPR proteins such as Cas9 and Cpf1. These hairpin regions are located in the constant region of the guide RNA.

For example, a constant region for sgRNA with nucleotide sequence of SEQ ID NO: 3 is recognized by CRISPR Cas9 protein. The sgRNA with nucleotide sequence of SEQ ID NO: 3 can be transcribed from a double stranded polynucleotide having sense strand with nucleotide sequence of SEQ ID NO: 1 and an antisense with nucleotide sequence of SEQ ID NO: 2.

In another example, a constant region for sgRNA with nucleotide sequence of SEQ ID NO: 151 is recognized by CRISPR Cpf1 protein. The sgRNA with nucleotide sequence of SEQ ID NO: 151 can be transcribed from a double stranded polynucleotide having sense strand with nucleotide sequence of SEQ ID NO: 149 and an antisense with nucleotide sequence of SEQ ID NO: 150.

Figure 2:
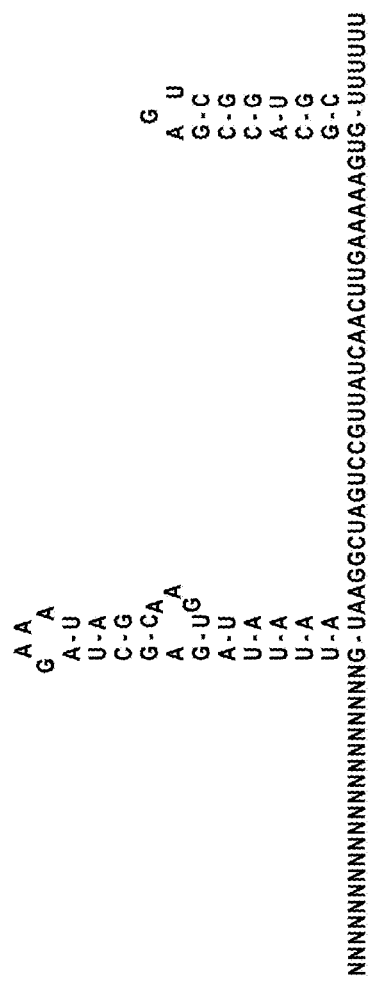
FIG. 2 shows an example of an sgRNA with nucleotide sequence of SEQ ID NO: 416 forming hairpin/stem-loop structures.
Figure 4A:
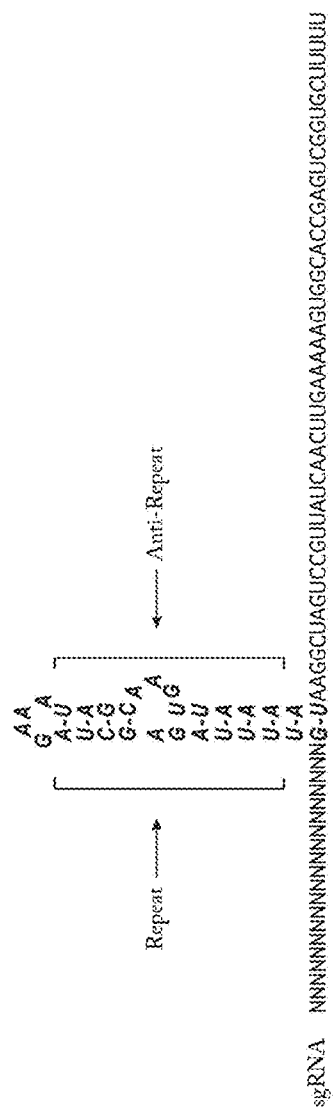
FIG. 4A shows the hairpin structure of a wildtype cRNA for CRISPR Cas9 (SEQ ID NO: 423).

As shown in FIGS. 2, 4A, and 5A, the CRISPR sgRNA(s) or cRNA(s) encoded by the polynucleotide or polynucleotides of various embodiments has at least one hairpin/stem-loop structure. In various embodiments, the CRISPR sgRNA(s) or cRNA(s) encoded by the polynucleotide or polynucleotides has one hairpin/stem-loop structure that are recognized by a CRISPR protein such as Cpf1. In another embodiment, the CRISPR sgRNA(s) or cRNA(s) encoded by the polynucleotide or polynucleotides has a plurality of hairpin/stem-loop structures that are recognized by a CRISPR protein such as Cas9.

In various embodiments, the sequence of the polynucleotide or polynucleotides encoding for a constant region of a CRISPR sgRNA or crRNA excluding or including the non-palindromic recognition site, and optionally a substantially complimentary site to the non-palindromic recognition site, has a homology or percent identity similar to an endogenous sequence of a CRISPR guide RNA or the hairpin regions such that the hairpin regions transcribed from the polynucleotide form and are recognized by a CRISPR protein.

In various embodiments, the CRISPR sgRNA(s) or cRNA(s) encoded by the polynucleotide or polynucleotides of various embodiments are recognized by any CRISPR protein. The CRISPR protein of various embodiments can include, for example, Class 1 or Class 2 CRISPR systems. The CRISPR protein of various embodiments can include, for example, Type I, Type II, Type III, Type IV, or Type V CRISPR systems.

In various embodiments are disclosed polynucleotides encoding for a constant region of a CRISPR single guide RNA (sgRNA) or CRISPR targeting RNA (crRNA) having the following sequence:

$5'-CR1_{N1}-RS_{N2}-CR2_{N3}-3'$ where:
CR1 is a first constant region with a nucleotide(s) or modified nucleotide(s) including Adenine (A or a), Guanine (G or g), Cytosine (C or c), or Tyrosine (T or t);
N1 is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides;
RS is a non-palindromic recognition site for a type II restriction enzyme with a nucleotide(s) or modified nucleotide(s) including Adenine (A or a), Guanine (G or g), Cytosine (C or c), or Tyrosine (T or t);
N2 is 4, 5, 6, 7, or 8;
CR2 is a second constant region with a nucleotide(s) or modified nucleotide(s) including Adenine (A or a), Guanine (G or g), Cytosine (C or c), or Tyrosine (T or t); and
N3 is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides;
wherein $RS_{N2}$ is oriented in a manner recognized by the type II restriction enzyme for cutting a site that is 17 to 27 base pairs past a 5' or 3' end of the polynucleotide.

In various embodiments are disclosed polynucleotides encoding for a constant region of a CRISPR single guide RNA (sgRNA) or CRISPR targeting RNA (crRNA) having the at least one of the following sequences:

$5'-VR_{N4}-CR1_{N1}-RS_{N2}-CR2_{N3}-3'$ or $5'-CR1_{N1}-RS_{N2}-CR2_{N3}-VR_{N4}-3'$ where:
VR is a variable region (e.g. targeting region) with a nucleotide(s) or modified nucleotide(s) including Adenine (A or a), Guanine (G or g), Cytosine (C or c), or Tyrosine (T or t);
N4 is 17, 18, 19, 20, 21, 22, 23, 24, 25, 26, or 27 nucleotides;
CR1 is a first constant region with a nucleotide(s) or modified nucleotide(s) including Adenine (A or a), Guanine (G or g), Cytosine (C or c), or Tyrosine (T or t);
N1 is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides;
RS is a non-palindromic recognition site for a type II restriction enzyme with a nucleotide(s) or modified nucleotide(s) including Adenine (A or a), Guanine (G or g), Cytosine (C or c), or Tyrosine (T or t);
N2 is 4, 5, 6, 7, or 8;
CR2 is a second constant region with a nucleotide(s) or modified nucleotide(s) including Adenine (A or a), Guanine (G or g), Cytosine (C or c), or Tyrosine (T or t); and
N3 is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides;
wherein $RS_{N2}$ is oriented in a manner recognized by the type II restriction enzyme for cutting a site that is 17 to 27 base pairs past a 5' or 3' end of the polynucleotide.

In various embodiments, N1 or N3 is range between any two number of nucleotides listed for N1 and N3 above.

In various embodiments, N2 is range between any two number of nucleotides listed for N2 above.

In various embodiments, N4 is range between any two number of nucleotides listed for N4 above.

The non-palindromic recognition site of the polynucleotide of various embodiments has a sequence recognized by a type II restriction enzyme is a type IIS restriction enzyme. In various embodiments, the non-palindromic recognition site in a manner recognized by the type II restriction enzyme for cutting a site that is 17, 18, 19, 20, 21, 22, 23, 24, 25, 26, or 27 base pairs past an end of the polynucleotide. In various embodiments, the cutting site is a range between any two base pair lengths past an end of the polynucleotide. In various embodiments, the non-palindromic recognition site is oriented in a manner recognized by the type II restriction enzyme for cutting a site that 17 to 27 base pairs past an end of the polynucleotide. In another embodiment, the non-palindromic recognition site is oriented in a manner recognized by the type II restriction enzyme for cutting a site that 18 to 24 base pairs past an end of the polynucleotide.

The type IIS restriction enzyme of various embodiments can include, for example, NmeAIII, MmeI, CstMI, EcoP15I, ApyPI, AquII, AquIII, AquIV, CdpI, CstMI, DraRI, DrdIV, EsaSSI, MaqI, NhaXI, NlaCI, PlaDI, PspOMII, PspPRI, RceI, RpaB5I, SdeAI, SpoDI, BsbI, or combinations thereof. The recognition sites for listed restriction enzymes are listed below (where the recognition site for each is followed by the cleavage distance):
ApyPI: ATCGAC(20/18)
AquII: GCCGNAC(20/18)
AquIII: GAGGAG(20/18)
AquIV: GRGGAAG(20/18)
CdpI: GCGGAG(20/18)
CstMI: AAGGAG(20/18)
DraRI: CAAGNAC(20/18)
DrdIV: TACGAC(20/18)
EsaSSI: GACCAC(20/18)
MaqI: CRTTGAC(20/18)
MmeI: TCCRAC(20/18)
NhaXI: CAAGRAG(20/18)
NlaCI: CATCAC(19/17)
NmeAIII: GCCGAG(21/19)
PlaDI: CATCAG(21/19)
PspOMII: CGCCCAR(20/18)
PspPRI: CCYCAG(21/19)
RceI: CATCGAC(20/18)
RpaB5I: CGRGGAC(20/18)
SdeAI: CAGRAG(21/19)
SpoDI: GCGGRAG(20/18)
BsbI: CAACAC(21/19)
EcoP15I: CAGCAG(25/27)

In various embodiments, the polynucleotide further includes a region having a sequence substantially complementary the sequence of non-palindromic recognition site. The complementary region of various embodiments can be spaced either upstream of downstream from the non-palindromic recognition site. When transcribed, the complementary sequence of sgRNA is capable of forming bonds with the non-palindromic recognition site such that hairpins or stem-loop structures form.

In various embodiments, the nucleotide can have a second restriction site or be prepared to have ends compatible with DNA digested with restriction enzymes that cut at protospacer adjacent motif (PAM) sites. Restriction enzymes that cut at PAM sites include, for example: HpaII, MspI, ScrFI, BfaI, and PacI. The recognition sites for the listed restriction enzymes are listed below.
HpaII: C/CGG
MspI: C/CGG
ScrFI: CC/NGG
BfaI: C/TAG
PacI TTAAT/TAA In various embodiments, the polynucleotide or polynucleotides encoding for a constant region of a CRISPR sgRNA or crRNA excluding or including the non-palindromic recognition site or the non-palindromic recognition site and the complimentary region has at least 80%, 85%, 90%, 95%, 99%, or 100% identity to at least one of SEQ ID NO: 4; SEQ ID NO: 9; SEQ ID NO: 14; SEQ ID NO: 19; SEQ ID NO: 24; SEQ ID NO: 29; SEQ ID NO: 34; SEQ ID NO: 39; SEQ ID NO: 44; SEQ ID NO: 49; SEQ ID NO: 54; SEQ ID NO: 59; SEQ ID NO: 64; SEQ ID NO: 69; SEQ ID NO: 74; SEQ ID NO: 79; SEQ ID NO: 84; SEQ ID NO: 89; SEQ ID NO: 94; SEQ ID NO: 99; SEQ ID NO: 104; SEQ ID NO: 109; SEQ ID NO: 114; SEQ ID NO: 119; SEQ ID NO: 124; SEQ ID NO: 129; SEQ ID NO: 134; SEQ ID NO: 139; SEQ ID NO: 144; SEQ ID NO: 152; SEQ ID NO: 157; SEQ ID NO: 162; SEQ ID NO: 167; SEQ ID NO: 172; SEQ ID NO: 177; SEQ ID NO: 182; SEQ ID NO: 187; SEQ ID NO: 192; SEQ ID NO: 197; SEQ ID NO: 202; SEQ ID NO: 207; SEQ ID NO: 212; SEQ ID NO: 217; SEQ ID NO: 222; SEQ ID NO: 227; SEQ ID NO: 232; SEQ ID NO: 237; SEQ ID NO: 242; SEQ ID NO: 247; SEQ ID NO: 252; SEQ ID NO: 257; SEQ ID NO: 262; SEQ ID NO: 267; SEQ ID NO: 272; SEQ ID NO: 277; SEQ ID NO: 282; SEQ ID NO: 287; SEQ ID NO: 292; SEQ ID NO: 297; SEQ ID NO: 302; SEQ ID NO: 307; SEQ ID NO: 312; SEQ ID NO: 317; SEQ ID NO: 322; SEQ ID NO: 327; SEQ ID NO: 332; SEQ ID NO: 337; SEQ ID NO: 342; SEQ ID NO: 347; SEQ ID NO: 352; SEQ ID NO: 357; SEQ ID NO: 362; SEQ ID NO: 367; SEQ ID NO: 372; SEQ ID NO: 377; SEQ ID NO: 382; SEQ ID NO: 387; SEQ ID NO: 392; SEQ ID NO: 397; or SEQ ID NO: 402.

In various embodiments, the polynucleotide or polynucleotides encoding for a constant region of a CRISPR sgRNA or crRNA comprise or are SEQ ID NO: 4; SEQ ID NO: 9; SEQ ID NO: 14; SEQ ID NO: 19; SEQ ID NO: 24; SEQ ID NO: 29; SEQ ID NO: 34; SEQ ID NO: 39; SEQ ID NO: 44; SEQ ID NO: 49; SEQ ID NO: 54; SEQ ID NO: 59; SEQ ID NO: 64; SEQ ID NO: 69; SEQ ID NO: 74; SEQ ID NO: 79; SEQ ID NO: 84; SEQ ID NO: 89; SEQ ID NO: 94; SEQ ID NO: 99; SEQ ID NO: 104; SEQ ID NO: 109; SEQ ID NO: 114; SEQ ID NO: 119; SEQ ID NO: 124; SEQ ID NO: 129; SEQ ID NO: 134; SEQ ID NO: 139; SEQ ID NO: 144; SEQ ID NO: 152; SEQ ID NO: 157; SEQ ID NO: 162; SEQ ID NO: 167; SEQ ID NO: 172; SEQ ID NO: 177; SEQ ID NO: 182; SEQ ID NO: 187; SEQ ID NO: 192; SEQ ID NO: 197; SEQ ID NO: 202; SEQ ID NO: 207; SEQ ID NO: 212; SEQ ID NO: 217; SEQ ID NO: 222; SEQ ID NO: 227; SEQ ID NO: 232; SEQ ID NO: 237; SEQ ID NO: 242; SEQ ID NO: 247; SEQ ID NO: 252; SEQ ID NO: 257; SEQ ID NO: 262; SEQ ID NO: 267; SEQ ID NO: 272; SEQ ID NO: 277; SEQ ID NO: 282; SEQ ID NO: 287; SEQ ID NO: 292; SEQ ID NO: 297; SEQ ID NO: 302; SEQ ID NO: 307; SEQ ID NO: 312; SEQ ID NO: 317; SEQ ID NO: 322; SEQ ID NO: 327;

SEQ ID NO: 332; SEQ ID NO: 337; SEQ ID NO: 342; SEQ ID NO: 347; SEQ ID NO: 352; SEQ ID NO: 357; SEQ ID NO: 362; SEQ ID NO: 367; SEQ ID NO: 372; SEQ ID NO: 377; SEQ ID NO: 382; SEQ ID NO: 387; SEQ ID NO: 392; SEQ ID NO: 397; SEQ ID NO: 402; or SEQ ID NO: 407.

The following are examples of various polynucleotides encoding for sgRNAs or crRNAs recognized by CRISPR Cas9 proteins. SEQ ID NO: 4 to SEQ ID NO: 148 relate to Cas9 systems.

The following examples highlights MmeI site TCCRAC at an end, 1 base pair from an end, or 2 base pairs from an end. The variable region of the examples can be 18, 19, or 20 base pairs long.

Figure 4B:
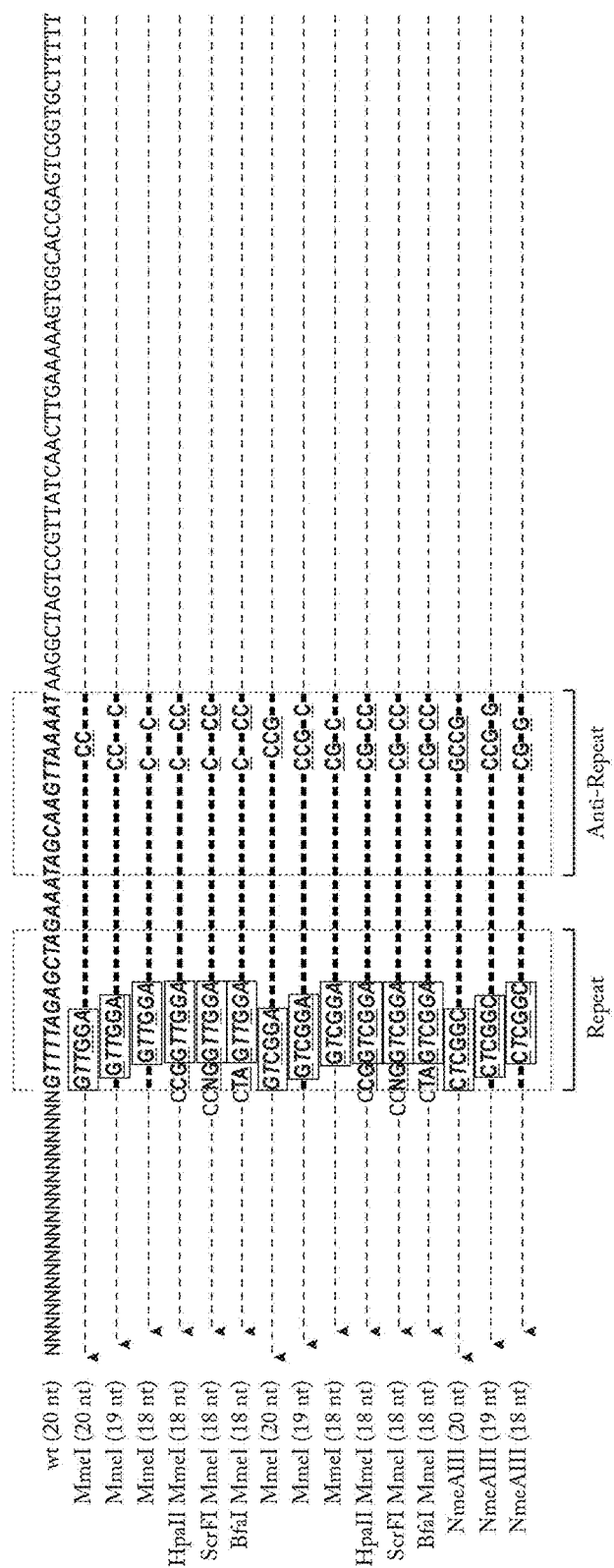
FIG. 4B shows polynucleotides of various embodiments encoding for an sgRNA or crRNA recognized by a CRIPSR Cas9 protein and having non-palindromic recognition site for MmeI, NmeAIII, HpaII or MspI, ScrFI, and BfaI. *S. pyogenes* crRNA sequence was modified to insert binding sites for restriction enzymes while maintaining secondary structure. WT crRNA indicates the previously published CRISPR sgRNA sequence for Cas9 binding. Areas surrounded by dotted lines indicate the hairpin region. Binding sites are shown surrounded by a solid line. Underlined letters indicate bases that do not match the original sequence. SEQ ID NOS: 424 to 439 are shown in descending order.

In various embodiments with MmeI site TCCRAC as shown in FIG. 4B, the polynucleotide is double stranded having sense strand SEQ ID NO: 4 and antisense strand SEQ ID NO: 5. When DNA containing a variable region is ligated to the polynucleotide and subsequently digested with MmeI, the polynucleotide has sense strand SEQ ID NO: 6 and antisense strand SEQ ID NO: 7 that can be transcribed to an sgRNA or crRNA with sequence SEQ ID NO: 8.

In various embodiments with MmeI site TCCRAC as shown in FIG. 4B, the polynucleotide is double stranded having sense strand SEQ ID NO: 9 and antisense strand SEQ ID NO: 10. When DNA containing a variable region is ligated to the polynucleotide and subsequently digested with MmeI, the polynucleotide has sense strand SEQ ID NO: 11 and antisense strand SEQ ID NO: 12 that can be transcribed to an sgRNA or crRNA with sequence SEQ ID NO: 13.

In various embodiments with MmeI site TCCRAC as shown in FIG. 4B, the polynucleotide is double stranded having sense strand SEQ ID NO: 14 and antisense strand SEQ ID NO: 15. When DNA containing a variable region is ligated to the polynucleotide and subsequently digested with MmeI, the polynucleotide has sense strand SEQ ID NO: 16 and antisense strand SEQ ID NO: 17 that can be transcribed to an sgRNA or crRNA with sequence SEQ ID NO: 18.

In various embodiments with MmeI site TCCRAC and HpaII site C/CGG or MspI site C/CGG as shown in FIG. 4B, the polynucleotide is double stranded having sense strand SEQ ID NO: 19 and antisense strand SEQ ID NO: 20. The polynucleotide can be digested with HpaII or MspI to form a compatible end. When DNA containing a variable region is ligated to the polynucleotide and subsequently digested with MmeI, the polynucleotide has sense strand SEQ ID NO: 21 and antisense strand SEQ ID NO: 22 that can be transcribed to an sgRNA or crRNA with sequence SEQ ID NO: 23.

In various embodiments with MmeI site TCCRAC and ScrFI site CC/NGG as shown in FIG. 4B, the polynucleotide is double stranded having sense strand SEQ ID NO: 24 and antisense strand SEQ ID NO: 25. The polynucleotide can be digested with ScrFI to form a compatible end. When DNA containing a variable region is ligated to the polynucleotide and subsequently digested with MmeI, the polynucleotide has sense strand SEQ ID NO: 26 and antisense strand SEQ ID NO: 27 that can be transcribed to an sgRNA or crRNA with sequence SEQ ID NO: 28.

In various embodiments with MmeI site TCCRAC and BfaI site C/TAG as shown in FIG. 4B, the polynucleotide is double stranded having sense strand SEQ ID NO: 29 and antisense strand SEQ ID NO: 30. The polynucleotide can be digested with BfaI to form a compatible end. When DNA containing a variable region is ligated to the polynucleotide and subsequently digested with MmeI, the polynucleotide has sense strand SEQ ID NO: 31 and antisense strand SEQ ID NO: 32 that can be transcribed to an sgRNA or crRNA with sequence SEQ ID NO: 33.

The following examples highlights NmeAIII site GCCGAG at an end, 1 base pair from an end, or 2 base pairs from an end. The variable region of the examples can be 18, 19, or 20 base pairs long.

In various embodiments with NmeAIII site GCCGAG as shown in FIG. 4B, the polynucleotide is double stranded having sense strand SEQ ID NO: 34 and antisense strand SEQ ID NO: 35. When DNA containing a variable region is ligated to the polynucleotide and subsequently digested with NmeAIII, the polynucleotide has sense strand SEQ ID NO: 36 and antisense strand SEQ ID NO: 37 that can be transcribed to an sgRNA or crRNA with sequence SEQ ID NO: 38.

In various embodiments with NmeAIII site GCCGAG as shown in FIG. 4B, the polynucleotide is double stranded having sense strand SEQ ID NO: 39 and antisense strand SEQ ID NO: 40. When DNA containing a variable region is ligated to the polynucleotide and subsequently digested with NmeAIII, the polynucleotide has sense strand SEQ ID NO: 41 and antisense strand SEQ ID NO: 42 that can be transcribed to an sgRNA or crRNA with sequence SEQ ID NO: 43.

In various embodiments with NmeAIII site GCCGAG as shown in FIG. 4B, the polynucleotide is double stranded having sense strand SEQ ID NO: 44 and antisense strand SEQ ID NO: 45. When DNA containing a variable region is ligated to the polynucleotide and subsequently digested with NmeAIII, the polynucleotide has sense strand SEQ ID NO: 46 and antisense strand SEQ ID NO: 47 that can be transcribed to an sgRNA or crRNA with sequence SEQ ID NO: 48.

The following examples highlight different restriction enzymes sites at an end. The variable regions of the following examples can be 18 base pairs, 19 base pairs, or 20 base pairs long.

In various embodiments with ApyPI site ATCGAC, the polynucleotide is double stranded having sense strand SEQ ID NO: 49 and antisense strand SEQ ID NO: 50. When DNA containing a variable region is ligated to the polynucleotide and subsequently digested with ApyPI, the polynucleotide has sense strand SEQ ID NO: 51 and antisense strand SEQ ID NO: 52 that can be transcribed to an sgRNA or crRNA with sequence SEQ ID NO: 53.

In various embodiments with AquII site GCCGNAC, the polynucleotide is double stranded having sense strand SEQ ID NO: 54 and antisense strand SEQ ID NO: 55. When DNA containing a variable region is ligated to the polynucleotide and subsequently digested with AquII, the polynucleotide has sense strand SEQ ID NO: 56 and antisense strand SEQ ID NO: 57 that can be transcribed to an sgRNA or crRNA with sequence SEQ ID NO: 58.

In various embodiments with AquIII site GAGGAG, the polynucleotide is double stranded having sense strand SEQ ID NO: 59 and antisense strand SEQ ID NO: 60. When DNA containing a variable region is ligated to the polynucleotide and subsequently digested with AquIII, the polynucleotide has sense strand SEQ ID NO: 61 and antisense strand SEQ ID NO: 62 that can be transcribed to an sgRNA or crRNA with sequence SEQ ID NO: 63.

In various embodiments with AquIV site GRGGAAG, the polynucleotide is double stranded having sense strand SEQ ID NO: 64 and antisense strand SEQ ID NO: 65. When DNA containing a variable region is ligated to the polynucleotide and subsequently digested with AquIV, the polynucleotide has sense strand SEQ ID NO: 66 and antisense strand SEQ ID NO: 67 that can be transcribed to an sgRNA or crRNA with sequence SEQ ID NO: 68.

In various embodiments with CdpI site GCGGAG, the polynucleotide is double stranded having sense strand SEQ ID NO: 69 and antisense strand SEQ ID NO: 70. When DNA containing a variable region is ligated to the polynucleotide and subsequently digested with CdpI, the polynucleotide has sense strand SEQ ID NO: 71 and antisense strand SEQ ID NO: 72 that can be transcribed to an sgRNA or crRNA with sequence SEQ ID NO: 73.

In various embodiments with CstMI site AAGGAG, the polynucleotide is double stranded having sense strand SEQ ID NO: 74 and antisense strand SEQ ID NO: 75. When DNA containing a variable region is ligated to the polynucleotide and subsequently digested with CstMI, the polynucleotide has sense strand SEQ ID NO: 76 and antisense strand SEQ ID NO: 77 that can be transcribed to an sgRNA or crRNA with sequence SEQ ID NO: 78.

In various embodiments with DraRI site CAAGNAC, the polynucleotide is double stranded having sense strand SEQ ID NO: 79 and antisense strand SEQ ID NO: 80. When DNA containing a variable region is ligated to the polynucleotide and subsequently digested with DraRI, the polynucleotide has sense strand SEQ ID NO: 81 and antisense SEQ ID NO: 82 that can be transcribed to an sgRNA or crRNA with sequence SEQ ID NO: 83.

In various embodiments with DrdIV site TACGAC, the polynucleotide is double stranded having sense strand SEQ ID NO: 84 and antisense strand SEQ ID NO: 85. When DNA containing a variable region is ligated to the polynucleotide and subsequently digested with DrdIV, the polynucleotide has sense strand SEQ ID NO: 86 and antisense SEQ ID NO: 87 that can be transcribed to an sgRNA or crRNA with sequence SEQ ID NO: 88.

In various embodiments with EsaSSI site GACCAC, the polynucleotide is double stranded having sense strand SEQ ID NO: 89 and antisense strand SEQ ID NO: 90. When DNA containing a variable region is ligated to the polynucleotide and subsequently digested with EsaSSI, the polynucleotide has sense strand SEQ ID NO: 91 and anti sense strand SEQ ID NO: 92 that can be transcribed to an sgRNA or crRNA with sequence SEQ ID NO: 93.

In various embodiments with MaqI site CRTTGAC, the polynucleotide is double stranded having sense strand SEQ ID NO: 94 and antisense strand SEQ ID NO: 95. When DNA containing a variable region is ligated to the polynucleotide and subsequently digested with MaqI, the polynucleotide has sense strand SEQ ID NO: 96 and antisense strand SEQ ID NO: 97 that can be transcribed to an sgRNA or crRNA with sequence SEQ ID NO: 98.

In various embodiments with NhaXI site CAAGRAG, the polynucleotide is double stranded having sense strand SEQ ID NO: 99 and antisense strand SEQ ID NO: 100. When DNA containing a variable region is ligated to the polynucleotide and subsequently digested with NhaXI, the polynucleotide has sense strand SEQ ID NO: 101 and antisense strand SEQ ID NO: 102 that can be transcribed to an sgRNA or crRNA with sequence SEQ ID NO: 103.

In various embodiments with NlaCI site CATCAC, the polynucleotide is double stranded having sense strand SEQ ID NO: 104 and antisense strand SEQ ID NO: 105. When DNA containing a variable region is ligated to the polynucleotide and subsequently digested with NlaCI, the polynucleotide has sense strand SEQ ID NO: 106 and antisense strand SEQ ID NO: 107 that can be transcribed to an sgRNA or crRNA with sequence SEQ ID NO: 108.

In various embodiments with PlaDI site CATCAG, the polynucleotide is double stranded having sense strand SEQ ID NO: 109 and antisense strand SEQ ID NO: 110. When DNA containing a variable region is ligated to the polynucleotide and subsequently digested with PlaDI, the polynucleotide has sense strand SEQ ID NO: 111 and antisense strand SEQ ID NO: 112 that can be transcribed to an sgRNA or crRNA with sequence SEQ ID NO: 113.

In various embodiments with PspOMII site CGCCCAR, the polynucleotide is double stranded having sense strand SEQ ID NO: 114 and antisense strand SEQ ID NO: 115. When DNA containing a variable region is ligated to the polynucleotide and subsequently digested with PspOMII, the polynucleotide has sense strand SEQ ID NO: 116 and antisense strand SEQ ID NO: 117 that can be transcribed to an sgRNA or crRNA with sequence SEQ ID NO: 118.

In various embodiments with PspPRI site CCYCAG, the polynucleotide is double stranded having sense strand SEQ ID NO: 119 and antisense strand SEQ ID NO: 120. When DNA containing a variable region is ligated to the polynucleotide and subsequently digested with PspPRI, the polynucleotide has sense strand SEQ ID NO: 121 and antisense strand SEQ ID NO: 122 that can be transcribed to an sgRNA or crRNA with sequence SEQ ID NO: 123.

In various embodiments with RceI site CATCGAC, the polynucleotide is double stranded having sense strand SEQ ID NO: 124 and antisense strand SEQ ID NO: 125. When DNA containing a variable region is ligated to the polynucleotide and subsequently digested with RceI, the polynucleotide has sense strand SEQ ID NO: 126 and antisense strand SEQ ID NO: 127 that can be transcribed to an sgRNA or crRNA with sequence SEQ ID NO: 128.

In various embodiments with RpaB5I site CGRGGAC, the polynucleotide is double stranded having sense strand SEQ ID NO: 129 and antisense strand SEQ ID NO: 130. When DNA containing a variable region is ligated to the polynucleotide and subsequently digested with RpaB5I, the polynucleotide has sense strand SEQ ID NO: 131 and antisense strand SEQ ID NO: 132 that can be transcribed to an sgRNA or crRNA with sequence SEQ ID NO: 133.

In various embodiments with SdeAI site CAGRAG, the polynucleotide is double stranded having sense strand SEQ ID NO: 134 and antisense strand SEQ ID NO: 135. When DNA containing a variable region is ligated to the polynucleotide and subsequently digested with SdeAI, the polynucleotide has sense strand SEQ ID NO: 136 and antisense strand SEQ ID NO: 137 that can be transcribed to an sgRNA or crRNA with sequence SEQ ID NO: 138.

In various embodiments with SpoDI site GCGGRAG, the polynucleotide is double stranded having sense strand SEQ ID NO: 139 and antisense strand SEQ ID NO: 140. When DNA containing a variable region is ligated to the polynucleotide and subsequently digested with SpoDI, the polynucleotide has sense strand SEQ ID NO: 141 and antisense strand SEQ ID NO: 142 that can be transcribed to an sgRNA or crRNA with sequence SEQ ID NO: 143.

In various embodiments with BsbI site CAACAC, the polynucleotide is double stranded having sense strand SEQ ID NO: 144 and antisense strand SEQ ID NO: 145. When DNA containing a variable region is ligated to the polynucleotide and subsequently digested with BsbI, the polynucleotide has sense strand SEQ ID NO: 146 and antisense strand SEQ ID NO: 147 that can be transcribed to an sgRNA or crRNA with sequence SEQ ID NO: 148.

The following are examples of various polynucleotides encoding for sgRNAs or crRNAs recognized by CRISPR Cpf1 proteins. SEQ ID NO: 152 to SEQ ID NO: 406 relate to Cpf1 systems.

The following examples highlights MmeI site TCCRAC at an end, 1 base pair from an end, or 2 base pairs from an end. The variable region of the examples can be 18, 19, or 20 base pairs long.

In various embodiments with MmeI site TCCRAC as shown in FIG. 5B, the polynucleotide is double stranded having sense strand SEQ ID NO: 152 and antisense strand SEQ ID NO: 153. When DNA containing a variable region is ligated to the polynucleotide and subsequently digested with MmeI, the polynucleotide has sense strand SEQ ID NO: 154 and antisense strand SEQ ID NO: 155 that can be transcribed to an sgRNA or crRNA with sequence SEQ ID NO: 156.

In various embodiments with MmeI site TCCRAC as shown in FIG. 5B, the polynucleotide is double stranded having sense strand SEQ ID NO: 157 and antisense strand SEQ ID NO: 158. When DNA containing a variable region is ligated to the polynucleotide and subsequently digested with MmeI, the polynucleotide has sense strand SEQ ID NO: 159 and antisense strand SEQ ID NO: 160 that can be transcribed to an sgRNA or crRNA with sequence SEQ ID NO: 161.

In various embodiments with MmeI site TCCRAC as shown in FIG. 5B, the polynucleotide is double stranded having sense strand SEQ ID NO: 162 and antisense strand SEQ ID NO: 163. The polynucleotide can be prepared to have an AT overhang allowing the nucleotide to be compatible with DNA digested with PacI. When DNA containing a variable region is ligated to the polynucleotide and subsequently digested with MmeI, the polynucleotide has sense strand SEQ ID NO: 164 and antisense strand SEQ ID NO: 165 that can be transcribed to an sgRNA or crRNA with sequence SEQ ID NO: 166.

In various embodiments with MmeI site TCCRAC as shown in FIG. 5B, the polynucleotide is double stranded having sense strand SEQ ID NO: 167 and antisense strand SEQ ID NO: 168. The polynucleotide can be prepared to have an AT overhang allowing the nucleotide to be compatible with DNA digested with PacI. When DNA containing a variable region is ligated to the polynucleotide and subsequently digested with MmeI, the polynucleotide has sense strand SEQ ID NO: 169 and antisense strand SEQ ID NO: 170 that can be transcribed to an sgRNA or crRNA with sequence SEQ ID NO: 171.

The following examples highlights NmeAIII site GCCGAG at an end, 1 base pair from an end, or 2 base pair from an end. The variable region of the examples can be 18, 19, or 20 base pairs long.

In various embodiments with NmeAIII site GCCGAG as shown in FIG. 5B, the polynucleotide is double stranded having sense strand SEQ ID NO: 172 and antisense strand SEQ ID NO: 173. When DNA containing a variable region is ligated to the polynucleotide and subsequently digested with NmeAIII, the polynucleotide has sense strand SEQ ID NO: 174 and antisense strand SEQ ID NO: 175 that can be transcribed to an sgRNA or crRNA with sequence SEQ ID NO: 176.

In various embodiments with NmeAIII site GCCGAG as shown in FIG. 5B, the polynucleotide is double stranded having sense strand SEQ ID NO: 177 and antisense strand SEQ ID NO: 178. When DNA containing a variable region is ligated to the polynucleotide and subsequently digested with NmeAIII, the polynucleotide has sense strand SEQ ID NO: 179 and antisense strand SEQ ID NO: 180 that can be transcribed to an sgRNA or crRNA with sequence SEQ ID NO: 181.

In various embodiments with NmeAIII site GCCGAG as shown in FIG. 5B, the polynucleotide is double stranded having sense strand SEQ ID NO: 182 and antisense strand SEQ ID NO: 183. The polynucleotide can be prepared to have an AT overhang allowing the nucleotide to be compatible with DNA digested with PacI. When DNA containing a variable region is ligated to the polynucleotide and subsequently digested with NmeAIII, the polynucleotide has sense strand SEQ ID NO: 184 and antisense strand SEQ ID NO: 185 that can be transcribed to an sgRNA or crRNA with sequence SEQ ID NO: 186.

In various embodiments with NmeAIII site GCCGAG as shown in FIG. 5B, the polynucleotide is double stranded having sense strand SEQ ID NO: 187 and antisense strand SEQ ID NO: 188. The polynucleotide can be prepared to have an AT overhang allowing the nucleotide to be compatible with DNA digested with PacI. When DNA containing a variable region is ligated to the polynucleotide and subsequently digested with NmeAIII, the polynucleotide has sense strand SEQ ID NO: 189 and antisense strand SEQ ID NO: 190 that can be transcribed to an sgRNA or crRNA with sequence SEQ ID NO: 191.

The following examples highlight different restriction enzymes sites 1 base pair from an end. The variable regions of the following examples can be 19 base pairs or 20 base pairs long.

In various embodiments with ApyPI site ATCGAC, the polynucleotide is double stranded having sense strand SEQ ID NO: 192 and antisense strand SEQ ID NO: 193. When DNA containing a variable region is ligated to the polynucleotide and subsequently digested with ApyPI, the polynucleotide has sense strand SEQ ID NO: 194 and antisense strand SEQ ID NO: 195 that can be transcribed to an sgRNA or crRNA with sequence SEQ ID NO: 196.

In various embodiments with AquII site GCCGNAC, the polynucleotide is double stranded having sense strand SEQ ID NO: 197 and antisense strand SEQ ID NO: 198. When DNA containing a variable region is ligated to the polynucleotide and subsequently digested with AquII, the polynucleotide has sense strand SEQ ID NO: 199 and antisense strand SEQ ID NO: 200 that can be transcribed to an sgRNA or crRNA with sequence SEQ ID NO: 201.

In various embodiments with AquIII site GAGGAG, the polynucleotide is double stranded having sense strand SEQ ID NO: 202 and antisense strand SEQ ID NO: 203. When DNA containing a variable region is ligated to the polynucleotide and subsequently digested with AquIII, the polynucleotide has sense strand SEQ ID NO: 204 and antisense strand SEQ ID NO: 205 that can be transcribed to an sgRNA or crRNA with sequence SEQ ID NO: 206.

In various embodiments with AquIV site GRGGAAG, the polynucleotide is double stranded having sense strand SEQ ID NO: 207 and antisense strand SEQ ID NO: 208. When DNA containing a variable region is ligated to the polynucleotide and subsequently digested with AquIV, the polynucleotide has sense strand SEQ ID NO: 209 and antisense strand SEQ ID NO: 210 that can be transcribed to an sgRNA or crRNA with sequence SEQ ID NO: 211.

In various embodiments with CdpI site GCGGAG, the polynucleotide is double stranded having sense strand SEQ ID NO: 212 and antisense strand SEQ ID NO: 213. When DNA containing a variable region is ligated to the polynucleotide and subsequently digested with CdpI, the polynucleotide has sense strand SEQ ID NO: 214 and antisense strand SEQ ID NO: 215 that can be transcribed to an sgRNA or crRNA with sequence SEQ ID NO: 216.

In various embodiments with CstMI site AAGGAG, the polynucleotide is double stranded having sense strand SEQ ID NO: 217 and antisense strand SEQ ID NO: 218. When DNA containing a variable region is ligated to the polynucleotide and subsequently digested with CstMI, the polynucleotide has sense strand SEQ ID NO: 219 and antisense strand SEQ ID NO: 220 that can be transcribed to an sgRNA or crRNA with sequence SEQ ID NO: 221.

In various embodiments with DraRI site CAAGNAC, the polynucleotide is double stranded having sense strand SEQ ID NO: 222 and antisense strand SEQ ID NO: 223. When DNA containing a variable region is ligated to the polynucleotide and subsequently digested with DraRI, the polynucleotide has sense strand SEQ ID NO: 224 and antisense strand SEQ ID NO: 225 that can be transcribed to an sgRNA or crRNA with sequence SEQ ID NO: 226.

In various embodiments with DrdIV site TACGAC, the polynucleotide is double stranded having sense strand SEQ ID NO: 227 and antisense strand SEQ ID NO: 228. When DNA containing a variable region is ligated to the polynucleotide and subsequently digested with DrdIV, the polynucleotide has sense strand SEQ ID NO: 229 and antisense strand SEQ ID NO: 230 that can be transcribed to an sgRNA or crRNA with sequence SEQ ID NO: 231.

In various embodiments with EsaSSI site GACCAC, the polynucleotide is double stranded having sense strand SEQ ID NO: 232 and antisense strand SEQ ID NO: 233. When DNA containing a variable region is ligated to the polynucleotide and subsequently digested with EsaSSI, the polynucleotide has sense strand SEQ ID NO: 234 and antisense strand SEQ ID NO: 235 that can be transcribed to an sgRNA or crRNA with sequence SEQ ID NO: 236.

In various embodiments with MaqI site CRTTGAC, the polynucleotide is double stranded having sense strand SEQ ID NO: 237 and antisense strand SEQ ID NO: 238. When DNA containing a variable region is ligated to the polynucleotide and subsequently digested with MaqI, the polynucleotide has sense strand SEQ ID NO: 239 and antisense strand SEQ ID NO: 240 that can be transcribed to an sgRNA or crRNA with sequence SEQ ID NO: 241.

In various embodiments with NhaXI site CAAGRAG, the polynucleotide is double stranded having sense strand SEQ ID NO: 242 and antisense strand SEQ ID NO: 243. When DNA containing a variable region is ligated to the polynucleotide and subsequently digested with NhaXI, the polynucleotide has sense strand SEQ ID NO: 244 and antisense strand SEQ ID NO: 245 that can be transcribed to an sgRNA or crRNA with sequence SEQ ID NO: 246.

In various embodiments with NlaCI site CATCAC, the polynucleotide is double stranded having sense strand SEQ ID NO: 247 and antisense strand SEQ ID NO: 248. When DNA containing a variable region is ligated to the polynucleotide and subsequently digested with NlaCI, the polynucleotide has sense strand SEQ ID NO: 249 and antisense strand SEQ ID NO: 250 that can be transcribed to an sgRNA or crRNA with sequence SEQ ID NO: 251.

In various embodiments with PlaDI site CATCAG, the polynucleotide is double stranded having sense strand SEQ ID NO: 252 and antisense strand SEQ ID NO: 253. When DNA containing a variable region is ligated to the polynucleotide and subsequently digested with PlaDI, the polynucleotide has sense strand SEQ ID NO: 254 and antisense strand SEQ ID NO: 255 that can be transcribed to an sgRNA or crRNA with sequence SEQ ID NO: 256.

In various embodiments with PspOMII site CGCCCAR, the polynucleotide is double stranded having sense strand SEQ ID NO: 257 and antisense strand SEQ ID NO: 258. When DNA containing a variable region is ligated to the polynucleotide and subsequently digested with PspOMII, the polynucleotide has sense strand SEQ ID NO: 259 and antisense strand SEQ ID NO: 260 that can be transcribed to an sgRNA or crRNA with sequence SEQ ID NO: 261.

In various embodiments with PspPRI site CCYCAG, the polynucleotide is double stranded having sense strand SEQ ID NO: 262 and antisense strand SEQ ID NO: 263. When DNA containing a variable region is ligated to the polynucleotide and subsequently digested with PspPRI, the polynucleotide has sense strand SEQ ID NO: 264 and antisense strand SEQ ID NO: 265 that can be transcribed to an sgRNA or crRNA with sequence SEQ ID NO: 266.

In various embodiments with RceI site CATCGAC, the polynucleotide is double stranded having sense strand SEQ ID NO: 267 and antisense strand SEQ ID NO: 268. When DNA containing a variable region is ligated to the polynucleotide and subsequently digested with RceI, the polynucleotide has sense strand SEQ ID NO: 269 and antisense strand SEQ ID NO: 270 that can be transcribed to an sgRNA or crRNA with sequence SEQ ID NO: 271.

In various embodiments with RpaB5I site CGRGGAC, the polynucleotide is double stranded having sense strand SEQ ID NO: 272 and antisense strand SEQ ID NO: 273. When DNA containing a variable region is ligated to the polynucleotide and subsequently digested with RpaB5I, the polynucleotide has sense strand SEQ ID NO: 274 and antisense strand SEQ ID NO: 275 that can be transcribed to an sgRNA or crRNA with sequence SEQ ID NO: 276.

In various embodiments with SdeAI site CAGRAG, the polynucleotide is double stranded having sense strand SEQ ID NO: 277 and antisense strand SEQ ID NO: 278. When DNA containing a variable region is ligated to the polynucleotide and subsequently digested with SdeAI, the polynucleotide has sense strand SEQ ID NO: 279 and antisense strand SEQ ID NO: 280 that can be transcribed to an sgRNA or crRNA with sequence SEQ ID NO: 281.

In various embodiments with SpoDI site GCGGRAG, the polynucleotide is double stranded having sense strand SEQ ID NO: 282 and antisense strand SEQ ID NO: 283. When DNA containing a variable region is ligated to the polynucleotide and subsequently digested with SpoDI, the polynucleotide has sense strand SEQ ID NO: 284 and antisense strand SEQ ID NO: 285 that can be transcribed to an sgRNA or crRNA with sequence SEQ ID NO: 286.

In various embodiments with BsbI site CAACAC, the polynucleotide is double stranded having sense strand SEQ ID NO: 287 and antisense strand SEQ ID NO: 288. When DNA containing a variable region is ligated to the polynucleotide and subsequently digested with BsbI, the polynucleotide has sense strand SEQ ID NO: 289 and antisense strand SEQ ID NO: 290 that can be transcribed to an sgRNA or crRNA with sequence SEQ ID NO: 291.

The following examples highlight different restriction enzymes sites 2 base pair from an end. The variable regions of the following examples can be 18 base pairs or 19 base pairs long.

In various embodiments with ApyPI site ATCGAC, the polynucleotide is double stranded having sense strand SEQ ID NO: 292 and antisense strand SEQ ID NO: 293. When DNA containing a variable region is ligated to the polynucleotide and subsequently digested with ApyPI, the polynucleotide has sense strand SEQ ID NO: 294 and antisense strand SEQ ID NO: 295 that can be transcribed to an sgRNA or crRNA with sequence SEQ ID NO: 296.

In various embodiments with AquII site GCCGNAC, the polynucleotide is double stranded having sense strand SEQ ID NO:297 and antisense strand SEQ ID NO: 298. When DNA containing a variable region is ligated to the polynucleotide and subsequently digested with AquII, the polynucleotide has sense strand SEQ ID NO: 299 and antisense strand SEQ ID NO: 300 that can be transcribed to an sgRNA or crRNA with sequence SEQ ID NO: 301.

In various embodiments with AquIII site GAGGAG, the polynucleotide is double stranded having sense strand SEQ ID NO:302 and antisense strand SEQ ID NO: 303. When DNA containing a variable region is ligated to the polynucleotide and subsequently digested with AquIII, the polynucleotide has sense strand SEQ ID NO: 304 and antisense strand SEQ ID NO: 305 that can be transcribed to an sgRNA or crRNA with sequence SEQ ID NO: 306.

In various embodiments with AquIV site GRGGAAG, the polynucleotide is double stranded having sense strand SEQ ID NO:307 and antisense strand SEQ ID NO: 308. When DNA containing a variable region is ligated to the polynucleotide and subsequently digested with AquIV, the polynucleotide has sense strand SEQ ID NO: 309 and antisense strand SEQ ID NO: 310 that can be transcribed to an sgRNA or crRNA with sequence SEQ ID NO: 311.

In various embodiments with CdpI site GCGGAG, the polynucleotide is double stranded having sense strand SEQ ID NO:312 and antisense strand SEQ ID NO: 313. When DNA containing a variable region is ligated to the polynucleotide and subsequently digested with CdpI, the polynucleotide has sense strand SEQ ID NO: 314 and antisense strand SEQ ID NO: 315 that can be transcribed to an sgRNA or crRNA with sequence SEQ ID NO: 316.

In various embodiments with CstMI site AAGGAG, the polynucleotide is double stranded having sense strand SEQ ID NO:317 and antisense strand SEQ ID NO: 318. When DNA containing a variable region is ligated to the polynucleotide and subsequently digested with CstMI, the polynucleotide has sense strand SEQ ID NO: 319 and antisense strand SEQ ID NO: 320 that can be transcribed to an sgRNA or crRNA with sequence SEQ ID NO: 321.

In various embodiments with DraRI site CAAGNAC, the polynucleotide is double stranded having sense strand SEQ ID NO:322 and antisense strand SEQ ID NO: 323. When DNA containing a variable region is ligated to the polynucleotide and subsequently digested with DraRI, the polynucleotide has sense strand SEQ ID NO: 324 and antisense strand SEQ ID NO: 325 that can be transcribed to an sgRNA or crRNA with sequence SEQ ID NO: 326.

In various embodiments with DrdIV site TACGAC, the polynucleotide is double stranded having sense strand SEQ ID NO:327 and antisense strand SEQ ID NO: 328. When DNA containing a variable region is ligated to the polynucleotide and subsequently digested with DrdIV, the polynucleotide has sense strand SEQ ID NO: 329 and antisense strand SEQ ID NO: 330 that can be transcribed to an sgRNA or crRNA with sequence SEQ ID NO: 331.

In various embodiments with EsaSSI site GACCAC, the polynucleotide is double stranded having sense strand SEQ ID NO:332 and antisense strand SEQ ID NO: 333. When DNA containing a variable region is ligated to the polynucleotide and subsequently digested with EsaSSI, the polynucleotide has sense strand SEQ ID NO: 334 and antisense strand SEQ ID NO: 335 that can be transcribed to an sgRNA or crRNA with sequence SEQ ID NO: 336.

In various embodiments with MaqI site CRTTGAC, the polynucleotide is double stranded having sense strand SEQ ID NO:337 and antisense strand SEQ ID NO: 338. When DNA containing a variable region is ligated to the polynucleotide and subsequently digested with MaqI, the polynucleotide has sense strand SEQ ID NO: 339 and antisense strand SEQ ID NO: 340 that can be transcribed to an sgRNA or crRNA with sequence SEQ ID NO: 341.

In various embodiments with NhaXI site CAAGRAG, the polynucleotide is double stranded having sense strand SEQ ID NO:342 and antisense strand SEQ ID NO: 343. When DNA containing a variable region is ligated to the polynucleotide and subsequently digested with NhaXI, the polynucleotide has sense strand SEQ ID NO: 344 and antisense strand SEQ ID NO: 345 that can be transcribed to an sgRNA or crRNA with sequence SEQ ID NO: 346.

In various embodiments with PlaDI site CATCAG, the polynucleotide is double stranded having sense strand SEQ ID NO:347 and antisense strand SEQ ID NO: 348. When DNA containing a variable region is ligated to the polynucleotide and subsequently digested with PlaDI, the polynucleotide has sense strand SEQ ID NO: 349 and antisense strand SEQ ID NO: 350 that can be transcribed to an sgRNA or crRNA with sequence SEQ ID NO: 351.

In various embodiments with PspOMII site CGCCCAR, the polynucleotide is double stranded having sense strand SEQ ID NO:352 and antisense strand SEQ ID NO: 353. When DNA containing a variable region is ligated to the polynucleotide and subsequently digested with PspOMII, the polynucleotide has sense strand SEQ ID NO: 354 and antisense strand SEQ ID NO: 355 that can be transcribed to an sgRNA or crRNA with sequence SEQ ID NO: 356.

In various embodiments with PspPRI site CCYCAG, the polynucleotide is double stranded having sense strand SEQ ID NO:357 and antisense strand SEQ ID NO: 358. When DNA containing a variable region is ligated to the polynucleotide and subsequently digested with PspPRI, the polynucleotide has sense strand SEQ ID NO: 359 and antisense strand SEQ ID NO: 360 that can be transcribed to an sgRNA or crRNA with sequence SEQ ID NO: 361.

In various embodiments with RceI site CATCGAC, the polynucleotide is double stranded having sense strand SEQ ID NO:362 and antisense strand SEQ ID NO: 363. When DNA containing a variable region is ligated to the polynucleotide and subsequently digested with RceI, the polynucleotide has sense strand SEQ ID NO: 364 and antisense strand SEQ ID NO: 365 that can be transcribed to an sgRNA or crRNA with sequence SEQ ID NO: 366.

In various embodiments with RpaB5I site CGRGGAC, the polynucleotide is double stranded having sense strand SEQ ID NO:367 and antisense strand SEQ ID NO: 368. When DNA containing a variable region is ligated to the polynucleotide and subsequently digested with RpaB5I, the polynucleotide has sense strand SEQ ID NO: 369 and antisense strand SEQ ID NO: 370 that can be transcribed to an sgRNA or crRNA with sequence SEQ ID NO: 371.

In various embodiments with SdeAI site CAGRAG, the polynucleotide is double stranded having sense strand SEQ ID NO:372 and antisense strand SEQ ID NO: 373. When DNA containing a variable region is ligated to the polynucleotide and subsequently digested with SdeAI, the polynucleotide has sense strand SEQ ID NO: 374 and antisense strand SEQ ID NO: 375 that can be transcribed to an sgRNA or crRNA with sequence SEQ ID NO: 376.

In various embodiments with SpoDI site GCGGRAG, the polynucleotide is double stranded having sense strand SEQ ID NO:377 and antisense strand SEQ ID NO: 378. When DNA containing a variable region is ligated to the polynucleotide and subsequently digested with SpoDI, the polynucleotide has sense strand SEQ ID NO: 379 and antisense strand SEQ ID NO: 380 that can be transcribed to an sgRNA or crRNA with sequence SEQ ID NO: 381.

In various embodiments with, the polynucleotide is double stranded having sense strand SEQ ID NO:382 and antisense strand SEQ ID NO: 383. When DNA containing a variable region is ligated to the polynucleotide and subsequently digested with BsbI, the polynucleotide has sense strand SEQ ID NO: 384 and antisense strand SEQ ID NO: 385 that can be transcribed to an sgRNA or crRNA with sequence SEQ ID NO: 386.

The following examples highlight different restriction enzymes sites 3 base pair from an end. The variable regions of the following examples can be 18 base pairs long.

In various embodiments with PlaDI site CATCAG, the polynucleotide is double stranded having sense strand SEQ ID NO:387 and antisense strand SEQ ID NO: 388. When DNA containing a variable region is ligated to the polynucleotide and subsequently digested with PlaDI, the polynucleotide has sense strand SEQ ID NO: 389 and antisense strand SEQ ID NO: 390 that can be transcribed to an sgRNA or crRNA with sequence SEQ ID NO: 391.

In various embodiments with PspPRI site CCYCAG, the polynucleotide is double stranded having sense strand SEQ ID NO:392 and antisense strand SEQ ID NO: 393. When DNA containing a variable region is ligated to the polynucleotide and subsequently digested with PspPRI, the polynucleotide has sense strand SEQ ID NO: 394 and antisense strand SEQ ID NO: 395 that can be transcribed to an sgRNA or crRNA with sequence SEQ ID NO: 396.

In various embodiments with SdeAI site CAGRAG, the polynucleotide is double stranded having sense strand SEQ ID NO:397 and antisense strand SEQ ID NO: 398. When DNA containing a variable region is ligated to the polynucleotide and subsequently digested with SdeAI, the polynucleotide has sense strand SEQ ID NO: 399 and antisense strand SEQ ID NO: 400 that can be transcribed to an sgRNA or crRNA with sequence SEQ ID NO: 401.

In various embodiments with BsbI site CAACAC, the polynucleotide is double stranded having sense strand SEQ ID NO:402 and antisense strand SEQ ID NO: 403. When DNA containing a variable region is ligated to the polynucleotide and subsequently digested with BsbI, the polynucleotide has sense strand SEQ ID NO: 404 and antisense strand SEQ ID NO: 405 that can be transcribed to an sgRNA or crRNA with sequence SEQ ID NO: 406.

In various embodiments, the polynucleotide(s) further include(s) a modification at least one modified sugar moiety, at least one modified internucleotide linkage, at least one modified nucleotide, or combinations thereof. The modification of various embodiments can be located at or adjacent to the end of the polynucleotide. In various embodiments, the internucleotide linkage includes phosphorothioate, alkylphosphonate, phosphorodithioate, alkylphosphonothioate, phosphoramidate, carbamate, carbonate, phosphate triester, acetamidate, carboxymethyl ester, or combinations thereof. In various embodiments, the modified nucleotide is selected from a peptide nucleic acid, a locked nucleic acid (LNA), or combination thereof. In various embodiments, the modified sugar moiety is selected from: a 2'-O-methoxyethyl modified sugar moiety, a 2'-methoxy modified sugar moiety, a 2'-O-alkyl modified sugar moiety, a bicyclic sugar moiety, or combinations thereof. For example, the last two nucleotides from an end of the polynucleotide of various embodiments can have phosphate backbones that have been modified to include phosphorothioate. In this example, phosphorothioate is resistant to nuclease degradation and allows for the polynucleotide of various embodiments to be ligated with various types of DNA when during the ligation is occurring in the presence of nucleases.

In various embodiments, the polynucleotide(s) is/are attached, affixed, or immobilized on a support such as a solid support. The support of various embodiments can include two-dimensional surfaces such as microarray slides or three-dimensional surfaces such as beads or micro-spheres including polystyrene micro-spheres, magnetic microspheres, silica micro-spheres, or fluorescent micro-spheres.

In various embodiments are disclosed expression cassettes, plasmid, or vectors including the polynucleotide encoding for the CRISPR sgRNA or CRISPR crRNA. In other embodiments are disclosed expression cassettes, plasmid, or vectors including the polynucleotide encoding for the CRISPR sgRNA or CRISPR crRNA of various embodiments and a promoter polynucleotide operably linked to the polynucleotide of various embodiments, wherein the promoter polynucleotide is recognized by an RNA polymerase and is capable of directing the RNA polymerase to transcribe the CRISPR sgRNA or CRISPR crRNA from the polynucleotide of various embodiments. For example, the polynucleotide could be oriented within a plasmid including a topoisomerase as described in U.S. Pat. No. 5,766,891, which is incorporated in its entirety by reference herein, or a cloning system such as a TOPO® Cloning System (Thermo Fisher Scientific).

In various embodiments are disclosed methods and systems of generating CRISPR gRNA libraries, the methods and systems including the steps of: providing a first polynucleotide encoding for a constant region of a CRISPR sgRNA or CRISPR crRNA and having a non-palindromic recognition site for a type II restriction enzyme, wherein the non-palindromic recognition site is oriented in a manner recognized by the type II restriction enzyme to cut a site that is 17 to 27 base pairs past an end of the first polynucleotide; ligating DNA to the end of the first polynucleotide to form a second polynucleotide; and digesting the second polynucleotide with the type II restriction enzyme to form a third polynucleotide encoding a CRISPR sgRNA or CRISPR crRNA, wherein the type II restriction enzyme cuts the DNA at a site that is 17 to 27 base pairs from the end of the first polynucleotide. The methods/systems of various embodiments can include the first polynucleotide being a plurality of first polynucleotides; at least a portion of the plurality of first polynucleotides being ligated with DNA to form a plurality of second polynucleotides; and the plurality of second polynucleotides being digested with the type II restriction enzyme to form a plurality of third polynucleotides encoding a plurality of sgRNAs, where at least one of the plurality of sgRNAs has a targeting sequence different from the other sgRNAs. In various embodiments, the DNA prior to the ligation step is digested with a nuclease.

In various embodiments, the methods or systems can further include the step of generating/transcribing a CRISPR sgRNA or CRISPR crRNA generated/transcribed from the third polynucleotide. The methods or systems of various embodiments can further include providing or expressing a CRISPR protein and combining the CRISPR sgRNA or CRISPR crRNA, when complexed with a tracrRNA) with the CRISPR protein to form a CRISPR protein/guide RNA complex.

In various embodiments, the methods or systems can further include the step of inducing double strand breaks in DNA with the CRISPR protein/guide RNA complex.

In various embodiments, the methods/systems further include the step of ligating a promoter polynucleotide recognized by a RNA polymerase to an end of the third polynucleotide, wherein the promoter polynucleotide when ligated to the third polynucleotide is capable of directing the RNA polymerase to transcribe the sgRNA from the third polynucleotide.

The polynucleotide(s) of various embodiments can be attached, affixed, or immobilized on a support such as a solid support. The support of various embodiments can include two-dimensional surface such as microarray slides or three-dimensional surfaces such as beads or micro-spheres including bolystyrene micro-spheres, magnetic microspheres, silica micro-spheres, or fluorescent micro-spheres. In various embodiments, the methods and systems include the step of affixing the polynucleotides to the solid support or cleaving the polynucleotide from the solid support. The cleaving step can include chemically or photo-cleaving the polynucleotides form the support.

The method/systems of various embodiments can create complex libraries with reduced numbers in steps (for example, 5 steps) and in a very short time as compared to other systems (for example, in 3 hours). The methods/systems of various embodiments include a recognition site for a restriction enzyme such as MmeI endonuclease into a polynucleotide encoding for a sgRNA or crRNA. MmeI can cut 20-22 base pairs upstream of its recognition site (See FIGS. 3 and 4). Further, the polynucleotide when transcribed can maintain the stem loop structure necessary for CRISPR interactions.

Figure 6A:
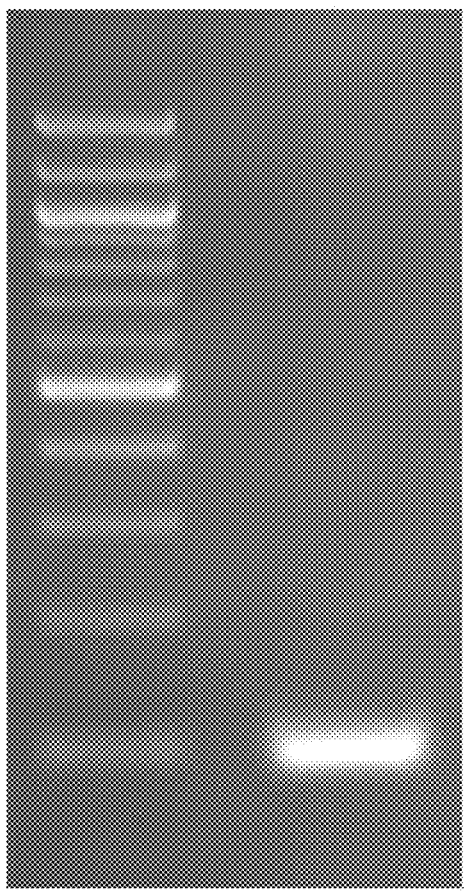
FIGS. 6A, 6B, 6C, and 6D illustrate fluorescent images of an ethidium bromide stained agarose gel outlining the methods/systems of generating guide RNA libraries of various embodiments.

FIGS. 6A-6D illustrates fluorescent images of an ethidium bromide stained agarose gel outlining the methods/systems of generating guide RNA libraries of various embodiments. As shown in FIG. 6A, a 100 base pair fragment (SEQ ID NO: 408) was amplified using polymerase chain reaction (PCR) on a linear polynucleotide containing a transgene encoding for an enhanced green fluorescent protein (SEQ ID NO: 407) using a forward primer (SEQ ID NO: 409) and reverse primer (SEQ ID NO: 410). FIG. 6A shows the 100 base pair fragment.

Figure 6B:
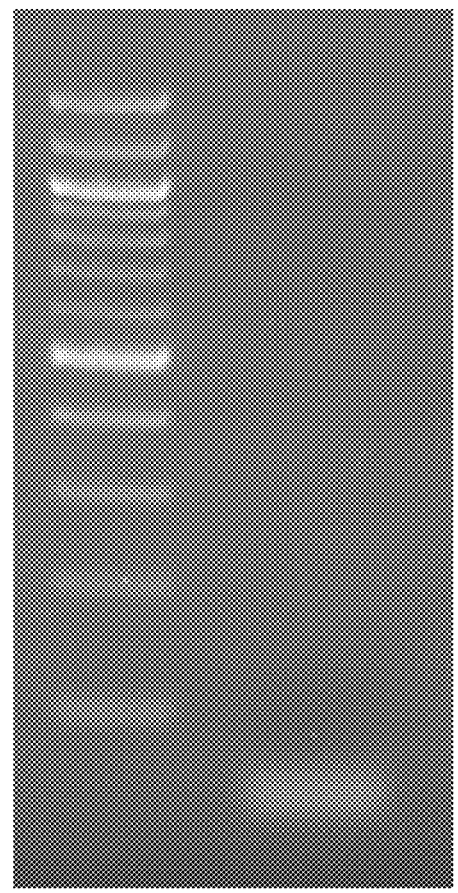

The fragment has a HpaII site starting at nucleotide 49 of SEQ ID NO: 408. The fragment was then digested into two products: SEQ ID NO: 411 and SEQ ID NO: 412. FIG. 6B shows the two products.

Figure 6C:
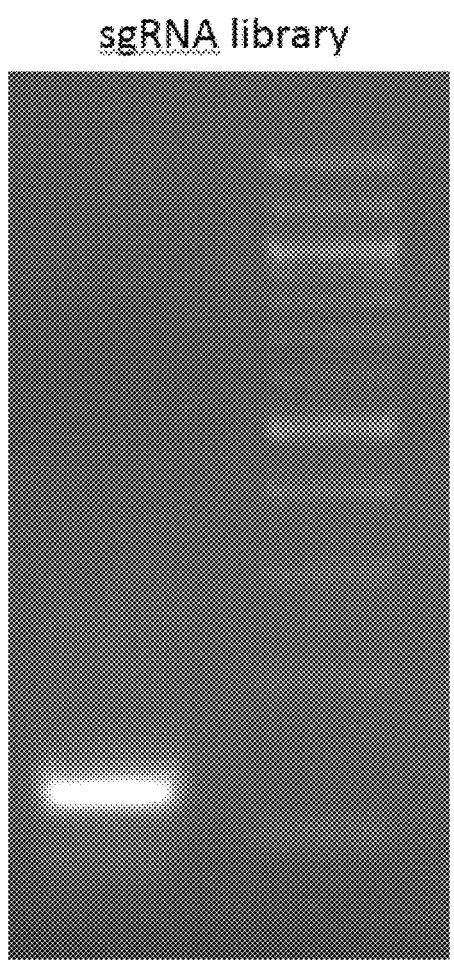
Figure 6D:
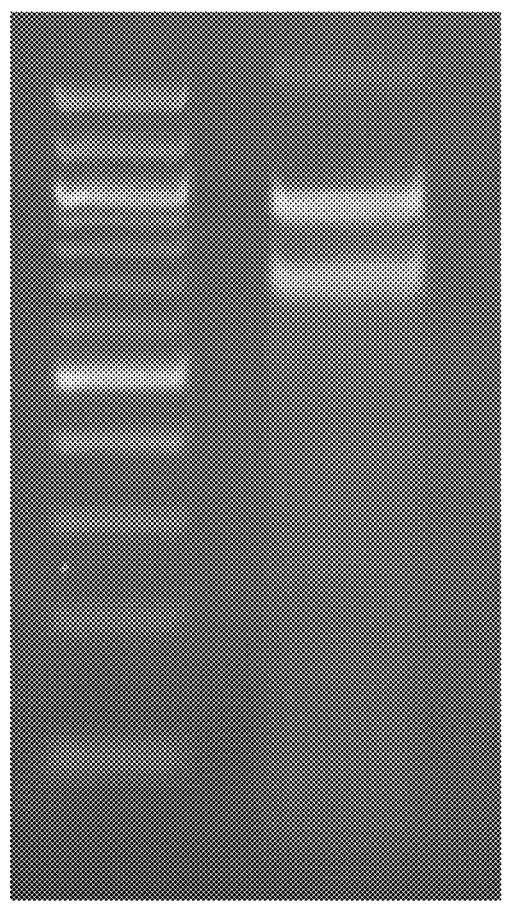

The two products were ligated to a polynucleotide encoding for a constant region of a CRISPR sgRNA. Thus, two sgRNAs with different variable regions were created. These two sgRNAs were then operably linked to a T7 promoter (SEQ ID NO: 415). FIG. 6C shows the product formed from the ligation. After ligation, the sgRNAs were digested with MmeI. Thus, the sgRNAs had two different variable regions: SEQ ID NO: 413 and SEQ ID NO: 414.

The sgRNAs were then combined with CRISPR Cas9 proteins and the linear polynucleotide containing the transgene encoding for an enhanced green fluorescent protein (SEQ ID NO: 412). As shown with asterisks in FIG. 6D, the sgRNAs were able to form complexes with the CRISPR Cas9 proteins and create double strand breaks the linear polynucleotide containing the transgene encoding for an enhanced green fluorescent protein (SEQ ID NO: 412) which are represented by the two bands or products on the agarose gel. Only two band are visualized since two sites are too close to each other to resolve.

Figure 3:
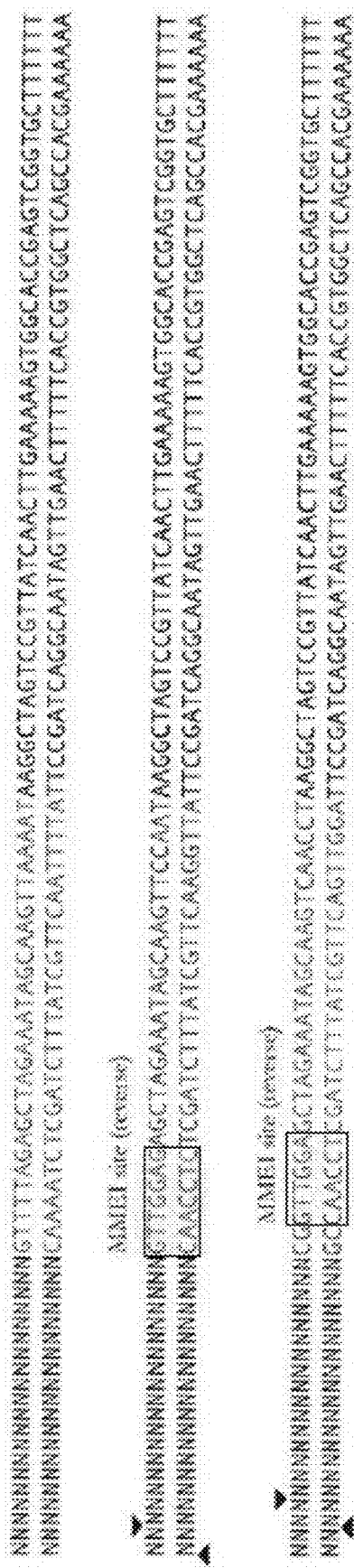
FIG. 3 shows a comparison of a double-stranded polynucleotide encoding for a sgRNA (top sequence; SEQ ID NOS: 417 and 418) to double-stranded polynucleotides of various embodiments encoding for sgRNAs and having non-palindromic recognition sites (middle (SEQ ID NOS: 418 and 419) and bottom sequences; SEQ ID NOS: 420 and 421).

Since the variable regions can be, for example, 17 to 27 nucleotides long, the polynucleotide can include different versions of the constant region such as, for example, one with the MmeI site at the end of the scaffold region (FIG. 3, middle sequence) and two with the binding site shifted two bases away from the edge (FIG. 3, bottom sequence). In the construct with the MmeI site located two bases from the edge of the scaffold region, further modification can be done to create a two-basepair overhang for more rapid ligation of the digested DNA to the scaffold. The two placements of the MmeI site will create mixtures of products with 20-22 bases or 18-20 base pair long targeting regions, respectively. Both of these variants show effective cutting in vitro in preliminary tests. A construct with the MmeI site shifted one base pair was not tested because it interfered with a thymine nucleotide that is predicted by crystal structure to interact directly with the Cas9, but is currently being generated and tested.

Using the methods and systems of various embodiments can allow for the creation guide RNA libraries without the need for adapter switching and associated cleanups needed as highlight in PCT Patent Application Publication No. WO 2016/196805. Using the methods and systems of various embodiments can allow the attachment of the constant region to beads to allow easy cleanup. To this end, the methods and systems of various embodiments can allow for the generation of libraries much more rapidly and efficiently than before. Other benefits of the methods and systems of various embodiments can include: decreased time, much lower cost, increased yield, and an ability to create a standardized kit applicable to a wide range of applications. In addition, having fewer steps makes troubleshooting much easier. In various embodiments, the following reagents or steps can be eliminated from the methods and systems of various embodiments: rSAP; mung bean nuclease when using MspI digestion protocol; drop dialysis; attachment and removal of intermediate linkers; cutting tandem repeats; size selections; gel extractions that can require overnight incubations; or second PCR amplification.

The following examples illustrate the various embodiments of the present invention. Those skilled in the art will recognize many variations that are within the spirit of the present invention and scope of the claims.

Example Protocol Using MspI (Estimated Time: 3-3.5 Hours)
1. Digest source DNA (DNA can be genomic, a PCR product, or double-stranded cDNA) (30 min)
1.1. Combine 1 ug of DNA with 5 ul Cutsmart buffer, 1 ul (MspI) and bring to 50 ul with water, incubate for 30 minutes at 37 C
2 ***Attach gRNA scaffolds to beads (30 min, concurrent with step 1 or provided in kit)
2.1. Place 10 ul of beads in a 1.5 ml microcentrifuge tube, place on magnet for 1 minute and discard supernatant
2.2. Add 500 ul of wash buffer, rock for 5 minutes, place on magnet for 1 minute and discard supernatant
2.3. Add 50 ul of scaffold (100 ng/ul biotinylated and annealed scaffold oligo) solution
2.4. Incubate for 10 minutes with gentle rocking, place on magnet for 1 minute and discard supernatant.
2.5. Wash with 500 ul IX cutsmart buffer, rock for 5 minutes, place on magnet for 1 minute and discard supernatant
3. Ligate DNA to scaffolds (10 min)
3.1. Add digested DNA mix from Step 1, 1 ul Ligase and 1 ul ATP+PEG to beads. Rock for 5 minutes, place on magnet for 1 minute and discard supernatant.
3.2. Wash with 500 ul IX cutsmart buffer, rock for 5 minutes, place on magnet for 1 minute and discard supernatant 4. Digest with MmeI (45 min)
4.1. Add 24 ul of IX cutsmart buffer and 1 ul of MmeI enzyme, incubate at 37 C for 30 min with rocking, place on magnet for 1 minute and discard supernatant.
4.2. Wash with 500 ul IX cutsmart buffer, rock for 5 minutes, place on magnet for 1 minute and discard supernatant
5. Ligate T7 promoter (10 minutes)
5.1. Add 50 ul T7 promoter mix, 1 ul Ligase and 1 ul ATP+PEG to beads. Rock for 5 minutes, place on magnet for 1 minute and discard supernatant.
5.2. Wash with 500 ul IX PCR buffer, rock for 5 minutes, place on magnet for 1 minute and discard supernatant
6. Amplify library (1 hour)
6.1. Resuspend beads in 50 ul PCR buffer containing 5 ul 10×PCR buffer, 0.5 ul dNTP, 0.5 ul Taq, 1 ul T7 and scaffold primers.
6.2. Transfer to PCR tube and amplify in PCR thermocycler using the following protocol:
6.3. Place beads on magnet and keep supernatant. Discard beads.

Example Protocol with Combination of Enzymes (Estimated Time: 3.5-4 Hours)
1. Digest source DNA (DNA can be genomic, a PCR product, or double-stranded cDNA) (1 hour)
1.1. Combine 1 ug of DNA with 5 ul Cutsmart buffer, 1 ul (Enzymes) and bring to 50 ul with water
1.2. Incubate for 30 minutes at 37 C, then add 1 ul mung bean nuclease and incubate 30 C for 30 min.
2 ***Attach gRNA scaffolds to beads (45 min, concurrent with step 1 or provided in kit)
2.1. Place 10 ul of beads in a 1.5 ml microcentrifuge tube, place on magnet for 1 minute and discard supernatant
2.2. Add 500 ul of wash buffer, rock for 10 minutes, place on magnet for 1 minute and discard supernatant
2.3. Add 50 ul of scaffold (100 ng/ul biotinylated and annealed scaffold oligo) solution
2.4. Incubate for 15 minutes with gentle rocking, place on magnet for 1 minute and discard supernatant.
2.5. Wash with 500 ul IX cutsmart buffer, rock for 5 minutes, place on magnet for 1 minute and discard supernatant
3. Ligate DNA to scaffolds (15 minutes)
3.1. Add digested DNA mix from Step 1, 1 ul Ligase and 1 ul ATP+PEG to beads. Rock for 10 minutes, place on magnet for 1 minute and discard supernatant.
3.2. Wash with 500 ul IX cutsmart buffer, rock for 5 minutes, place on magnet for 1 minute and discard supernatant
4. Digest with MmeI (1 hour)
4.1. Add 24 ul of IX cutsmart buffer and 1 ul of MmeI enzyme, incubate at 37 C for 1 hour with rocking, place on magnet for 1 minute and discard supernatant.
4.2. Wash with 500 ul IX cutsmart buffer, rock for 5 minutes, place on magnet for 1 minute and discard supernatant
5. Ligate T7 promoter (15 minutes)
5.1. Add 5 ul T7 promoter mix, 1 ul Ligase and 1 ul ATP+PEG to beads. Rock for 10 minutes, place on magnet for 1 minute and discard supernatant.
5.2. Wash with 500 ul IX PCR buffer, rock for 5 minutes, place on magnet for 1 minute and discard supernatant
6. Amplify library (1 hour)
6.1. Resuspend beads in 50 ul PCR buffer containing 5 ul 10×PCR buffer, 0.5 ul dNTP, 0.5 ul Taq, 1 ul T7 and scaffold primers.
6.2. Transfer to PCR tube and amplify in PCR thermocycler using the following protocol:
6.3. Place beads on magnet and keep supernatant. Discard beads.

Example Protocol Using MspI (Estimated Time: 3-3.5 Hours)
1. Digest source DNA (DNA can be genomic, a PCR product, or double-stranded cDNA) (30 min)
1.1. Combine 1 ug of DNA with 5 ul Cutsmart buffer, 1 ul (MspI) and bring to 50 ul with water, incubate for 30 minutes at 37 C
2 ***Attach gRNA scaffolds to beads (30 min, concurrent with step 1 or provided in kit)
2.1. Place 10 ul of beads in a 1.5 ml microcentrifuge tube, place on magnet for 1 minute and discard supernatant
2.2. Add 500 ul of wash buffer, rock for 5 minutes, place on magnet for 1 minute and discard supernatant
2.3. Add 50 ul of scaffold (100 ng/ul biotinylated and annealed scaffold oligo) solution
2.4. Incubate for 10 minutes with gentle rocking, place on magnet for 1 minute and discard supernatant.
2.5. Wash with 500 ul IX cutsmart buffer, rock for 5 minutes, place on magnet for 1 minute and discard supernatant
3. Ligate DNA to scaffolds (10 min)
3.1. Add digested DNA mix from Step 1, 1 ul Ligase and 1 ul ATP+PEG to beads. Rock for 5 minutes, place on magnet for 1 minute and discard supernatant.
3.2. Wash with 500 ul IX cutsmart buffer, rock for 5 minutes, place on magnet for 1 minute and discard supernatant
4. Digest with MmeI (45 min)
4.1. Add 24 ul of IX cutsmart buffer and 1 ul of MmeI enzyme, incubate at 37 C for 30 min with rocking, place on magnet for 1 minute and discard supernatant.
4.2. Wash with 500 ul IX cutsmart buffer, rock for 5 minutes, place on magnet for 1 minute and discard supernatant
5. Ligate T7 promoter (10 minutes)
5.1. Add 50 ul T7 promoter mix, 1 ul Ligase and 1 ul ATP+PEG to beads. Rock for 5 minutes, place on magnet for 1 minute and discard supernatant.
5.2. Wash with 500 ul IX PCR buffer, rock for 5 minutes, place on magnet for 1 minute and discard supernatant
6. Amplify library (1 hour)
6.1. Resuspend beads in 50 ul PCR buffer containing 5 ul 10×PCR buffer, 0.5 ul dNTP, 0.5 ul Taq, 1 ul T7 and scaffold primers.
6.2. Transfer to PCR tube and amplify in PCR thermocycler using the following protocol:
6.3. Place beads on magnet and keep supernatant. Discard beads.

Example Protocol with Combination of Enzymes (Estimated Time: 3.5-4 Hours)
1. Digest source DNA (DNA can be genomic, a PCR product, or double-stranded cDNA) (1 hour)
1.1. Combine 1 ug of DNA with 5 ul Cutsmart buffer, 1 ul (Enzymes) and bring to 50 ul with water
1.2. Incubate for 30 minutes at 37 C, then add 1 ul mung bean nuclease and incubate 30 C for 30 min.
2 ***Attach gRNA scaffolds to beads (45 min, concurrent with step 1 or provided in kit)
2.1. Place 10 ul of beads in a 1.5 ml microcentrifuge tube, place on magnet for 1 minute and discard supernatant
2.2. Add 500 ul of wash buffer, rock for 10 minutes, place on magnet for 1 minute and discard supernatant
2.3. Add 50 ul of scaffold (100 ng/ul biotinylated and annealed scaffold oligo) solution
2.4. Incubate for 15 minutes with gentle rocking, place on magnet for 1 minute and discard supernatant.

Bst Elution Protocol
Input DNA: 100 base pairs fragment 330 ng=5 pmols→(10 pmol of ends)
(1) HpaII digestion (37° C. for 15 minutes, 80° C. for 20 minutes)
39 μl Water
5 μl 10× cutsmart buffer 5 µl DNA
1 µl HpaII
(2) Scaffold adapter ligation (20° C. for 30 minutes, 65° C. for 10 minutes)
0.5 µl 10× Cutsmart buffer
3 µl scaffold adapter (10 µM)
1 µl ATP (10 mM)
1 µl T4 Ligase
(3) MmeI digestion (25° C. for 15 min, 65° C. for 20 min)
1 µl SAM (2.5 mM)
1 µl MmeI
(4) T7 adapter ligation (20° C. for 30 minutes, 65° C. for 10 minutes)
0.2 µl 10× Cutsmart buffer
6 µl T7 adapter (10 uM)
1 µl ATP (10 mM)
1 µl T4 Ligase
Suspend in 50 µl of washed capture beads (25° C. for 15 minutes) wash with 1× cutsmart buffer
(5) Bst elution and nick repair (45° C. for 30 minutes)
43 µl Water
5 µl 10× Cutsmart buffer
1 µl 10 mM dNTPs
1 µl Bst 3.0 polymerase
column purify 2 step phusion blocking PCR-anneal and extend at 64° C. for 10 seconds Endonuclease Protocol Input DNA: 100 base pairs fragment 330 ng=5 pmols→(10 pmol of ends)
(1) HpaII digestion (37° C. for 15 minutes, 80° C. for 20 minutes)
39 µl Water
5 µl 10× cutsmart buffer
5 µl DNA
1 µl HpaII
(2) Scaffold adapter ligation (20° C. for 30 minutes, 65° C. for 10 minutes)
0.5 µl 10× Cutsmart buffer
3 µl scaffold adapter (10 µM)
1 µl ATP (10 mM)
1 µl T4 Ligase
(3) MmeI digestion (25° C. for 15 min, 65° C. for 20 min)
1 µl SAM (2.5 mM)
1 µl MmeI
(4) T7 adapter ligation (20° C. for 30 minutes, 65° C. for 10 minutes)
0.2 µl 10× Cutsmart buffer
6 µl T7 adapter (10 uM)
1 µl ATP (10 mM)
1 µl T4 Ligase
(5) Exonuclease digestion and nick repair (37° C. for 1 hour)
5 µl 10× Cutsmart buffer
1 µl 10 mM dNTPs
1 µl Bst 3.0 polymerase
1 µl λ Exonuclease
1 µl Exonuclease I
column purify
2 step phusion blocking PCR-anneal and extend at 64° C. for 10 seconds Photo Cleaving Protocol Input DNA: 100 base pairs fragment 330 ng=5 pmols→(10 pmol of ends)
(1) HpaII digestion (37° C. for 15 minutes)
39 µl Water
5 µl 10× cutsmart buffer
5 µl DNA
1 µl HpaII
(2) Scaffold adapter ligation (20° C. for 30 minutes)
0.5 µl 10× Cutsmart buffer
3 µl scaffold adapter (10 µM)
1 µl ATP (10 mM)
1 µl T4 Ligase
Suspend in 50 µl of washed capture beads (25° C. for 15 minutes) wash with 1× cutsmart buffer
(3) MmeI digestion (25° C. for 15 min)
1 µl SAM (2.5 mM)
1 µl MmeI
wash with 1× cutsmart buffer
(4) T7 adapter ligation (20° C. for 30 minutes)
0.2 µl 10× Cutsmart buffer
6 µl T7 adapter (10 uM)
1 µl ATP (10 mM)
1 µl T4 Ligase
wash with 1× cutsmart buffer
(5) Bst nick repair (45° C. for 30 minutes)
43 µl Water
5 µl 10× Cutsmart buffer
1 µl 10 mM dNTPs
1 µl Bst 3.0 polymerase
wash with 1× cutsmart buffer
photocleave (long wave UV for 30 min)
column purify
2 step phusion blocking PCR-anneal and extend at 64° C. for 10 seconds Enzymatic CRISPR Library Generation Kit In various embodiments are disclosed kits for generating CRISPR guide RNA (gRNA) libraries comprising a polynucleotide or polynucleotides encoding for a constant region(s) of a CRISPR sgRNA or CRISPR crRNA and having a non-palindromic recognition site for a type II restriction enzyme, wherein the non-palindromic recognition site is oriented in a manner recognized by the type II restriction enzyme for cutting a site that is 17 to 27 base pairs past an end of the polynucleotide. The kit of various embodiments can further include the restriction enzyme or enzymes; supports such as a solid support, wherein polynucleotides are capable of being immobilized on at least one of the supports or are immobilized on the at least one of the supports; a promoter polynucleotide recognized by a RNA polymerase; or combinations thereof.

Most current applications of CRISPR systems such as Cas9 and Cpf1 take advantage of this simplicity to target single or small sets of genetic loci. Although this results in rapid and efficient targeting of single genes, CRISPR-Cas9 is not widely used for screening mutants to discover novel genes and pathways, because of the expense of synthesizing complex libraries. We have generated a novel method for creating CRISPR libraries efficiently and inexpensively from any source of DNA, including genomic DNA from any species, PCR products, double-stranded cDNA generated from RNA, etc. There are two versions of the kit, one using a combination of enzymes that comprehensively digests the input DNA at PAM sites to create all possible CRISPRS and one that selects one of these enzymes to create good, but not comprehensive coverage. The advantage of the second is that it removes the need for blunting the digestion products. Advantages of the kit of various embodiments may include, for example: wide range of applications across any species; different polynucleotides can be manufactured for different kits and can include other components; reduced amounts of enzymes; limited variations for the kit for DNA source or species; simplified protocol that can be completed relatively quickly (for example, 4 hours); limited variation in protocol for difference sources of DNA; or limits a user from having to use additional equipment.

The following examples illustrate the various embodiments of the present invention. Those skilled in the art will recognize many variations that are within the spirit of the present invention and scope of the claims.

The kit components can include, for example: magnetic beads with attached oligos, where one example can include streptavidin beads with biotinylated polynucleotides; restriction enzymes including enzyme mixtures; mung bean nuclease; enzyme digestion buffer; PEG; ATP; or a T7 promoter oligo.

The following examples illustrate the various embodiments of the present invention. Those skilled in the art will recognize many variations that are within the spirit of the present invention and scope of the claims.

Specific Aims

Congenital heart defects (CHDs) are the most common type of birth defect in the United States. However, only 20% of cases have a known etiology, limiting accurate diagnosis and treatment. Therefore, continued research to identify the genes and pathways driving embryonic heart development is essential to improve our ability to diagnose and treat CHD.

One of the most prolific sources for identifying disease-causing alleles underlying CHDs has been forward genetic screens in model organisms, especially zebrafish. Studying genes identified by forward genetics has not only led to greater understanding of the mechanisms and pathways driving heart development, but have also directly identified the genes underlying human disease. Despite their great utility in gene discovery, forward genetic screens are hindered by two major limitations: 1) Genetic mapping of loci exhibiting the phenotype can take considerable amounts of time, and 2) The random mutagenesis used can affect any locus in the genome, and the resulting alleles yield defects unrelated to the phenotype of interest. I have previously created a program, called MMAPPR, that uses RNA-seq to accelerate the genetic mapping process, reducing the time required to genetically map and identify candidate mutations from years to weeks, thus addressing the first concern. Here, we propose to address the second limitation by using the method and systems of various embodiments that will use CRISPR-Cas9 and a tissue-specific cDNA library to target all of—and only—the genes expressed in the tissue of interest, thus limiting mutations to genes expressed in the appropriate tissues at relevant time points while maintaining the breadth and unbiased gene selection necessary for true gene discovery. The CRISPR library generated by the methods and systems of various embodiments will be diluted to create small pools of CRISPR guide RNAs. Each pool will be injected into zebrafish embryos at the one-cell stage and screened at 48 and 72 hpf for looping, chamber and valve defects and sequencing used to identify targets associated with the phenotype. The CRISPR library generated by the methods and systems of various embodiments and PGC-specific mRNA will also will be co-injected into one-cell zebrafish embryos. This will result in mutagenesis specifically in the PGCs, allowing the embryo to grow to adulthood. Mutagenized founder animals will then be crossed in a traditional F2 screen crossing design. F3 embryos will be screened and separated by phenotype for mapping using RNA-seq and our genetic mapping program MMAPPR.

Create a Cas9 mRNA that is Sequestered to the PGCs

Current mutagenesis protocols treat adult males with N-ethyl-N-nitrosourea (ENU), leading to widespread toxicity and mutagenesis in the animal. This limits the number of mutations that can be generated. CRISPR-Cas9 injections also have limited mutagenic load potential, as they often lead to phenotypes in the embryo itself and injection of small libraries leads to multiple phenotypes in the same embryo. Thus, injection of our library at high concentrations is likely to cause deleterious phenotypes in the embryo, creating a selection bias toward founder animals where the mutation rate is low. As germline mutations are the only mutations of interest in an F2 forward genetic screen, we will create a Cas9 mRNA variant that is sequestered to the primordial germ cell (PGC) lineage. This will result in Cas9-mediated mutation only in the developing gonad. The majority of the embryo will not be affected, increasing survivability of embryos under high mutagenic loads and, subsequently, increasing the number of novel mutations identified per cross.

Cas9 sequestration to the PGC lineage will be accomplished by ligating the nos3 (formerly nos1) 3' UTR to the Cas9 mRNA. Ligation of the nos3 3' UTR to GFP mRNA leads to sequestration of the mRNA and subsequent GFP protein translation only in the PGC lineage. We have created an expression plasmid containing the T7 promoter, the Cas9 coding sequence and the nos3 3'UTR and confirmed proper insertion by Sanger sequencing (data not shown). This plasmid will be linearized, transcribed, and poly-adenylated (mMessage mMachine T7 Ultra kit, Thermo Fisher) to create a PGC-specific Cas9 mRNA.

To test the specificity and efficacy of the PGC-specific Cas9, embryos will be injected with the PGC-specific Cas9 mRNA and a gRNA targeted to the tyr gene, which is essential for pigment formation in the zebrafish embryo (Jao et al. 2013). We have synthesized and injected one-cell zebrafish embryos with this guide RNA and found >80% loss of pigment in the injected embryos (FIG. 3). PGC-specific Cas9 mRNA with the tyr gRNA will be injected at the single-cell stage and embryos assessed for pigment. Controls using standard Cas9 mRNA or no Cas9 mRNA will also be performed. Embryos will then be grown to adulthood and outcrossed to identify germline transmission of mutations in the tyr gene by PCR genotyping the embryos. We expect that the PGC-specific Cas9 will show little to no pigment loss in F0 embryos compared to controls, but will have a high mutation rate in the offspring, indicating high specificity and activity of the PGC-specific Cas9.

Conduct Forward Genetic Screens for Heart Defects in Zebrafish

Figure 7:
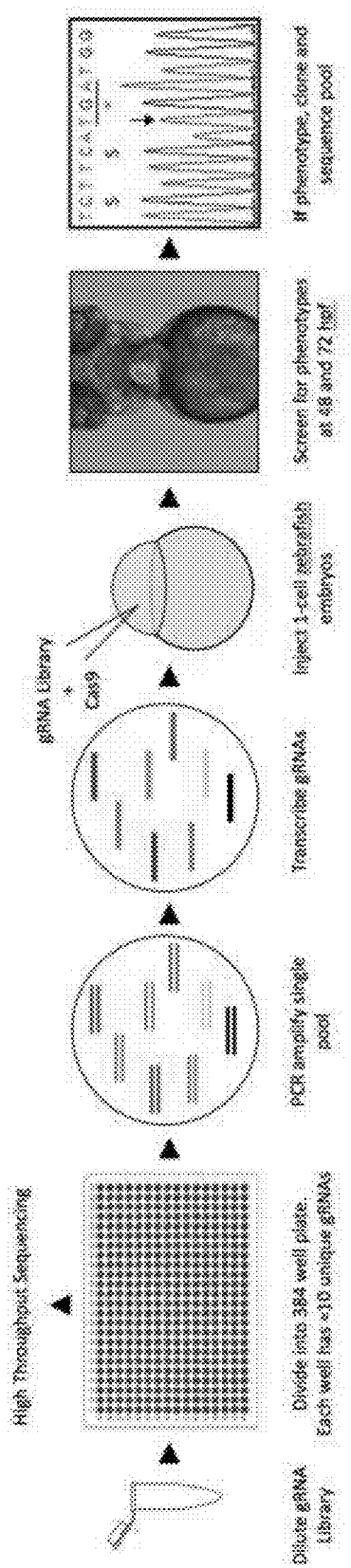
FIG. 7 shows an example F0 screening approach for a gRNA library generated according to the methods and systems of various embodiments.

The library generated according to the methods and systems of various embodiments will be used for an F0 forward genetic screen (FIG. 7). Somewhat analogous to this technique are reverse genetic screens, which involve the injection of small sets of individually chosen and synthesized gRNAs, followed by phenotypic screening and determination of the gRNA causing the phenotype. In the screen proposed here, we will expand this concept to a diverse and unbiased screen using many small pools of our gRNA library to screen for phenotypes in F0 embryos.

To conduct the screen, we will dilute and divide the heart-specific gRNA library to create pools of 10-20 gRNA templates. The appropriate number of pools will be determined from our library sequencing results conducted in phase 1, but is expected to be 300 to 500 pools. Each well will then be PCR amplified using primers to the T7 promoter and sgRNA regions common to all of the gRNA templates in our library, and the PCR products divided into two samples. The first sample will be prepared for sequencing by attaching a unique barcode for each well and then sequenced by illumina sequencing at the BYU DNA sequencing center to identify the gRNA templates contained in each pool. This sequencing will also be used to confirm the complexity of the library as described in aim 1. The remaining gRNA template sample will be transcribed in vitro and co-injected into ~50 cm1c2:GFP embryos with Cas9 (cm1c2:GFP fluorescently labels the heart to increase visibility under the microscope. Injected embryos will be screened for the following phenotypes at 48 and 72 hpf: heart looping (absence or reversal), atrio-ventricular canal (absence and changed diameter), valve formation (presence of blood regurgitation), chamber size, and heart contraction (absence or irregularities). All of these phenotypes are readily seen in the zebrafish embryo under a microscope, allowing rapid screening by visual inspection. The genotypes of the fish for each of the gRNA targets in the pool will then be assessed using the web program PolyPeakParser, which we created to decipher INDELs following genome editing with CRISPR-Cas9. Positive hits will be confirmed by injecting individual gRNAs from the pool. The number of pools screened per gene identified will be used to estimate the efficiency of the gRNA library protocol. This method is advantageous because screening is relatively rapid, as there is no need to create multiple generations for genetic mapping. It is also completely scalable. Labs utilizing this method can work through the gRNA pools without having to maintain large animal colonies.

F2 Forward Genetic Screen

Figure 8:
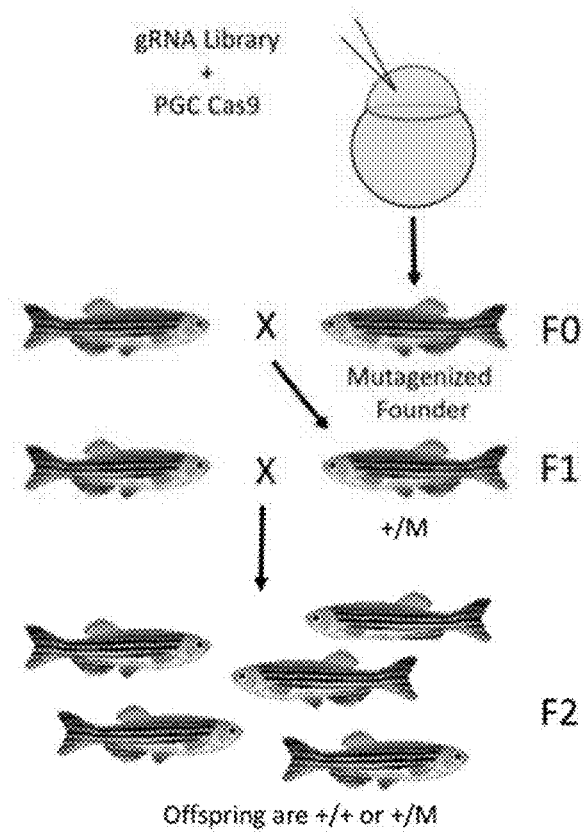
FIG. 8 shows an example F2 screening approach for a gRNA library generated according to the methods and systems of various embodiments.

Although F0 screens are more rapid, they are highly dependent on the percentage of cells mutated following embryo injection, potentially limiting the phenotypes seen. Thus, we will also test the gRNA library using an F2 screen approach (outlined in FIG. 8). To maximize the number of unique mutations in the germline of the founder animal, the PGC-specific Cas9 mRNA created in aim 1b will be co-injected into one-cell zebrafish embryos (Wik line) with the gRNA library. The amount of library and Cas9 mRNA will initially be determined based on the tyrosinase mutagenesis test described above. The optimal amount for a complex library will then be determined by titrating the injection amount and measuring the lethality in the embryos. The optimal amount will be taken to be the maximum amount injected without causing widespread lethality/infertility.

Injected fish will be raised to adulthood and outcrossed to fish from the AB line (a distinct wild-type genetic background). A total of 30-50 F1 progeny will be created from each founder, and these will be outcrossed again to a line specifically expressing GFP in the heart (the cm1c2:GFP line maintained on an AB background) to increase visibility. The resulting F2 families will be in-crossed and their clutches of offspring examined for defects at 48 hpf and 72 hpf. Screening of the embryos will be done by live imaging of the embryos under a microscope for the same phenotypes listed in the F0 screen above. Embryos not expressing GFP (approximately ¼ of offspring) will be excluded from analysis. As zebrafish clutches are fairly large, and the mutations expected to segregate independently from GFP, this should not limit our analysis.

Upon identification of clutches showing Mendelian segregation of one or more cardiovascular phenotypes, embryos will be divided into two pools based on presence/absence of the phenotype, hearts removed, and RNA extracted as described above. The extracted RNA will be used to genetically map the mutations using RNA-seq and the MMAPPR program we have created and previously used to genetically map loci involved in cardiovascular development. MMAPPR is able to map a mutation and generate candidate loci within the linked region in less than one day after RNA-seq data is returned from the sequencing core, greatly increasing the throughput of our screen. A stable line will also be established for future mechanistic studies. The number of families screened and the number of identified phenotypes will be used to determine the efficiency of this protocol for identifying novel genes.

Results and Alternative Approaches

We expect that this project will demonstrate the improved efficiency and ease of using tissue-specific gRNA libraries in a forward genetic screen and provide several novel mutants that we will characterize in future studies. We do not expect difficulties creating the gRNA library, as we have demonstrated the efficacy of our cDNA normalization protocol, and enzymatic generation of gRNA libraries has been published. Furthermore, appropriate gRNA binding sites appear in the genome on average every 16 bases. Thus, we expect that even incomplete coverage of all possible CRISPR gRNA target sites in the library will result in multiple gRNAs to the vast majority of genes contained in the cDNA library, resulting in a complex library theoretically capable of saturating the genes involved in heart development. Indeed, bioinformatic analysis in my lab has found >90% of zebrafish genes longer than 100 base pairs contain at least one potential target site based on the restriction enzymes we will use to generate the library (data not shown). This library will largely be unbiased towards high expressing genes due to the normalization of the cDNA library, but will be slightly biased towards longer genes. This bias, however, is not expected to be strong enough to skew the genes identified from the screen. Creating the library will also result in some gRNAs that are not functional because they bridge exon boundaries. However, this will be a small percentage of the gRNAs, and there will be many others in the library targeting the same genes.

Using the nos3 3' UTR to sequester and translate RNA specifically in the primordial germ cells has been demonstrated previously using GFP. However, it remains possible that sequestration will not work appropriately with Cas9 mRNA. If this occurs, creation of a Cas9 transgene under the control of the vasa 3' UTR or a transgenic approach using the kop promoter and nanos3 3' UTR will be considered. Both of these methods have also been shown to drive PGC-specific expression. It is also unknown how stable the gRNAs will be in the embryo, as they will not be bound by Cas9 until it is translated in the PGCs several hours later. If stability is an issue, then we will clone the library into U6 promoter containing plasmids, allowing episomal and/or transgenic expression of the gRNA during early development.

There is a potential risk of off-target mutagenesis when using CRISPR-Cas9 techniques. However, an analysis of on-target and off-target mutation frequencies in the K562 cell line showed that, while on target mutation frequencies approached 100%, off-target mutations were seen in less than 1% of cells. Therefore, off-target mutations are extremely unlikely to create an observable phenotype in the F0 screen. However, if the phenotype cannot be linked to a particular target in our CRISPR pool, we will leverage my lab's bioinformatic expertise to search for all potential off-target sites containing 0, 1 or 2 mismatches. We will then test potential off-target sites for association with the phenotype. In the F2 screen, rare mutations could be created in the mutagenized animals and inherited in 100% of cells in the resulting offspring, thus creating an observable phenotype. However, in the F2 screen we will use a MMAPPR-based genomic approach to map the mutation using linkage disequilibrium. One of the advantages of the MMAPPR protocol is that it does not rely on the content of the CRISPR-library. Therefore, mutations will be able to be genetically mapped regardless of whether they are caused by on-target or off-target CRISPR activity.

The central question of this proposal is whether mutagenizing with gRNA libraries will result in more efficient identification of novel genes involved in heart development. This efficiency will depend on the mutagenesis rate in the two forward genetics strategies—F0 and F2 screens—tested here. For this reason, we have designed ways to optimize the concentrations of the Cas9 mRNA/protein and library injected into the zebrafish embryos. This optimization will maximize the efficiency of the screen and will serve as a guide for future screens implementing this method.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A polynucleotide comprising: a sequence encoding for a constant region comprising a protein binding segment of an RNA component of a CRISPR complex, the sequence comprising: a non-palindromic recognition sequence for a type restriction enzyme configured to cleave at least 17 nucleotides outside of the non-palindromic recognition sequence, the non-palindromic recognition sequence being oriented such that, in the presence of the type restriction enzyme, a DNA cleavage domain of the type II restriction enzyme is positioned outside of the constant region.

2. The polynucleotide of claim 1, wherein the polynucleotide is double-stranded with sense and antisense strands and the non-palindromic recognition sequence is oriented that, when in the presence of the type II restriction enzyme, the DNA cleavage domain of the type restriction enzyme is positioned at one of: a first location upstream from a 5' end of the sense strand and a second location downstream from a 3' end of the sense strand.

3. The polynucleotide of claim 1, wherein the encoded constant region comprising the non-palindromic recognition sequence is configured to be incorporated within a secondary structure of the RNA component of the CRISPR complex.

4. The polynucleotide of claim 1, further comprising a second sequence capable of hybridizing to the non-palindromic recognition sequence.

5. The polynucleotide of claim 4, wherein the encoded constant region comprising the non-palindromic recognition sequence and the second sequence hybridize to form a secondary structure of the constant region.

6. The polynucleotide of claim 1, wherein the polynucleotide is double-stranded and further comprises a modification selected from at least one modified sugar moiety, at least one modified internucleotide linkage, at least one modified nucleotide, and combinations thereof.

7. The polynucleotide of claim 6, wherein the at least one modified internucleotide linkage is selected from the group of phosphorothioate, alkylphosphonate, phosphorodithioate, alkylphosphonothioate, phosphoramidate, carbamate, carbonate, phosphate triester, acetamidate, carboxymethyl ester, and combinations thereof.

8. The polynucleotide of claim 1, wherein the non-palindromic recognition sequence is capable of binding to at least one type H restriction enzyme selected from the group consisting of NmeAIII, MmeI, CstMI, EcoP15I, ApyPI, AquII, AquIII, AquIV, CdpI, CstMI, DraRI, DrdIV, EsaSSI, MaqI, NhaXI, N1aCI, PlaDI, PspOMII, PspPRI, RceI, RpaB5I, SdeAI, SpoDI, BsbI, and combinations thereof.

9. The polynucleotide of claim 1, wherein the polynucleotide is operably linked to a second polynucleotide, wherein, when in the presence of the type restriction enzyme, the second polynucleotide is cleaved at least 17 nucleotides from the non-palindromic recognition sequence.

10. The polynucleotide of claim 9, wherein cleavage by the type II restriction enzyme generates a variable region, wherein the variable region comprises a DNA hybridizing segment of the RNA component of the CRISPR complex.

11. The polynucleotide of claim 10, operably linked to a third polynucleotide comprising a promoter sequence recognized by an RNA polymerase, wherein the promoter is capable of directing the RNA polymerase to transcribe the RNA component of the CRISPR complex.

12. A kit for generating CRISPR guide RNA (gRNA) libraries comprising a polynucleotide comprising: a sequence encoding for a constant region comprising a protein binding segment of an RNA component of a CRISPR complex, the constant region comprising: a non-palindromic recognition sequence for a type II restriction enzyme configured to cleave at least 17 nucleotides outside of the non-palindromic recognition sequence, the non-palindromic recognition sequence being oriented that, when in the presence of the type II restriction enzyme, a DNA cleavage domain of the type II restriction enzyme is positioned outside of the constant region.

13. The kit of claim 12 further comprising the type II restriction enzyme.

14. The kit of claim 13, wherein the type H restriction enzyme is selected from the group consisting of NmeAIII, MmeI, CstMI, EcoP15I, ApyPI, AquII, AquIII, AquIV, CdpI, CstMI, DraRI, DrdIV, EsaSSI, MaqI, NhaXI, N1aCI, PlaDI, PspOMII, PspPRI, RceI, RpaB5I, SdeAI, SpoDI, BsbI, and combinations thereof.

15. The kit of claim 12 further comprising a solid support capable of immobilizing the polynucleotide to a surface of the sod support by chemical attachment, high binding affinity or oligonucleotide hybridization.

16. The kit of claim 12 further comprising a promoter polynucleotide recognized by an RNA polymerase.

* * * * *

```
                           SEQUENCE LISTING

<160> NUMBER OF SEQ ID NOS: 453

<210> SEQ ID NO 1
<211> LENGTH: 81
<212> TYPE: DNA
<213> ORGANISM: Streptococcus pyogenes

<400> SEQUENCE: 1
gttttagagc tagaaatagc aagttaaaat aaggctagtc cgttatcaac ttgaaaaagt    60
ggcaccgagt cggtgctttt t                                              81

<210> SEQ ID NO 2
<211> LENGTH: 81
<212> TYPE: DNA
<213> ORGANISM: Streptococcus pyogenes

<400> SEQUENCE: 2
aaaaagcacc gactcggtgc cacttttca agttgataac ggactagcct tattttaact    60
tgctatttct agctctaaaa c                                              81

<210> SEQ ID NO 3
<211> LENGTH: 81
<212> TYPE: RNA
<213> ORGANISM: Streptococcus pyogenes

<400> SEQUENCE: 3
guuuuagagc uagaaauagc aaguuaaaau aaggcuaguc cguuaucaac uugaaaaagu    60
ggcaccgagu cggugcuuuu u                                              81

<210> SEQ ID NO 4
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 4
gtyggagagc tagaaatagc aagttccaat aaggctagtc cgttatcaac ttgaaaaagt    60
ggcaccgagt cggtgctttt t                                              81

<210> SEQ ID NO 5
<211> LENGTH: 81
<212> TYPE: DNA
<213> ORGANISM: Artificial
```

```
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 5
aaaaagcacc gactcggtgc cacttttca agttgataac ggactagcct tattggaact    60
tgctatttct agctctccra c                                              81

<210> SEQ ID NO 6
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 6
nnnnnnnnnn nnnnnnnnnn gtyggagagc tagaaatagc aagttccaat aaggctagtc    60
cgttatcaac ttgaaaaagt ggcaccgagt cggtgctttt t                       101

<210> SEQ ID NO 7
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 7
aaaaagcacc gactcggtgc cacttttca agttgataac ggactagcct tattggaact    60
tgctatttct agctctccra cnnnnnnnnn nnnnnnnnnn n                       101

<210> SEQ ID NO 8
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 8
nnnnnnnnnn nnnnnnnnnn guyggagagc uagaaauagc aaguuccaau aaggcuaguc    60
cguuaucaac uugaaaaagu ggcaccgagu cggugcuuuu u                       101
```

<210> SEQ ID NO 9
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 9
ggtyggaagc tagaaatagc aagtccaact aaggctagtc cgttatcaac ttgaaaaagt     60
ggcaccgagt cggtgctttt t                                               81

<210> SEQ ID NO 10
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 10
aaaaagcacc gactcggtgc cactttttca agttgataac ggactagcct tagttggact     60
tgctatttct agcttccrac c                                               81

<210> SEQ ID NO 11
<211> LENGTH: 100
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 11
nnnnnnnnnn nnnnnnnnng gtyggaagct agaaatagca agtccaacta aggctagtcc     60
gttatcaact tgaaaaagtg gcaccgagtc ggtgcttttt                          100

<210> SEQ ID NO 12
<211> LENGTH: 100
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(100)
<223> OTHER INFORMATION: n is a, c, g, or t

<400> SEQUENCE: 12
aaaaagcacc gactcggtgc cactttttca agttgataac ggactagcct tagttggact     60
tgctatttct agcttccrac cnnnnnnnnn nnnnnnnnn                           100

<210> SEQ ID NO 13
<211> LENGTH: 100
<212> TYPE: RNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (1)..(19)
<223> OTHER INFORMATION: n is a, c, g, or u

<400> SEQUENCE: 13
nnnnnnnnnn nnnnnnnnng guyggaagcu agaaauagca aguccaacua aggcuagucc    60
guuaucaacu ugaaaaagug gcaccgaguc ggugcuuuuu                         100

<210> SEQ ID NO 14
<211> LENGTH: 81
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.

<400> SEQUENCE: 14
gtgtyggagc tagaaatagc aagtcaacat aaggctagtc cgttatcaac ttgaaaaagt    60
ggcaccgagt cggtgctttt t                                              81

<210> SEQ ID NO 15
<211> LENGTH: 81
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.

<400> SEQUENCE: 15
aaaaagcacc gactcggtgc cacttttca agttgataac ggactagcct tatgttgact    60
tgctatttct agctccraca c                                              81

<210> SEQ ID NO 16
<211> LENGTH: 99
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 16
nnnnnnnnnn nnnnnnnngt gtyggagcta gaaatagcaa gtcaacataa ggctagtccg    60
ttatcaactt gaaaaagtgg caccgagtcg gtgcttttt                                    99

<210> SEQ ID NO 17
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(99)
<223> OTHER INFORMATION: n is a, c, g, or t

<400> SEQUENCE: 17
aaaaagcacc gactcggtgc cactttttca agttgataac ggactagcct tatgttgact            60
tgctatttct agctccraca cnnnnnnnnn nnnnnnnnn                                   99

<210> SEQ ID NO 18
<211> LENGTH: 99
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or u

<400> SEQUENCE: 18
nnnnnnnnnn nnnnnnnngu guyggagcua gaaauagcaa gucaacauaa ggcuaguccg            60
uuaucaacuu gaaaaagugg caccgagucg gugcuuuuu                                   99

<210> SEQ ID NO 19
<211> LENGTH: 82
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 19
ccggtyggag ctagaaatag caagtcaacc taaggctagt ccgttatcaa cttgaaaaag            60
tggcaccgag tcggtgcttt tt                                                    82

<210> SEQ ID NO 20
<211> LENGTH: 82
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 20
aaaaagcacc gactcggtgc cactttttca agttgataac ggactagcct taggttgact            60
tgctatttct agctccracc gg         82

<210> SEQ ID NO 21
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 21
nnnnnnnnnn nnnnnnnncg gtyggagcta gaaatagcaa gtcaacctaa ggctagtccg    60
ttatcaactt gaaaaagtgg caccgagtcg gtgcttttt    99

<210> SEQ ID NO 22
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(99)
<223> OTHER INFORMATION: n is a, c, g, or t

<400> SEQUENCE: 22
aaaaagcacc gactcggtgc cacttttca agttgataac ggactagcct taggttgact    60
tgctatttct agctccracc gnnnnnnnnn nnnnnnnnn    99

<210> SEQ ID NO 23
<211> LENGTH: 99
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or u

<400> SEQUENCE: 23
nnnnnnnnnn nnnnnnnncg guyggagcua gaaauagcaa gucaaccuaa ggcuaguccg    60
uuaucaacuu gaaaaagugg caccgagucg gugcuuuuu    99

<210> SEQ ID NO 24
<211> LENGTH: 83
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or sgRNA or crRNA.
<220> FEATURE:
<221> NAME/KEY: misc_feature
<222> LOCATION: (3)..(3)
<223> OTHER INFORMATION: n is a, c, g, or t

<400> SEQUENCE: 24
ccnggtygga gctagaaata gcaagtcaac ctaaggctag tccgttatca acttgaaaaa    60
gtggcaccga gtcggtgctt ttt                                           83

<210> SEQ ID NO 25
<211> LENGTH: 83
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (81)..(81)
<223> OTHER INFORMATION: n is a, c, g, or t

<400> SEQUENCE: 25
aaaaagcacc gactcggtgc cacttttttca agttgataac ggactagcct taggttgact    60
tgctatttct agctccracc ngg                                            83

<210> SEQ ID NO 26
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 26
nnnnnnnnnn nnnnnnnnng gtyggagcta gaaatagcaa gtcaacctaa ggctagtccg    60
ttatcaactt gaaaaagtgg caccgagtcg gtgcttttt                           99

<210> SEQ ID NO 27
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (81)..(99)
<223> OTHER INFORMATION: n is a, c, g, or t

<400> SEQUENCE: 27
aaaaagcacc gactcggtgc cacttttttca agttgataac ggactagcct taggttgact    60
tgctatttct agctccracc nnnnnnnnnn nnnnnnnnn                           99

```
<210> SEQ ID NO 28
<211> LENGTH: 99
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or u

<400> SEQUENCE: 28
nnnnnnnnnn nnnnnnnnng guyggagcua gaaauagcaa gucaaccuaa ggcuaguccg    60
uuaucaacuu gaaaaagugg caccgagucg gugcuuuuu                          99

<210> SEQ ID NO 29
<211> LENGTH: 82
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 29
ctagtyggag ctagaaatag caagtcaacc taaggctagt ccgttatcaa cttgaaaaag    60
tggcaccgag tcggtgcttt tt                                            82

<210> SEQ ID NO 30
<211> LENGTH: 82
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 30
aaaaagcacc gactcggtgc cacttttttca agttgataac ggactagcct taggttgact   60
tgctatttct agctccract ag                                            82

<210> SEQ ID NO 31
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 31
nnnnnnnnnn nnnnnnnnta gtyggagcta gaaatagcaa gtcaacctaa ggctagtccg    60
ttatcaactt gaaaaagtgg caccgagtcg gtgcttttt                          99
```

<210> SEQ ID NO 32
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(99)
<223> OTHER INFORMATION: n is a, c, g, or t

<400> SEQUENCE: 32
aaaaagcacc gactcggtgc cacttttcta agttgataac ggactagcct taggttgact    60
tgctatttct agctccract annnnnnnnn nnnnnnnnn                           99

<210> SEQ ID NO 33
<211> LENGTH: 99
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or u

<400> SEQUENCE: 33
nnnnnnnnnn nnnnnnnnua guyggagcua gaaauagcaa gucaaccuaa ggcuaguccg    60
uuaucaacuu gaaaaagugg caccgagucg gugcuuuuu                           99

<210> SEQ ID NO 34
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 34
ctcggcgagc tagaaatagc aagtgccgat aaggctagtc cgttatcaac ttgaaaaagt    60
ggcaccgagt cggtgctttt t                                              81

<210> SEQ ID NO 35
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 35
aaaaagcacc gactcggtgc cacttttcta agttgataac ggactagcct tatcggcact    60
tgctatttct agctcgccga g                                              81

```
<210> SEQ ID NO 36
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 36
nnnnnnnnnn nnnnnnnnnn ctcggcgagc tagaaatagc aagtgccgat aaggctagtc      60
cgttatcaac ttgaaaaagt ggcaccgagt cggtgctttt t                        101

<210> SEQ ID NO 37
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 37
aaaaagcacc gactcggtgc cacttttttca gttgataac ggactagcct tatcggcact      60
tgctatttct agctcgccga gnnnnnnnnn nnnnnnnnnn n                        101

<210> SEQ ID NO 38
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 38
nnnnnnnnnn nnnnnnnnnn cucggcgagc uagaaauagc aagugccgau aaggcuaguc      60
cguuaucaac uugaaaaagu ggcaccgagu cggugcuuuu u                        101

<210> SEQ ID NO 39
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
```

<400> SEQUENCE: 39
gctcggcagc tagaaatagc aagtccgagt aaggctagtc cgttatcaac ttgaaaaagt    60
ggcaccgagt cggtgctttt t                                              81

<210> SEQ ID NO 40
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 40
aaaaagcacc gactcggtgc cacttttca agttgataac ggactagcct tactcggact     60
tgctatttct agctgccgag c                                              81

<210> SEQ ID NO 41
<211> LENGTH: 100
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 41
nnnnnnnnnn nnnnnnnnng ctcggcagct agaaatagca agtccgagta aggctagtcc    60
gttatcaact tgaaaaagtg gcaccgagtc ggtgctttt                          100

<210> SEQ ID NO 42
<211> LENGTH: 100
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(100)
<223> OTHER INFORMATION: n is a, c, g, or t

<400> SEQUENCE: 42
aaaaagcacc gactcggtgc cacttttca agttgataac ggactagcct tactcggact     60
tgctatttct agctgccgag cnnnnnnnnn nnnnnnnnn                          100

<210> SEQ ID NO 43
<211> LENGTH: 100
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

```
<220> FEATURE:
<221> NAME/KEY: misc_feature
<222> LOCATION: (1)..(19)
<223> OTHER INFORMATION: n is a, c, g, or u

<400> SEQUENCE: 43
nnnnnnnnnn nnnnnnnnng cucggcagcu agaaauagca aguccgagua aggcuagucc      60
guuaucaacu ugaaaaagug gcaccgaguc ggugcuuuuu                           100

<210> SEQ ID NO 44
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 44
gtctcggcgc tagaaatagc aagtcgagat aaggctagtc cgttatcaac ttgaaaaagt      60
ggcaccgagt cggtgctttt t                                                81

<210> SEQ ID NO 45
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 45
aaaaagcacc gactcggtgc cacttttca agttgataac ggactagcct tatctcgact       60
tgctatttct agcgccgaga c                                                81

<210> SEQ ID NO 46
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 46
nnnnnnnnnn nnnnnnnngt ctcggcgcta gaaatagcaa gtcgagataa ggctagtccg      60
ttatcaactt gaaaaagtgg caccgagtcg gtgctttt                              99

<210> SEQ ID NO 47
<211> LENGTH: 99
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
```

```
      sgRNA or crRNA.
<220> FEATURE:
<221> NAME/KEY: misc_feature
<222> LOCATION: (82)..(99)
<223> OTHER INFORMATION: n is a, c, g, or t

<400> SEQUENCE: 47
aaaaagcacc gactcggtgc cacttttca agttgataac ggactagcct tatctcgact        60
tgctatttct agcgccgaga cnnnnnnnnn nnnnnnnnn                              99

<210> SEQ ID NO 48
<211> LENGTH: 99
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or u

<400> SEQUENCE: 48
nnnnnnnnnn nnnnnnnngu cucggcgcua gaaauagcaa gucgagauaa ggcuaguccg        60
uuaucaacuu gaaaaagugg caccgagucg gugcuuuuu                              99

<210> SEQ ID NO 49
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 49
gtcgatgagc tagaaatagc aagtatcgat aaggctagtc cgttatcaac ttgaaaaagt        60
ggcaccgagt cggtgctttt t                                                 81

<210> SEQ ID NO 50
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 50
aaaaagcacc gactcggtgc cacttttca agttgataac ggactagcct tatcgatact        60
tgctatttct agctcatcga c                                                 81

<210> SEQ ID NO 51
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
``` and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 51
nnnnnnnnnn nnnnnnnnnn gtcgatgagc tagaaatagc aagtatcgat aaggctagtc    60
cgttatcaac ttgaaaaagt ggcaccgagt cggtgctttt t                       101

<210> SEQ ID NO 52
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with
      non-palindromic recognition site for restriction enzyme (sense or
      antisense), polynucleotide encoding for constant and variable
      regions of sgRNA or crRNA (sense or antisense), or sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 52
aaaaagcacc gactcggtgc cacttttca agttgataac ggactagcct tatcgatact     60
tgctatttct agctcatcga cnnnnnnnnn nnnnnnnnnn n                       101

<210> SEQ ID NO 53
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 53
nnnnnnnnnn nnnnnnnnnn gucgaugagc uagaaauagc aaguaucgau aaggcuaguc    60
cguuaucaac uugaaaaagu ggcaccgagu cggugcuuuu u                       101

<210> SEQ ID NO 54
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 54

```
gtncggcagc tagaaatagc aaggccgnat aaggctagtc cgttatcaac ttgaaaaagt    60
ggcaccgagt cggtgctttt t                                              81

<210> SEQ ID NO 55
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 55
aaaaagcacc gactcggtgc cacttttcca gttgataac ggactagcct tatncggcct    60
tgctatttct agctgccgna c                                              81

<210> SEQ ID NO 56
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 56
nnnnnnnnnn nnnnnnnnnn gtncggcagc tagaaatagc aaggccgnat aaggctagtc    60
cgttatcaac ttgaaaaagt ggcaccgagt cggtgctttt t                       101

<210> SEQ ID NO 57
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
```

```
<220> FEATURE:
<221> NAME/KEY: misc_feature
<222> LOCATION: (82)..(101)
<223> OTHER INFORMATION: n is a, c, g, or t

<400> SEQUENCE: 57
aaaaagcacc gactcggtgc cacttttttca agttgataac ggactagcct tatncggcct      60
tgctatttct agctgccgna cnnnnnnnnn nnnnnnnnnn n                           101

<210> SEQ ID NO 58
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (48)..(48)
<223> OTHER INFORMATION: n is a, c, g, or u

<400> SEQUENCE: 58
nnnnnnnnnn nnnnnnnnnn guncggcagc uagaaauagc aaggccgnau aaggcuaguc      60
cguuaucaac uugaaaaagu ggcaccgagu cggugcuuuu u                          101

<210> SEQ ID NO 59
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 59
ctcctcgagc tagaaatagc aagtgaggat aaggctagtc cgttatcaac ttgaaaaagt      60
ggcaccgagt cggtgctttt t                                                81

<210> SEQ ID NO 60
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 60
aaaaagcacc gactcggtgc cacttttttca agttgataac ggactagcct tatcctcact     60
tgctatttct agctcgagga g                                                81

<210> SEQ ID NO 61
```

```
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 61
nnnnnnnnnn nnnnnnnnnn ctcctcgagc tagaaatagc aagtgaggat aaggctagtc    60
cgttatcaac ttgaaaaagt ggcaccgagt cggtgctttt t                       101

<210> SEQ ID NO 62
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 62
aaaaagcacc gactcggtgc cacttttca agttgataac ggactagcct tatcctcact    60
tgctatttct agctcgagga gnnnnnnnnn nnnnnnnnnn n                       101

<210> SEQ ID NO 63
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 63
nnnnnnnnnn nnnnnnnnnn cuccucgagc uagaaauagc aagugaggau aaggcuaguc    60
cguuaucaac uugaaaaagu ggcaccgagu cggugcuuuu u                       101

<210> SEQ ID NO 64
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 64
cttccycagc tagaaatagc aaggrggaat aaggctagtc cgttatcaac ttgaaaaagt    60
```
ggcaccgagt cggtgctttt t         81

<210> SEQ ID NO 65
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 65
aaaaagcacc gactcggtgc cacttttca agttgataac ggactagcct tattccycct    60
tgctatttct agctgrggaa g          81

<210> SEQ ID NO 66
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable
      regions of sgRNA or crRNA (sense or antisense), or sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 66
nnnnnnnnnn nnnnnnnnnn cttccycagc tagaaatagc aaggrggaat aaggctagtc    60
cgttatcaac ttgaaaaagt ggcaccgagt cggtgctttt t                       101

<210> SEQ ID NO 67
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 67
aaaaagcacc gactcggtgc cacttttca agttgataac ggactagcct tattccycct    60
tgctatttct agctgrggaa gnnnnnnnnn nnnnnnnnnn n                       101

<210> SEQ ID NO 68
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)

<223> OTHER INFORMATION: n is a, c, g, or u

<400> SEQUENCE: 68
nnnnnnnnnn nnnnnnnnnn cuuccycagc uagaaauagc aaggrggaau aaggcuaguc    60
cguuaucaac uugaaaaagu ggcaccgagu cggugcuuuu u    101

<210> SEQ ID NO 69
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 69
ctccgcgagc tagaaatagc aagtgcggat aaggctagtc cgttatcaac ttgaaaaagt    60
ggcaccgagt cggtgctttt t    81

<210> SEQ ID NO 70
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 70
aaaaagcacc gactcggtgc cactttttca agttgataac ggactagcct tatccgcact    60
tgctatttct agctcgcgga g    81

<210> SEQ ID NO 71
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 71
nnnnnnnnnn nnnnnnnnnn ctccgcgagc tagaaatagc aagtgcggat aaggctagtc    60
cgttatcaac ttgaaaaagt ggcaccgagt cggtgctttt t    101

<210> SEQ ID NO 72
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature

```
<222> LOCATION: (82)..(101)
<223> OTHER INFORMATION: n is a, c, g, or t

<400> SEQUENCE: 72
aaaaagcacc gactcggtgc cacttttcca gttgataac ggactagcct tatccgcact    60
tgctatttct agctcgcgga gnnnnnnnnn nnnnnnnnnn n                       101

<210> SEQ ID NO 73
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 73
nnnnnnnnnn nnnnnnnnnn cuccgcgagc uagaaauagc aagugcggau aaggcuaguc    60
cguuaucaac uugaaaaagu ggcaccgagu cggugcuuuu u                       101

<210> SEQ ID NO 74
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 74
ctccttgagc tagaaatagc aagtaaggat aaggctagtc cgttatcaac ttgaaaaagt    60
ggcaccgagt cggtgctttt t                                              81

<210> SEQ ID NO 75
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 75
aaaaagcacc gactcggtgc cacttttcca gttgataac ggactagcct tatccttact    60
tgctatttct agctcaagga g                                              81

<210> SEQ ID NO 76
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
```

```
<221> NAME/KEY: misc_feature
<222> LOCATION: (1)..(20)
<223> OTHER INFORMATION: n is a, c, g, or t

<400> SEQUENCE: 76
nnnnnnnnnn nnnnnnnnnn ctccttgagc tagaaatagc aagtaaggat aaggctagtc      60
cgttatcaac ttgaaaaagt ggcaccgagt cggtgctttt t                         101

<210> SEQ ID NO 77
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 77
aaaaagcacc gactcggtgc cacttttttca agttgataac ggactagcct tatccttact    60
tgctatttct agctcaagga gnnnnnnnnn nnnnnnnnnn n                         101

<210> SEQ ID NO 78
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 78
nnnnnnnnnn nnnnnnnnnn cuccuugagc uagaaauagc aaguaaggau aaggcuaguc     60
cguuaucaac uugaaaaagu ggcaccgagu cggugcuuuu u                         101

<210> SEQ ID NO 79
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 79
gtncttgagc tagaaatagc aagcaagnat aaggctagtc cgttatcaac ttgaaaaagt     60
ggcaccgagt cggtgctttt t                                               81
```

```
<210> SEQ ID NO 80
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 80
aaaaagcacc gactcggtgc cacttttca agttgataac ggactagcct tatncttgct    60
tgctatttct agctcaagna c                                             81

<210> SEQ ID NO 81
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 81
nnnnnnnnnn nnnnnnnnnn gtncttgagc tagaaatagc aagcaagnat aaggctagtc    60
cgttatcaac ttgaaaaagt ggcaccgagt cggtgctttt t                       101

<210> SEQ ID NO 82
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (82)..(101)
```

<223> OTHER INFORMATION: n is a, c, g, or t

<400> SEQUENCE: 82
aaaaagcacc gactcggtgc cacttttca agttgataac ggactagcct tatncttgct    60
tgctatttct agctcaagna cnnnnnnnnn nnnnnnnnnn n                       101

<210> SEQ ID NO 83
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u
<220> FEATURE:
<221> NAME/KEY: misc_feature
<222> LOCATION: (48)..(48)
<223> OTHER INFORMATION: n is a, c, g, or u

<400> SEQUENCE: 83
nnnnnnnnnn nnnnnnnnnn guncuugagc uagaaauagc aagcaagnau aaggcuaguc    60
cguuaucaac uugaaaaagu ggcaccgagu cggugcuuuu u                       101

<210> SEQ ID NO 84
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 84
gtcgtagagc tagaaatagc aagttacgat aaggctagtc cgttatcaac ttgaaaaagt    60
ggcaccgagt cggtgctttt t                                             81

<210> SEQ ID NO 85
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 85
aaaaagcacc gactcggtgc cacttttca agttgataac ggactagcct tatcgtaact     60
tgctatttct agctctacga c                                             81

<210> SEQ ID NO 86
<211> LENGTH: 101
<212> TYPE: DNA
<213> ORGANISM: Artificial

```
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 86
nnnnnnnnnn nnnnnnnnnn gtcgtagagc tagaaatagc aagttacgat aaggctagtc      60
cgttatcaac ttgaaaaagt ggcaccgagt cggtgctttt t                         101

<210> SEQ ID NO 87
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 87
aaaaagcacc gactcggtgc cacttttttca agttgataac ggactagcct tatcgtaact    60
tgctatttct agctctacga cnnnnnnnnn nnnnnnnnnn n                        101

<210> SEQ ID NO 88
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 88
nnnnnnnnnn nnnnnnnnnn gucguagagc uagaaauagc aaguuacgau aaggcuaguc     60
cguuaucaac uugaaaaagu ggcaccgagu cggugcuuuu u                        101

<210> SEQ ID NO 89
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 89
gtggtcgagc tagaaatagc aagtgaccat aaggctagtc cgttatcaac ttgaaaaagt    60
ggcaccgagt cggtgctttt t                                              81
```

<210> SEQ ID NO 90
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 90
aaaaagcacc gactcggtgc cacttttca agttgataac ggactagcct tatggtcact    60
tgctatttct agctcgacca c                                              81

<210> SEQ ID NO 91
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 91
nnnnnnnnnn nnnnnnnnnn gtggtcgagc tagaaatagc aagtgaccat aaggctagtc    60
cgttatcaac ttgaaaaagt ggcaccgagt cggtgctttt t                       101

<210> SEQ ID NO 92
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 92
aaaaagcacc gactcggtgc cactttttca agttgataac ggactagcct tatggtcact   60
tgctatttct agctcgacca cnnnnnnnnn nnnnnnnnnn n                       101

<210> SEQ ID NO 93
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 93
nnnnnnnnnn nnnnnnnnnn guggucgagc uagaaauagc aagugaccau aaggcuaguc    60
cguuaucaac uugaaaaagu ggcaccgagu cggugcuuuu u                       101

<210> SEQ ID NO 94
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 94
gtcaaygagc tagaaatagc aagcrttgat aaggctagtc cgttatcaac ttgaaaaagt   60
ggcaccgagt cggtgctttt t                                             81

<210> SEQ ID NO 95
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 95
aaaaagcacc gactcggtgc cacttttca agttgataac ggactagcct tatcaaygct    60
tgctatttct agctcrttga c                                             81

<210> SEQ ID NO 96
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or
      antisense), polynucleotide encoding for constant and variable
      regions of sgRNA or crRNA (sense or antisense), or sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 96
nnnnnnnnnn nnnnnnnnnn gtcaaygagc tagaaatagc aagcrttgat aaggctagtc   60
cgttatcaac ttgaaaaagt ggcaccgagt cggtgctttt t                      101

<210> SEQ ID NO 97
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 97
aaaaagcacc gactcggtgc cactttttca agttgataac ggactagcct tatcaaygct    60
tgctatttct agctcrttga cnnnnnnnnn nnnnnnnnnn n                        101

<210> SEQ ID NO 98
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 98
nnnnnnnnnn nnnnnnnnnn gucaaygagc uagaaauagc aagcruugau aaggcuaguc    60
cguuaucaac uugaaaaagu ggcaccgagu cggugcuuuu u                        101

<210> SEQ ID NO 99
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 99
ctycttgagc tagaaatagc aagcaagrat aaggctagtc cgttatcaac ttgaaaaagt    60
ggcaccgagt cggtgctttt t                                              81

<210> SEQ ID NO 100
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 100
aaaaagcacc gactcggtgc cactttttca agttgataac ggactagcct tatycttgct    60
tgctatttct agctcaagra g                                              81

<210> SEQ ID NO 101
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 101
nnnnnnnnnn nnnnnnnnnn ctycttgagc tagaaatagc aagcaagrat aaggctagtc    60
cgttatcaac ttgaaaaagt ggcaccgagt cggtgctttt t    101

<210> SEQ ID NO 102
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 102
aaaaagcacc gactcggtgc cacttttttca agttgataac ggactagcct tatycttgct    60
tgctatttct agctcaagra gnnnnnnnnn nnnnnnnnnn n    101

<210> SEQ ID NO 103
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense),
      or sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 103
nnnnnnnnnn nnnnnnnnnn curcuugagc uagaaauagc aagcaagrau aaggcuaguc    60
cguuaucaac uugaaaaagu ggcaccgagu cggugcuuuu u    101

<210> SEQ ID NO 104
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 104
gtgatggagc tagaaatagc aagtcatcat aaggctagtc cgttatcaac ttgaaaaagt    60
ggcaccgagt cggtgctttt t    81

<210> SEQ ID NO 105
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or sgRNA or crRNA.

<400> SEQUENCE: 105
aaaaagcacc gactcggtgc cacttttca agttgataac ggactagcct tatgatgact      60
tgctatttct agctccatca c                                               81

<210> SEQ ID NO 106
<211> LENGTH: 100
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 106
nnnnnnnnnn nnnnnnnnng tgatggagct agaaatagca agtcatcata aggctagtcc      60
gttatcaact tgaaaaagtg gcaccgagtc ggtgcttttt                           100

<210> SEQ ID NO 107
<211> LENGTH: 100
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(100)
<223> OTHER INFORMATION: n is a, c, g, or t

<400> SEQUENCE: 107
aaaaagcacc gactcggtgc cacttttca agttgataac ggactagcct tatgatgact      60
tgctatttct agctccatca cnnnnnnnnn nnnnnnnnnn                          100

<210> SEQ ID NO 108
<211> LENGTH: 100
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or u

<400> SEQUENCE: 108
nnnnnnnnnn nnnnnnnnng ugauggagcu agaaauagca agucaucaua aggcuagucc      60
guuaucaacu ugaaaaagug gcaccgaguc ggugcuuuuu                          100

<210> SEQ ID NO 109
<211> LENGTH: 81
<212> TYPE: DNA
<213> ORGANISM: Artificial

<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 109
ctgatggagc tagaaatagc aagtcatcat aaggctagtc cgttatcaac ttgaaaaagt      60
ggcaccgagt cggtgctttt t                                                81

<210> SEQ ID NO 110
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 110
aaaaagcacc gactcggtgc cacttttttca agttgataac ggactagcct tatgatgact     60
tgctatttct agctccatca g                                                81

<210> SEQ ID NO 111
<211> LENGTH: 102
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(21)
<223> OTHER INFORMATION: n is a, c, g, or t

<400> SEQUENCE: 111
nnnnnnnnnn nnnnnnnnnn nctgatggag ctagaaatag caagtcatca taaggctagt      60
ccgttatcaa cttgaaaaag tggcaccgag tcggtgcttt tt                        102

<210> SEQ ID NO 112
<211> LENGTH: 102
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(102)
<223> OTHER INFORMATION: n is a, c, g, or t

<400> SEQUENCE: 112
aaaaagcacc gactcggtgc cactttttca agttgataac ggactagcct tatgatgact      60
tgctatttct agctccatca gnnnnnnnnn nnnnnnnnnn nn                        102

<210> SEQ ID NO 113
<211> LENGTH: 102
<212> TYPE: RNA

-continued

```
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(21)
<223> OTHER INFORMATION: n is a, c, g, or u

<400> SEQUENCE: 113
nnnnnnnnnn nnnnnnnnnn ncugauggag cuagaaauag caagucauca uaaggcuagu        60
ccguuaucaa cuugaaaaag uggcaccgag ucggugcuuu uu                          102

<210> SEQ ID NO 114
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 114
ytgggcgagc tagaaatagc aagcgcccat aaggctagtc cgttatcaac ttgaaaaagt        60
ggcaccgagt cggtgctttt t                                                  81

<210> SEQ ID NO 115
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 115
aaaaagcacc gactcggtgc cacttttttca agttgataac ggactagcct tatgggcgct       60
tgctatttct agctcgccca r                                                  81

<210> SEQ ID NO 116
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 116
nnnnnnnnnn nnnnnnnnnn ytgggcgagc tagaaatagc aagcgcccat aaggctagtc        60
cgttatcaac ttgaaaaagt ggcaccgagt cggtgctttt t                           101

<210> SEQ ID NO 117
<211> LENGTH: 101
```

```
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 117
aaaaagcacc gactcggtgc cacttttca agttgataac ggactagcct tatgggcgct      60
tgctatttct agctcgccca rnnnnnnnnn nnnnnnnnnn n                        101

<210> SEQ ID NO 118
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 118
nnnnnnnnnn nnnnnnnnnn yugggcgagc uagaaauagc aagcgcccau aaggcuaguc      60
cguuaucaac uugaaaaagu ggcaccgagu cggugcuuuu u                        101

<210> SEQ ID NO 119
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 119
ctgrgggagc tagaaatagc aagtccycat aaggctagtc cgttatcaac ttgaaaaagt      60
ggcaccgagt cggtgctttt t                                               81

<210> SEQ ID NO 120
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 120
aaaaagcacc gactcggtgc cacttttca agttgataac ggactagcct tatgrggact      60
tgctatttct agctcccyca g                                               81

<210> SEQ ID NO 121
```

```
<211> LENGTH: 102
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(21)
<223> OTHER INFORMATION: n is a, c, g, or t

<400> SEQUENCE: 121
nnnnnnnnnn nnnnnnnnnn nctgrgggag ctagaaatag caagtccyca taaggctagt      60
ccgttatcaa cttgaaaaag tggcaccgag tcggtgcttt tt                        102

<210> SEQ ID NO 122
<211> LENGTH: 102
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
and variable
      regions of sgRNA or crRNA (sense or antisense), or sgRNA or crRNA.
<220> FEATURE:
<221> NAME/KEY: misc_feature
<222> LOCATION: (82)..(102)
<223> OTHER INFORMATION: n is a, c, g, or t

<400> SEQUENCE: 122
aaaaagcacc gactcggtgc cacttttca agttgataac ggactagcct tatgrggact       60
tgctatttct agctcccyca gnnnnnnnnn nnnnnnnnnn nn                        102

<210> SEQ ID NO 123
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or  antisense), or
      sgRNA or crRNA.
<220> FEATURE:
<221> NAME/KEY: misc_feature
<222> LOCATION: (1)..(21)
<223> OTHER INFORMATION: n is a, c, g, or u

<400> SEQUENCE: 123
nnnnnnnnnn nnnnnnnnnn ncugrgggag cuagaaauag caagucccau aaggcuaguc      60
cguuaucaac uugaaaaagu ggcaccgagu cggugcuuuu u                        101

<210> SEQ ID NO 124
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 124
gtcgatgagc tagaaatagc aagcatcgat aaggctagtc cgttatcaac ttgaaaaagt      60
```

```
ggcaccgagt cggtgctttt t                                              81

<210> SEQ ID NO 125
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 125
aaaaagcacc gactcggtgc cacttttca agttgataac ggactagcct tatcgatgct    60
tgctatttct agctcatcga c                                              81

<210> SEQ ID NO 126
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 126
nnnnnnnnnn nnnnnnnnnn gtcgatgagc tagaaatagc aagcatcgat aaggctagtc    60
cgttatcaac ttgaaaaagt ggcaccgagt cggtgctttt t                       101

<210> SEQ ID NO 127
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 127
aaaaagcacc gactcggtgc cactttttca agttgataac ggactagcct tatcgatgct    60
tgctatttct agctcatcga cnnnnnnnnn nnnnnnnnnn n                       101

<210> SEQ ID NO 128
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
```

<223> OTHER INFORMATION: n is a, c, g, or u

<400> SEQUENCE: 128
gucgaugagc uagaaauagc aagcaucgau aaggcuaguc cguuaucaac uugaaaaagu    60
ggcaccgagu cggugcuuuu unnnnnnnnn nnnnnnnnnn n                        101

<210> SEQ ID NO 129
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 129
gtccycgagc tagaaatagc aagcgrggat aaggctagtc cgttatcaac ttgaaaaagt    60
ggcaccgagt cggtgctttt t                                              81

<210> SEQ ID NO 130
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 130
aaaaagcacc gactcggtgc cacttttcca agttgataac ggactagcct tatccycgct    60
tgctatttct agctcgrgga c                                              81

<210> SEQ ID NO 131
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 131
nnnnnnnnnn nnnnnnnnnn gtccycgagc tagaaatagc aagcgrggat aaggctagtc    60
cgttatcaac ttgaaaaagt ggcaccgagt cggtgctttt t                        101

<210> SEQ ID NO 132
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature

```
<222> LOCATION: (82)..(101)
<223> OTHER INFORMATION: n is a, c, g, or t

<400> SEQUENCE: 132
aaaaagcacc gactcggtgc cacttttttca agttgataac ggactagcct tatccycgct    60
tgctatttct agctcgrgga cnnnnnnnnn nnnnnnnnnn n                        101

<210> SEQ ID NO 133
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 133
nnnnnnnnnn nnnnnnnnnn guccycgagc uagaaauagc aagcgrggau aaggcuaguc    60
cguuaucaac uugaaaaagu ggcaccgagu cggugcuuuu u                       101

<210> SEQ ID NO 134
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 134
ctyctggagc tagaaatagc aagtcagrat aaggctagtc cgttatcaac ttgaaaaagt    60
ggcaccgagt cggtgctttt t                                              81

<210> SEQ ID NO 135
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 135
aaaaagcacc gactcggtgc cacttttttca agttgataac ggactagcct tatyctgact   60
tgctatttct agctccagra g                                              81

<210> SEQ ID NO 136
<211> LENGTH: 102
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
```

```
<221> NAME/KEY: misc_feature
<222> LOCATION: (1)..(21)
<223> OTHER INFORMATION: n is a, c, g, or t

<400> SEQUENCE: 136
nnnnnnnnnn nnnnnnnnnn nctyctggag ctagaaatag caagtcagra taaggctagt      60
ccgttatcaa cttgaaaaag tggcaccgag tcggtgcttt tt                        102

<210> SEQ ID NO 137
<211> LENGTH: 102
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(102)
<223> OTHER INFORMATION: n is a, c, g, or t

<400> SEQUENCE: 137
aaaaagcacc gactcggtgc cacttttca agttgataac ggactagcct tatyctgact       60
tgctatttct agctccagra gnnnnnnnnn nnnnnnnnnn nn                        102

<210> SEQ ID NO 138
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(21)
<223> OTHER INFORMATION: n is a, c, g, or u

<400> SEQUENCE: 138
nnnnnnnnnn nnnnnnnnnn ncuycuggag cuagaaauag caagucagau aaggcuaguc      60
cguuaucaac uugaaaaagu ggcaccgagu cggugcuuuu u                         101

<210> SEQ ID NO 139
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 139
ctyccgcagc tagaaatagc aaggcggrat aaggctagtc cgttatcaac ttgaaaagt       60 ggcaccgagt cggtgctttt t                                                81

<210> SEQ ID NO 140
<211> LENGTH: 81
<212> TYPE: DNA
<213> ORGANISM: Artificial
<220> FEATURE:
<223> OTHER INFORMATION: Polynucleotide encoding constant region of
``` sgRNA/crRNA with non-palindromic recognition site for restriction
enzyme (sense or antisense), polynucleotide encoding for constant
and variable regions of sgRNA or crRNA (sense or antisense), or
sgRNA or crRNA.

<400> SEQUENCE: 140
aaaaagcacc gactcggtgc cacttttca agttgataac ggactagcct tatyccgcct    60
tgctatttct agctgcggra g    81

<210> SEQ ID NO 141
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 141
nnnnnnnnnn nnnnnnnnnn ctyccgcagc tagaaatagc aaggcggrat aaggctagtc    60
cgttatcaac ttgaaaaagt ggcaccgagt cggtgctttt t    101

<210> SEQ ID NO 142
<211> LENGTH: 101
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(101)
<223> OTHER INFORMATION: n is a, c, g, or t

<400> SEQUENCE: 142
aaaaagcacc gactcggtgc cacttttca agttgataac ggactagcct tatyccgcct    60
tgctatttct agctgcggra gnnnnnnnnn nnnnnnnnnn n    101

<210> SEQ ID NO 143
<211> LENGTH: 101
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or u

<400> SEQUENCE: 143
nnnnnnnnnn nnnnnnnnnn cuyccgcagc uagaaauagc aaggcggrau aaggcuaguc    60
cguuaucaac uugaaaaagu ggcaccgagu cggugcuuuu u    101

<210> SEQ ID NO 144

```
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 144
gtgttggagc tagaaatagc aagtcaacat aaggctagtc cgttatcaac ttgaaaaagt      60
ggcaccgagt cggtgctttt t                                               81

<210> SEQ ID NO 145
<211> LENGTH: 81
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 145
aaaaagcacc gactcggtgc cacttttcca gttgataaca ggactagcct tatgttgact      60
tgctatttct agctccaaca c                                               81

<210> SEQ ID NO 146
<211> LENGTH: 102
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(21)
<223> OTHER INFORMATION: n is a, c, g, or t

<400> SEQUENCE: 146
nnnnnnnnnn nnnnnnnnnn ngtgttggag ctagaaatag caagtcaaca taaggctagt      60
ccgttatcaa cttgaaaaag tggcaccgag tcggtgcttt tt                        102

<210> SEQ ID NO 147
<211> LENGTH: 102
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (82)..(102)
<223> OTHER INFORMATION: n is a, c, g, or t

<400> SEQUENCE: 147
aaaaagcacc gactcggtgc cacttttcca gttgataaca ggactagcct tatgttgact      60
tgctatttct agctccaaca cnnnnnnnnn nnnnnnnnnn nn                        102
```

-continued

```
<210> SEQ ID NO 148
<211> LENGTH: 102
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(21)
<223> OTHER INFORMATION: n is a, c, g, or u

<400> SEQUENCE: 148
nnnnnnnnnn nnnnnnnnnn nguguuggag cuagaaauag caagucaaca uaaggcuagu      60
ccguuaucaa cuugaaaaag uggcaccgag ucggugcuuu uu                        102

<210> SEQ ID NO 149
<211> LENGTH: 19
<212> TYPE: DNA
<213> ORGANISM: Francisella novicida

<400> SEQUENCE: 149 aattt

```
<400> SEQUENCE: 153
agtyggaaca ccaacaatt                                                    19

<210> SEQ ID NO 154
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 154
aattgttggt gttccractn nnnnnnnnn nnnnnnn                                 38

<210> SEQ ID NO 155
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 155
nnnnnnnnnn nnnnnnnna gtyggaacac caacaatt                                38

<210> SEQ ID NO 156
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
enzyme (sense or
      antisense), polynucleotide encoding for constant and variable
      regions of sgRNA or crRNA (sense or antisense), or sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 156
aauuguuggu guuccracun nnnnnnnnn nnnnnnn                                 38

<210> SEQ ID NO 157
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 157
aatttgttgt gtccaacat                                                    19
```

<210> SEQ ID NO 158
<211> LENGTH: 19
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.

<400> SEQUENCE: 158
atgttggaca caacaaatt                                                19

<210> SEQ ID NO 159
<211> LENGTH: 37
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 159
aatttgttgt gtccaacatn nnnnnnnnn nnnnnnn                              37

<210> SEQ ID NO 160
<211> LENGTH: 37
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 160
nnnnnnnnnn nnnnnnnnat gttggacaca acaaatt                             37

<210> SEQ ID NO 161
<211> LENGTH: 37
<212> TYPE: RNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 161
aauuuguugu guccaacaun nnnnnnnnnn nnnnnnn                             37

<210> SEQ ID NO 162

```
<211> LENGTH: 21
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 162
aattgttggt gttccracta t                                              21

<210> SEQ ID NO 163
<211> LENGTH: 21
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 163
atagtyggaa caccaacaat t                                              21

<210> SEQ ID NO 164
<211> LENGTH: 40
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (22)..(40)
<223> OTHER INFORMATION: n is a, c, g, or t

<400> SEQUENCE: 164
aattgttggt gttccracta tnnnnnnnnn nnnnnnnnnn                          40

<210> SEQ ID NO 165
<211> LENGTH: 40
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 165
nnnnnnnnnn nnnnnnnnna tagtyggaac accaacaatt                          40

<210> SEQ ID NO 166
<211> LENGTH: 40
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
``` and variable regions of sgRNA or crRNA (sense or antisense), or
    sgRNA or crRNA.
<220> FEATURE:
<221> NAME/KEY: misc_feature
<222> LOCATION: (22)..(40)
<223> OTHER INFORMATION: n is a, c, g, or u

<400> SEQUENCE: 166
aauuguuggu guuccracua unnnnnnnnn nnnnnnnnnn                            40

<210> SEQ ID NO 167
<211> LENGTH: 19
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.

<400> SEQUENCE: 167
aatttgttgt gtccaacat                                                  19

<210> SEQ ID NO 168
<211> LENGTH: 19
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.

<400> SEQUENCE: 168
atgttggaca caacaaatt                                                  19

<210> SEQ ID NO 169
<211> LENGTH: 37
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 169
aatttgttgt gtccaacatn nnnnnnnnn nnnnnnn                               37

<210> SEQ ID NO 170
<211> LENGTH: 37
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable
    regions of sgRNA or crRNA (sense or antisense), or sgRNA or crRNA.
<220> FEATURE:
<221> NAME/KEY: misc_feature
<222> LOCATION: (1)..(18)
<223> OTHER INFORMATION: n is a, c, g, or t

```
<400> SEQUENCE: 170
nnnnnnnnnn nnnnnnnnat gttggacaca acaaatt                              37

<210> SEQ ID NO 171
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 171
aauuuguugu guccaacaun nnnnnnnnnn nnnnnnn                              37

<210> SEQ ID NO 172
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 172
aattctcggt gtgccgagt                                                  19

<210> SEQ ID NO 173
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 173
actcggcaca ccgagaatt                                                  19

<210> SEQ ID NO 174
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 174
aattctcggt gtgccgagtn nnnnnnnnn nnnnnnnn                              38

<210> SEQ ID NO 175
<211> LENGTH: 38
```

```
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 175
nnnnnnnnnn nnnnnnnnna ctcggcacac cgagaatt                          38

<210> SEQ ID NO 176
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 176
aauucucggu gugccgagun nnnnnnnnnn nnnnnnnn                          38

<210> SEQ ID NO 177
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 177
aatttctcgt ggccgagat                                               19

<210> SEQ ID NO 178
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 178
atctcggcca cgagaaatt                                               19

<210> SEQ ID NO 179
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
```

```
            sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 179
aatttctcgt ggccgagatn nnnnnnnnnn nnnnnnn                                    37

<210> SEQ ID NO 180
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 180
nnnnnnnnnn nnnnnnnnat ctcggccacg agaaatt                                    37

<210> SEQ ID NO 181
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 181
aauuucucgu ggccgagaun nnnnnnnnnn nnnnnnn                                    37

<210> SEQ ID NO 182
<211> LENGTH: 21
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 182
aattctcggt gtgccgagta t                                                     21

<210> SEQ ID NO 183
<211> LENGTH: 21
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 183
```
atactcggca caccgagaat t                                         21

<210> SEQ ID NO 184
<211> LENGTH: 40
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (22)..(40)
<223> OTHER INFORMATION: n is a, c, g, or t

<400> SEQUENCE: 184
aattctcggt gtgccgagta tnnnnnnnnn nnnnnnnnnn                      40

<210> SEQ ID NO 185
<211> LENGTH: 40
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 185
nnnnnnnnnn nnnnnnnnna tactcggcac accgagaatt                     40

<210> SEQ ID NO 186
<211> LENGTH: 40
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (22)..(40)
<223> OTHER INFORMATION: n is a, c, g, or u

<400> SEQUENCE: 186
aauucucggu gugccgagua unnnnnnnnn nnnnnnnnnn                      40

<210> SEQ ID NO 187
<211> LENGTH: 21
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 187
aatttctcgt ggccgagata t                                         21

<210> SEQ ID NO 188
<211> LENGTH: 21
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 188
atatctcggc cacgagaaat t                                              21

<210> SEQ ID NO 189
<211> LENGTH: 39
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (22)..(39)
<223> OTHER INFORMATION: n is a, c, g, or t

<400> SEQUENCE: 189
aatttctcgt ggccgagata tnnnnnnnnn nnnnnnnnn                            39

<210> SEQ ID NO 190
<211> LENGTH: 39
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 190
nnnnnnnnnn nnnnnnnnat atctcggcca cgagaaatt                            39

<210> SEQ ID NO 191
<211> LENGTH: 39
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (22)..(39)
<223> OTHER INFORMATION: n is a, c, g, or u

<400> SEQUENCE: 191
aauuucucgu ggccgagaua unnnnnnnnn nnnnnnnnn                            39

<210> SEQ ID NO 192
<211> LENGTH: 19

```
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 192
aattgtcgat gtatcgact                                                    19

<210> SEQ ID NO 193
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 193
agtcgataca tcgacaatt                                                    19

<210> SEQ ID NO 194
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 194
aattgtcgat gtatcgactn nnnnnnnnn nnnnnnnn                                 38

<210> SEQ ID NO 195
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 195
nnnnnnnnnn nnnnnnnnna gtcgatacat cgacaatt                                38

<210> SEQ ID NO 196
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
```

```
              sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 196
aauugucgau guaucgacun nnnnnnnnnn nnnnnnnn                              38

<210> SEQ ID NO 197
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (16)..(16)
<223> OTHER INFORMATION: n is a, c, g, or t

<400> SEQUENCE: 197
aattgttcgt ggccgnact                                                   19

<210> SEQ ID NO 198
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (4)..(4)
<223> OTHER INFORMATION: n is a, c, g, or t

<400> SEQUENCE: 198
agtncggcca cgaacaatt                                                   19

<210> SEQ ID NO 199
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(38)
<223> OTHER INFORMATION: n is a, c, g, or t

<400> SEQUENCE: 199
aattgttcgt ggccgnactn nnnnnnnnnn nnnnnnn                               38

<210> SEQ ID NO 200
<211> LENGTH: 38
<212> TYPE: DNA
<213> ORGANISM: Artificial
```

```
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 200
nnnnnnnnnn nnnnnnnnna gtncggccac gaacaatt                              38

<210> SEQ ID NO 201
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (16)..(16)
<223> OTHER INFORMATION: n is a, c, g, or u
<220> FEATURE:
<221> NAME/KEY: misc_feature
<222> LOCATION: (20)..(38)
<223> OTHER INFORMATION: n is a, c, g, or u

<400> SEQUENCE: 201
aauuguucgu ggccgnacun nnnnnnnnnn nnnnnnnn                              38

<210> SEQ ID NO 202
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 202
aattctcctt gtgaggagt                                                  19

<210> SEQ ID NO 203
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 203
actcctcaca aggagaatt                                                  19

<210> SEQ ID NO 204
<211> LENGTH: 38
<212> TYPE: DNA
```

```
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 204
aattctcctt gtgaggagtn nnnnnnnnn nnnnnnn                               38

<210> SEQ ID NO 205
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 205
nnnnnnnnnn nnnnnnnnna ctcctcacaa ggagaatt                             38

<210> SEQ ID NO 206
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 206
aauucuccuu gugaggagun nnnnnnnnn nnnnnnn                               38

<210> SEQ ID NO 207
<211> LENGTH: 18
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 207
aattcttcct ggrggaag                                                   18

<210> SEQ ID NO 208
<211> LENGTH: 18
<212> TYPE: DNA
<213> ORGANISM: Artificial
<220> FEATURE:
<223> OTHER INFORMATION: Polynucleotide encoding constant region of
``` sgRNA/crRNA with non-palindromic recognition site for restriction
enzyme (sense or antisense), polynucleotide encoding for constant
and variable regions of sgRNA or crRNA (sense or antisense), or
sgRNA or crRNA.

<400> SEQUENCE: 208
cttccyccag gaagaatt                                                    18

<210> SEQ ID NO 209
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (19)..(37)
<223> OTHER INFORMATION: n is a, c, g, or t

<400> SEQUENCE: 209
aattcttcct ggrggaagnn nnnnnnnnn nnnnnnn                                37

<210> SEQ ID NO 210
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 210
nnnnnnnnnn nnnnnnnnnc ttccyccagg aagaatt                                37

<210> SEQ ID NO 211
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (19)..(37)
<223> OTHER INFORMATION: n is a, c, g, or u

<400> SEQUENCE: 211
aauucuuccu ggrggaagnn nnnnnnnnn nnnnnnn                                37

<210> SEQ ID NO 212
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or sgRNA or crRNA.

<400> SEQUENCE: 212
aattctccgt gtgcggagt                                                        19

<210> SEQ ID NO 213
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 213
actccgcaca cggagaatt                                                        19

<210> SEQ ID NO 214
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 214
aattctccgt gtgcggagtn nnnnnnnnn nnnnnnnn                                    38

<210> SEQ ID NO 215
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 215
nnnnnnnnnn nnnnnnnna ctccgcacac ggagaatt                                    38

<210> SEQ ID NO 216
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 216

```
aauucuccgu gugcggagun nnnnnnnnnn nnnnnnnn                              38
```

<210> SEQ ID NO 217
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 217

```
aattctcctt gtaaggagt                                                  19
```

<210> SEQ ID NO 218
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 218

```
actccttaca aggagaatt                                                  19
```

<210> SEQ ID NO 219
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 219

```
aattctcctt gtaaggagtn nnnnnnnnn nnnnnnnn                              38
```

<210> SEQ ID NO 220
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 220

```
nnnnnnnnnn nnnnnnnna ctccttacaa ggagaatt                              38
```

<210> SEQ ID NO 221
<211> LENGTH: 38
<212> TYPE: RNA

```
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 221
aauucuccuu guaaggagun nnnnnnnnnn nnnnnnnn                              38

<210> SEQ ID NO 222
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (16)..(16)
<223> OTHER INFORMATION: n is a, c, g, or t

<400> SEQUENCE: 222
aattgttctt gcaagnact                                                  19

<210> SEQ ID NO 223
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (4)..(4)
<223> OTHER INFORMATION: n is a, c, g, or t

<400> SEQUENCE: 223
agtncttgca agaacaatt                                                  19

<210> SEQ ID NO 224
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(38)
<223> OTHER INFORMATION: n is a, c, g, or t

<400> SEQUENCE: 224
aattgttctt gcaagnactn nnnnnnnnnn nnnnnnnn                              38
```

<210> SEQ ID NO 225
<211> LENGTH: 38
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (1)..(19)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 225
nnnnnnnnnn nnnnnnnnna gtncttgcaa gaacaatt                                38

<210> SEQ ID NO 226
<211> LENGTH: 38
<212> TYPE: RNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (16)..(16)
<223> OTHER INFORMATION: n is a, c, g, or u
<220> FEATURE:
<221> NAME/KEY: misc_feature
<222> LOCATION: (20)..(38)
<223> OTHER INFORMATION: n is a, c, g, or u

<400> SEQUENCE: 226
aauuguucuu gcaagnacun nnnnnnnnnn nnnnnnnn                                38

<210> SEQ ID NO 227
<211> LENGTH: 19
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.

<400> SEQUENCE: 227
aattgtcgtt gttacgact                                                    19

<210> SEQ ID NO 228
<211> LENGTH: 19
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.

<400> SEQUENCE: 228

```
agtcgtaaca acgacaatt                                              19

<210> SEQ ID NO 229
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 229
aattgtcgtt gttacgactn nnnnnnnnn nnnnnnn                           38

<210> SEQ ID NO 230
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 230
nnnnnnnnnn nnnnnnnnna gtcgtaacaa cgacaatt                         38

<210> SEQ ID NO 231
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 231
aauugucguu guuacgacun nnnnnnnnn nnnnnnn                           38

<210> SEQ ID NO 232
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 232
aattgtggtt gtgaccact                                              19
```

```
<210> SEQ ID NO 233
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 233
agtggtcaca accacaatt                                                     19

<210> SEQ ID NO 234
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 234
aattgtggtt gtgaccactn nnnnnnnnn nnnnnnn                                  38

<210> SEQ ID NO 235
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 235
nnnnnnnnnn nnnnnnnnna gtggtcacaa ccacaatt                                38

<210> SEQ ID NO 236
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 236
aauugugguu gugaccacun nnnnnnnnn nnnnnnn                                  38

<210> SEQ ID NO 237
<211> LENGTH: 19
<212> TYPE: DNA
```

```
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 237
aattgtcaat gcrttgact                                                 19

<210> SEQ ID NO 238
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 238
agtcaaygca ttgacaatt                                                 19

<210> SEQ ID NO 239
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 239
aattgtcaat gcrttgactn nnnnnnnnn nnnnnnn                              38

<210> SEQ ID NO 240
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 240
nnnnnnnnnn nnnnnnnnna gtcaaygcat tgacaatt                            38

<210> SEQ ID NO 241
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
```

```
<220> FEATURE:
<221> NAME/KEY: misc_feature
<222> LOCATION: (20)..(38)
<223> OTHER INFORMATION: n is a, c, g, or u

<400> SEQUENCE: 241 aaugucaau gcruugacun nnnnnnnnnn nnnnnnnn                               38

<210> SEQ ID NO 242
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 242
aattcttctt gcaagragt                                                   19

<210> SEQ ID NO 243
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 243
actycttgca agaagaatt                                                   19

<210> SEQ ID NO 244
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 244
aattcttctt gcaagragtn nnnnnnnnn nnnnnnnn                               38

<210> SEQ ID NO 245
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 245
```

```
nnnnnnnnnn nnnnnnnnna ctycttgcaa gaagaatt                            38
```

```
<210> SEQ ID NO 246
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 246
aauucuucuu gcaagragun nnnnnnnnnn nnnnnnn                             38
```

```
<210> SEQ ID NO 247
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 247
aattgtgatt gtcatcact                                                 19
```

```
<210> SEQ ID NO 248
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 248
agtgatgaca atcacaatt                                                 19
```

```
<210> SEQ ID NO 249
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 249
aattgtgatt gtcatcactn nnnnnnnnn nnnnnnn                              37
```

```
<210> SEQ ID NO 250
<211> LENGTH: 37
<212> TYPE: DNA
<213> ORGANISM: Artificial
```

```
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 250
nnnnnnnnnn nnnnnnnnag tgatgacaat cacaatt                                 37

<210> SEQ ID NO 251
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 251
aauugugauu gucaucacun nnnnnnnnnn nnnnnnn                                 37

<210> SEQ ID NO 252
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 252
aattctgatt gtcatcagt                                                     19

<210> SEQ ID NO 253
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 253
actgatgaca atcagaatt                                                     19

<210> SEQ ID NO 254
<211> LENGTH: 39
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
```

```
<221> NAME/KEY: misc_feature
<222> LOCATION: (20)..(39)
<223> OTHER INFORMATION: n is a, c, g, or t

<400> SEQUENCE: 254
aattctgatt gtcatcagtn nnnnnnnnnn nnnnnnnnn                            39

<210> SEQ ID NO 255
<211> LENGTH: 39
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 255
nnnnnnnnnn nnnnnnnnnn actgatgaca atcagaatt                            39

<210> SEQ ID NO 256
<211> LENGTH: 39
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(39)
<223> OTHER INFORMATION: n is a, c, g, or u

<400> SEQUENCE: 256
aauucugauu gucaucagun nnnnnnnnnn nnnnnnnnn                            39

<210> SEQ ID NO 257
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 257
aattytgggt gcgcccart                                                  19

<210> SEQ ID NO 258
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 258
aytgggcgca cccaraatt                                                  19
```

<210> SEQ ID NO 259
<211> LENGTH: 38
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 259
aattytgggt gcgcccartn nnnnnnnnnn nnnnnnnn                              38

<210> SEQ ID NO 260
<211> LENGTH: 38
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 260
nnnnnnnnnn nnnnnnnnna ytgggcgcac ccaraatt                              38

<210> SEQ ID NO 261
<211> LENGTH: 38
<212> TYPE: RNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 261
aauuyugggu gcgcccarun nnnnnnnnnn nnnnnnnn                              38

<210> SEQ ID NO 262
<211> LENGTH: 19
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.

<400> SEQUENCE: 262
aattgtgggt gtccycagt                                                  19

<210> SEQ ID NO 263

-continued

```
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 263
actgrggaca cccacaatt                                                   19

<210> SEQ ID NO 264
<211> LENGTH: 39
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(39)
<223> OTHER INFORMATION: n is a, c, g, or t

<400> SEQUENCE: 264
aattgtgggt gtccycagtn nnnnnnnnn nnnnnnnnn                              39

<210> SEQ ID NO 265
<211> LENGTH: 39
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 265
nnnnnnnnnn nnnnnnnnnn actgrggaca cccacaatt                             39

<210> SEQ ID NO 266
<211> LENGTH: 39
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(39)
<223> OTHER INFORMATION: n is a, c, g, or u

<400> SEQUENCE: 266
aauugugggu guccycagun nnnnnnnnn nnnnnnnnn                              39

<210> SEQ ID NO 267
<211> LENGTH: 19
<212> TYPE: DNA
<213> ORGANISM: Artificial
```

```
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 267
aattgtcgat gcatcgact                                                 19

<210> SEQ ID NO 268
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 268
agtcgatgca tcgacaatt                                                 19

<210> SEQ ID NO 269
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 269
aattgtcgat gcatcgactn nnnnnnnnn nnnnnnnn                             38

<210> SEQ ID NO 270
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense),
      or sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 270
nnnnnnnnnn nnnnnnnna gtcgatgcat cgacaatt                             38

<210> SEQ ID NO 271
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
```

```
<221> NAME/KEY: misc_feature
<222> LOCATION: (20)..(38)
<223> OTHER INFORMATION: n is a, c, g, or u

<400> SEQUENCE: 271
aauugucgau gcaucgacun nnnnnnnnnn nnnnnnnn                              38

<210> SEQ ID NO 272
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 272
aattgtcctt gcgrggact                                                   19

<210> SEQ ID NO 273
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 273
agtccycgca aggacaatt                                                   19

<210> SEQ ID NO 274
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 274
aattgtcctt gcgrggactn nnnnnnnnn nnnnnnnn                               38

<210> SEQ ID NO 275
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 275
nnnnnnnnnn nnnnnnnna gtccycgcaa ggacaatt                               38
```

<210> SEQ ID NO 276
<211> LENGTH: 38
<212> TYPE: RNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 276
aauuguccuu gcgrggacun nnnnnnnnnn nnnnnnnn                           38

<210> SEQ ID NO 277
<211> LENGTH: 19
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.

<400> SEQUENCE: 277
aattcttctt gtcagragt                                                19

<210> SEQ ID NO 278
<211> LENGTH: 19
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.

<400> SEQUENCE: 278
actyctgaca agaagaatt                                                19

<210> SEQ ID NO 279
<211> LENGTH: 38
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 279
aattcttctt gtcagragtn nnnnnnnnnn nnnnnnnn                           38

<210> SEQ ID NO 280
<211> LENGTH: 38
<212> TYPE: DNA
<213> ORGANISM: Artificial
<220> FEATURE:

```
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 280
nnnnnnnnnn nnnnnnnnna ctyctgacaa gaagaatt                              38

<210> SEQ ID NO 281
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 281
aauucuucuu gucagragun nnnnnnnnnn nnnnnnnn                              38

<210> SEQ ID NO 282
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 282
aattcttcct ggcggragt                                                   19

<210> SEQ ID NO 283
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 283
actyccgcca ggaagaatt                                                   19

<210> SEQ ID NO 284
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
```

<222> LOCATION: (20)..(38)
<223> OTHER INFORMATION: n is a, c, g, or t

<400> SEQUENCE: 284
aattcttcct ggcggragtn nnnnnnnnnn nnnnnnnn                              38

<210> SEQ ID NO 285
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 285
nnnnnnnnnn nnnnnnnna ctyccgccag gaagaatt                               38

<210> SEQ ID NO 286
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 286
aauucuuccu ggcggragun nnnnnnnnnn nnnnnnnn                              38

<210> SEQ ID NO 287
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 287
aattctccct ggcgggagt                                                   19

<210> SEQ ID NO 288
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 288
actcccgcca gggagaatt                                                   19

```
<210> SEQ ID NO 289
<211> LENGTH: 39
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(39)
<223> OTHER INFORMATION: n is a, c, g, or t

<400> SEQUENCE: 289
aattctccct ggcgggagtn nnnnnnnnnn nnnnnnnn                                39

<210> SEQ ID NO 290
<211> LENGTH: 39
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(20)
<223> OTHER INFORMATION: n is a, c, g, or t

<400> SEQUENCE: 290
nnnnnnnnnn nnnnnnnnnn actcccgcca gggagaatt                               39

<210> SEQ ID NO 291
<211> LENGTH: 39
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(39)
<223> OTHER INFORMATION: n is a, c, g, or u

<400> SEQUENCE: 291
aauucucccu ggcgggagun nnnnnnnnnn nnnnnnnn                                39

<210> SEQ ID NO 292
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 292
aatttgtcgt gatcgacat                                                    19

<210> SEQ ID NO 293
<211> LENGTH: 19
```

```
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 293
atgtcgatca cgacaaatt                                                   19

<210> SEQ ID NO 294
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 294
aatttgtcgt gatcgacatn nnnnnnnnn nnnnnnn                                37

<210> SEQ ID NO 295
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 295
nnnnnnnnnn nnnnnnnnat gtcgatcacg acaaatt                               37

<210> SEQ ID NO 296
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 296
aauuugucgu gaucgacaun nnnnnnnnn nnnnnnn                                37

<210> SEQ ID NO 297
<211> LENGTH: 19
<212> TYPE: DNA
<213> ORGANISM: Artificial
<220> FEATURE:
```

```
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (15)..(15)
<223> OTHER INFORMATION: n is a, c, g, or t

<400> SEQUENCE: 297
aatttgttct gccgnacat                                                    19

<210> SEQ ID NO 298
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (5)..(5)
<223> OTHER INFORMATION: n is a, c, g, or t

<400> SEQUENCE: 298
atgtncggca gaacaaatt                                                    19

<210> SEQ ID NO 299
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (20)..(37)
<223> OTHER INFORMATION: n is a, c, g, or t

<400> SEQUENCE: 299
aatttgttct gccgnacatn nnnnnnnnn nnnnnnn                                  37

<210> SEQ ID NO 300
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 300
```

```
nnnnnnnnnn nnnnnnnnat gtncggcaga acaaatt                              37
```

<210> SEQ ID NO 301
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature
<222> LOCATION: (20)..(37)
<223> OTHER INFORMATION: n is a, c, g, or u

<400> SEQUENCE: 301

```
aauuuguucu gccgnacaun nnnnnnnnnn nnnnnnn                              37
```

<210> SEQ ID NO 302
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 302

```
aatttctcct ggaggagat                                                  19
```

<210> SEQ ID NO 303
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 303

```
atctcctcca ggagaaatt                                                  19
```

<210> SEQ ID NO 304
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 304

```
aatttctcct ggaggagatn nnnnnnnnn nnnnnnn                               37
```

```
<210> SEQ ID NO 305
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 305
nnnnnnnnnn nnnnnnnnat ctcctccagg agaaatt                              37

<210> SEQ ID NO 306
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 306
aauuucuccu ggaggagaun nnnnnnnnnn nnnnnnn                              37

<210> SEQ ID NO 307
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 307
aatttcttct grggaagat                                                   19

<210> SEQ ID NO 308
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 308
atcttccyca gaagaaatt                                                   19

<210> SEQ ID NO 309
<211> LENGTH: 37
<212> TYPE: DNA
<213> ORGANISM: Artificial
<220> FEATURE:
<223> OTHER INFORMATION: Polynucleotide encoding constant region of
``` sgRNA/crRNA with non-palindromic recognition site for restriction
enzyme (sense or antisense), polynucleotide encoding for constant
and variable regions of sgRNA or crRNA (sense or antisense), or
sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 309
aatttcttct grggaagatn nnnnnnnnn nnnnnnn                              37

<210> SEQ ID NO 310
<211> LENGTH: 37
<212> TYPE: DNA
<213> ORGANISM: Artificial
<220> FEATURE:
<223> OTHER INFORMATION: Polynucleotide encoding constant region of
sgRNA/crRNA with non-palindromic recognition site for restriction
enzyme (sense or antisense), polynucleotide encoding for constant
and variable regions of sgRNA or crRNA (sense or antisense), or
sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 310
nnnnnnnnnn nnnnnnnnat cttccycaga agaaatt                             37

<210> SEQ ID NO 311
<211> LENGTH: 37
<212> TYPE: RNA
<213> ORGANISM: Artificial
<220> FEATURE:
<223> OTHER INFORMATION: Polynucleotide encoding constant region of
sgRNA/crRNA with non-palindromic recognition site for restriction
enzyme (sense or antisense), polynucleotide encoding for constant
and variable regions of sgRNA or crRNA (sense or antisense), or
sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 311
aauuucuucu grggaagaun nnnnnnnnn nnnnnnn                              37

<210> SEQ ID NO 312
<211> LENGTH: 19
<212> TYPE: DNA
<213> ORGANISM: Artificial
<220> FEATURE:
<223> OTHER INFORMATION: Polynucleotide encoding constant region of
sgRNA/crRNA with non-palindromic recognition site for restriction
enzyme (sense or antisense), polynucleotide encoding for constant
and variable regions of sgRNA or crRNA (sense or antisense), or
sgRNA or crRNA.

<400> SEQUENCE: 312
aatttctcct ggcggagat                                                 19

<210> SEQ ID NO 313
<211> LENGTH: 19
<212> TYPE: DNA
<213> ORGANISM: Artificial
<220> FEATURE:
<223> OTHER INFORMATION: Polynucleotide encoding constant region of
sgRNA/crRNA with non-palindromic recognition site for restriction
enzyme (sense or antisense), polynucleotide encoding for constant
and variable regions of sgRNA or crRNA (sense or antisense), or sgRNA or crRNA.

<400> SEQUENCE: 313
atctccgcca ggagaaatt                                                          19

<210> SEQ ID NO 314
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 314
aatttctcct ggcggagatn nnnnnnnnn nnnnnnn                                       37

<210> SEQ ID NO 315
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 315
nnnnnnnnnn nnnnnnnnat ctccgccagg agaaatt                                      37

<210> SEQ ID NO 316
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 316
aauuucuccu ggcggagaun nnnnnnnnn nnnnnnn                                       37

<210> SEQ ID NO 317
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 317
aatttctcct gaaggagat                                                      19

<210> SEQ ID NO 318
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 318
atctccttca ggagaaatt                                                      19

<210> SEQ ID NO 319
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 319
aatttctcct gaaggagatn nnnnnnnnn nnnnnnn                                   37

<210> SEQ ID NO 320
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 320
nnnnnnnnnn nnnnnnnnat ctccttcagg agaaatt                                  37

<210> SEQ ID NO 321
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 321
aauuucuccu gaaggagaun nnnnnnnnn nnnnnnn                                   37

<210> SEQ ID NO 322
<211> LENGTH: 19
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (15)..(15)
<223> OTHER INFORMATION: n is a, c, g, or t

<400> SEQUENCE: 322
aatttgttct caagnacat                                                19

<210> SEQ ID NO 323
<211> LENGTH: 19
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (5)..(5)
<223> OTHER INFORMATION: n is a, c, g, or t

<400> SEQUENCE: 323
atgtncttga gaacaaatt                                                19

<210> SEQ ID NO 324
<211> LENGTH: 37
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (20)..(37)
<223> OTHER INFORMATION: n is a, c, g, or t

<400> SEQUENCE: 324
aatttgttct caagnacatn nnnnnnnnn nnnnnnn                              37

<210> SEQ ID NO 325
<211> LENGTH: 37
<212> TYPE: DNA
<213> ORGANISM: Artificial
<220> FEATURE:
<223> OTHER INFORMATION: Polynucleotide encoding constant region of
    sgRNA/crRNA with non-palindromic recognition site for restriction
    enzyme (sense or antisense), polynucleotide encoding for constant
    and variable regions of sgRNA or crRNA (sense or antisense), or
    sgRNA or crRNA.
<220> FEATURE:
<221> NAME/KEY: misc_feature
<222> LOCATION: (1)..(18)
<223> OTHER INFORMATION: n is a, c, g, or t

```
<220> FEATURE:
<221> NAME/KEY: misc_feature
<222> LOCATION: (23)..(23)
<223> OTHER INFORMATION: n is a, c, g, or t

<400> SEQUENCE: 325
nnnnnnnnnn nnnnnnnnat gtncttgaga acaaatt                              37

<210> SEQ ID NO 326
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature
<222> LOCATION: (20)..(37)
<223> OTHER INFORMATION: n is a, c, g, or u

<400> SEQUENCE: 326
aauuuguucu caagnacaun nnnnnnnnnn nnnnnnn                              37

<210> SEQ ID NO 327
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 327
aatttgtcgt gtacgacat                                                  19

<210> SEQ ID NO 328
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 328
atgtcgtaca cgacaaatt                                                  19

<210> SEQ ID NO 329
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
```

```
<223> OTHER INFORMATION: n is a, c, g, or t

<400> SEQUENCE: 329
aatttgtcgt gtacgacatn nnnnnnnnnn nnnnnnn                                37

<210> SEQ ID NO 330
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 330
nnnnnnnnnn nnnnnnnnat gtcgtacacg acaaatt                                37

<210> SEQ ID NO 331
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 331
aauuugucgu guacgacaun nnnnnnnnnn nnnnnnn                                37

<210> SEQ ID NO 332
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 332
aatttgtggt ggaccacat                                                    19

<210> SEQ ID NO 333
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 333
atgtggtcca ccacaaatt                                                    19
```

```
<210> SEQ ID NO 334
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 334
aatttgtggt ggaccacatn nnnnnnnnn nnnnnnn                              37

<210> SEQ ID NO 335
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 335
nnnnnnnnnn nnnnnnnnat gtggtccacc acaaatt                             37

<210> SEQ ID NO 336
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 336
aauuuguggu ggaccacaun nnnnnnnnn nnnnnnn                              37

<210> SEQ ID NO 337
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 337
aatttgtcat crttgacat                                                 19

<210> SEQ ID NO 338
<211> LENGTH: 19
<212> TYPE: DNA
```

```
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 338
atgtcaayga tgacaaatt                                                 19

<210> SEQ ID NO 339
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 339
aatttgtcat crttgacatn nnnnnnnnn nnnnnnn                              37

<210> SEQ ID NO 340
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 340
nnnnnnnnnn nnnnnnnnat gtcaaygatg acaaatt                             37

<210> SEQ ID NO 341
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 341
aauuugucau cruugacaun nnnnnnnnnn nnnnnnn                             37

<210> SEQ ID NO 342
<211> LENGTH: 19
<212> TYPE: DNA
<213> ORGANISM: Artificial
<220> FEATURE:
<223> OTHER INFORMATION: Polynucleotide encoding constant region of
``` sgRNA/crRNA with non-palindromic recognition site for restriction
enzyme (sense or antisense), polynucleotide encoding for constant
and variable regions of sgRNA or crRNA (sense or antisense), or
sgRNA or crRNA.

<400> SEQUENCE: 342
aatttcttct caagragat                                                19

<210> SEQ ID NO 343
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 343
atctycttga gaagaaatt                                                19

<210> SEQ ID NO 344
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 344
aatttcttct caagragatn nnnnnnnnnn nnnnnnn                             37

<210> SEQ ID NO 345
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 345
nnnnnnnnnn nnnnnnnnat ctycttgaga agaaatt                             37

<210> SEQ ID NO 346
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)

<223> OTHER INFORMATION: n is a, c, g, or u

<400> SEQUENCE: 346
aauuucuucu caagragaun nnnnnnnnnn nnnnnnn        37

<210> SEQ ID NO 347
<211> LENGTH: 19
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.

<400> SEQUENCE: 347
aatttctgat gcatcagat        19

<210> SEQ ID NO 348
<211> LENGTH: 19
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.

<400> SEQUENCE: 348
atctgatgca tcagaaatt        19

<210> SEQ ID NO 349
<211> LENGTH: 38
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 349
aatttctgat gcatcagatn nnnnnnnnn nnnnnnnn        38

<210> SEQ ID NO 350
<211> LENGTH: 38
<212> TYPE: DNA
<213> ORGANISM: Artificial
<220> FEATURE:
<223> OTHER INFORMATION: Polynucleotide encoding constant region of
     sgRNA/crRNA with non-palindromic recognition site for restriction
     enzyme (sense or antisense), polynucleotide encoding for constant
     and variable regions of sgRNA or crRNA (sense or antisense), or
     sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 350
nnnnnnnnnn nnnnnnnnna tctgatgcat cagaaatt        38

```
<210> SEQ ID NO 351
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 351
aauuucugau gcaucagaun nnnnnnnnnn nnnnnnn                                  38

<210> SEQ ID NO 352
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 352
aattaytggt cgcccarat                                                      19

<210> SEQ ID NO 353
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 353
atytgggcga ccartaatt                                                      19

<210> SEQ ID NO 354
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 354
aattaytggt cgcccaratn nnnnnnnnnn nnnnnnn                                  37

<210> SEQ ID NO 355
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
``` enzyme (sense or antisense), polynucleotide encoding for constant
and variable regions of sgRNA or crRNA (sense or antisense), or
sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 355
nnnnnnnnnn nnnnnnnnat ytgggcgacc artaatt                                37

<210> SEQ ID NO 356
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 356
aauuayucca gcgggaraun nnnnnnnnnn nnnnnnn                                37

<210> SEQ ID NO 357
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 357
aatttgtgrt gccycacat                                                    19

<210> SEQ ID NO 358
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 358
atgtgrggca ycacaaatt                                                    19

<210> SEQ ID NO 359
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 359
aatttgtgrt gccycacatn nnnnnnnnnn nnnnnnnn                                38

<210> SEQ ID NO 360
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 360
nnnnnnnnnn nnnnnnnnna tgtgrggcay cacaaatt                                38

<210> SEQ ID NO 361
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 361
aauuugugru gccycacaun nnnnnnnnnn nnnnnnnn                                38

<210> SEQ ID NO 362
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 362
aatttgtcgt catcgacat                                                     19

<210> SEQ ID NO 363
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 363
atgtcgatga cgacaaatt                                                     19

<210> SEQ ID NO 364

```
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 364
aatttgtcgt catcgacatn nnnnnnnnn nnnnnn                               37

<210> SEQ ID NO 365
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 365
nnnnnnnnnn nnnnnnnnat gtcgatgacg acaaatt                             37

<210> SEQ ID NO 366
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 366
aauuugucgu caucgacaun nnnnnnnnn nnnnnn                               37

<210> SEQ ID NO 367
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 367
aatttgtcct cgrggacat                                                 19

<210> SEQ ID NO 368
<211> LENGTH: 19
<212> TYPE: DNA
<213> ORGANISM: Artificial
```

```
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 368
atgtccycga ggacaaatt                                                    19

<210> SEQ ID NO 369
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 369
aatttgtcct cgrggacatn nnnnnnnnnn nnnnnnn                                 37

<210> SEQ ID NO 370
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 370
nnnnnnnnnn nnnnnnnnat gtccycgagg acaaatt                                 37

<210> SEQ ID NO 371
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 371
aauuuguccu cgrggacaun nnnnnnnnnn nnnnnnn                                 37

<210> SEQ ID NO 372
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
``` enzyme (sense or antisense), polynucleotide encoding for constant
and variable regions of sgRNA or crRNA (sense or antisense), or
sgRNA or crRNA.

<400> SEQUENCE: 372
aatttcttct gcagragat                                                19

<210> SEQ ID NO 373
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 373
atctyctgca gaagaaatt                                                19

<210> SEQ ID NO 374
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 374
aatttcttct gcagragatn nnnnnnnnn nnnnnnnn                             38

<210> SEQ ID NO 375
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 375
nnnnnnnnnn nnnnnnnna tctyctgcag aagaaatt                             38

<210> SEQ ID NO 376
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 376
aauuucuucu gcagragaun nnnnnnnnnn nnnnnnnn                              38

<210> SEQ ID NO 377
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 377
aatttcttct gcggragat                                                   19

<210> SEQ ID NO 378
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 378
atctyccgca gaagaaatt                                                   19

<210> SEQ ID NO 379
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or t

<400> SEQUENCE: 379
aatttcttct gcggragatn nnnnnnnnnn nnnnnnn                               37

<210> SEQ ID NO 380
<211> LENGTH: 37
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 380
nnnnnnnnnn nnnnnnnnat ctyccgcaga agaaatt                               37

<210> SEQ ID NO 381

```
<211> LENGTH: 37
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(37)
<223> OTHER INFORMATION: n is a, c, g, or u

<400> SEQUENCE: 381
aauuucuucu gcggragaun nnnnnnnnnn nnnnnnn                                37

<210> SEQ ID NO 382
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 382
aatttgtgtt gcaacacat                                                   19

<210> SEQ ID NO 383
<211> LENGTH: 19
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 383
atgtgttgca acacaaatt                                                   19

<210> SEQ ID NO 384
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (20)..(38)
<223> OTHER INFORMATION: n is a, c, g, or t

<400> SEQUENCE: 384
aatttgtgtt gcaacacatn nnnnnnnnn nnnnnnnn                                38

<210> SEQ ID NO 385
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
```

```
        and variable regions of sgRNA or crRNA (sense or antisense), or
        sgRNA or crRNA.
<220> FEATURE:
<221> NAME/KEY: misc_feature
<222> LOCATION: (1)..(19)
<223> OTHER INFORMATION: n is a, c, g, or t

<400> SEQUENCE: 385
nnnnnnnnnn nnnnnnnnna tgtgttgcaa cacaaatt                              38

<210> SEQ ID NO 386
<211> LENGTH: 38
<212> TYPE: RNA
<213> ORGANISM: Artificial
<220> FEATURE:
<223> OTHER INFORMATION: Polynucleotide encoding constant region of
        sgRNA/crRNA with non-palindromic recognition site for restriction
        enzyme (sense or antisense), polynucleotide encoding for constant
        and variable regions of sgRNA or crRNA (sense or antisense), or
        sgRNA or crRNA.
<220> FEATURE:
<221> NAME/KEY: misc_feature
<222> LOCATION: (20)..(38)
<223> OTHER INFORMATION: n is a, c, g, or u

<400> SEQUENCE: 386
aauuuguguu gcaacacaun nnnnnnnnnn nnnnnnn                               38

<210> SEQ ID NO 387
<211> LENGTH: 20
<212> TYPE: DNA
<213> ORGANISM: Artificial
<220> FEATURE:
<223> OTHER INFORMATION: Polynucleotide encoding constant region of
        sgRNA/crRNA with non-palindromic recognition site for restriction
        enzyme (sense or antisense), polynucleotide encoding for constant
        and variable regions of sgRNA or crRNA (sense or antisense), or
        sgRNA or crRNA.

<400> SEQUENCE: 387
aatttcctgt gcatcaggat                                                  20

<210> SEQ ID NO 388
<211> LENGTH: 20
<212> TYPE: DNA
<213> ORGANISM: Artificial
<220> FEATURE:
<223> OTHER INFORMATION: Polynucleotide encoding constant region of
        sgRNA/crRNA with non-palindromic recognition site for restriction
        enzyme (sense or antisense), polynucleotide encoding for constant
        and variable regions of sgRNA or crRNA (sense or antisense), or
        sgRNA or crRNA.

<400> SEQUENCE: 388
atcctgatgc acaggaaatt                                                  20

<210> SEQ ID NO 389
<211> LENGTH: 38
<212> TYPE: DNA
<213> ORGANISM: Artificial
<220> FEATURE:
<223> OTHER INFORMATION: Polynucleotide encoding constant region of
        sgRNA/crRNA with non-palindromic recognition site for restriction
        enzyme (sense or antisense), polynucleotide encoding for constant
        and variable regions of sgRNA or crRNA (sense or antisense), or
        sgRNA or crRNA.
<220> FEATURE:
<221> NAME/KEY: misc_feature
<222> LOCATION: (21)..(38)
<223> OTHER INFORMATION: n is a, c, g, or t
```

```
<400> SEQUENCE: 389
aatttcctgt gcatcaggat nnnnnnnnnn nnnnnnnn                              38

<210> SEQ ID NO 390
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 390
nnnnnnnnnn nnnnnnnnat cctgatgcac aggaaatt                              38

<210> SEQ ID NO 391
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (21)..(38)
<223> OTHER INFORMATION: n is a, c, g, or u

<400> SEQUENCE: 391 aauuccugu gcaucaggau nnnnnnnnnn nnnnnnnn                               38

<210> SEQ ID NO 392
<211> LENGTH: 20
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 392
aatttcctgt gccycaggat                                                  20

<210> SEQ ID NO 393
<211> LENGTH: 20
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 393
atcctgrggc acaggaaatt                                                  20

<210> SEQ ID NO 394
<211> LENGTH: 38
```

```
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (21)..(38)
<223> OTHER INFORMATION: n is a, c, g, or t

<400> SEQUENCE: 394
aatttcctgt gccycaggat nnnnnnnnnn nnnnnnnn                              38

<210> SEQ ID NO 395
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 395
nnnnnnnnnn nnnnnnnnat cctgrggcac aggaaatt                              38

<210> SEQ ID NO 396
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (21)..(38)
<223> OTHER INFORMATION: n is a, c, g, or u

<400> SEQUENCE: 396 aauuccugu gccycaggau nnnnnnnnnn nnnnnnnn                               38

<210> SEQ ID NO 397
<211> LENGTH: 20
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 397
aatttccttt gcagraggat                                                  20

<210> SEQ ID NO 398
<211> LENGTH: 20
<212> TYPE: DNA
<213> ORGANISM: Artificial
<220> FEATURE:
```

<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 398
atcctyctgc aaaggaaatt                                               20

<210> SEQ ID NO 399
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (21)..(38)
<223> OTHER INFORMATION: n is a, c, g, or t

<400> SEQUENCE: 399 aatttcctttt gcagraggat nnnnnnnnnn nnnnnnnn                           38

<210> SEQ ID NO 400
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 400
nnnnnnnnnn nnnnnnnnat cctyctgcaa aggaaatt                            38

<210> SEQ ID NO 401
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (21)..(38)
<223> OTHER INFORMATION: n is a, c, g, or u

<400> SEQUENCE: 401
aauuuccuuu gcagraggau nnnnnnnnnn nnnnnnnn                            38

<210> SEQ ID NO 402
<211> LENGTH: 20
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant and variable regions of sgRNA or crRNA (sense or antisense), or sgRNA or crRNA.

<400> SEQUENCE: 402
aatttcgtgt gcaacacgat                    20

<210> SEQ ID NO 403
<211> LENGTH: 20
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.

<400> SEQUENCE: 403
atcgtgttgc acacgaaatt                    20

<210> SEQ ID NO 404
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (21)..(38)
<223> OTHER INFORMATION: n is a, c, g, or t

<400> SEQUENCE: 404
aatttcgtgt gcaacacgat nnnnnnnnnn nnnnnnnn     38

<210> SEQ ID NO 405
<211> LENGTH: 38
<212> TYPE: DNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (1)..(18)
<223> OTHER INFORMATION: n is a, c, g, or t

<400> SEQUENCE: 405
nnnnnnnnnn nnnnnnnnat cgtgttgcac acgaaatt     38

<210> SEQ ID NO 406
<211> LENGTH: 38
<212> TYPE: RNA
<213> ORGANISM: Artificial
<220> FEATURE:
<223> OTHER INFORMATION: Polynucleotide encoding constant region of
      sgRNA/crRNA with non-palindromic recognition site for restriction
      enzyme (sense or antisense), polynucleotide encoding for constant
      and variable regions of sgRNA or crRNA (sense or antisense), or
      sgRNA or crRNA.
<220> FEATURE:
<221> NAME/KEY: misc_feature
<222> LOCATION: (21)..(38)
<223> OTHER INFORMATION: n is a, c, g, or u

<400> SEQUENCE: 406
aauuucgugu gcaacacgau nnnnnnnnnn nnnnnnnn    38

<210> SEQ ID NO 407
<211> LENGTH: 1653
<212> TYPE: DNA
<213> ORGANISM: Artificial
<220> FEATURE:
<223> OTHER INFORMATION: Polynucleotide containing EGFP Transgene
      sequence

<400> SEQUENCE: 407

```
agctcggatc caaaagctta atcagttgt gttaaataag agacattcaa aataaatgta      60
aatgagctct ccaaatcagc agacttaaca ttctttaaaa tgattgattc aatagtgata     120
aaaatcaggc atagccagtt gtaactttag ataaattaca gaaaatgtca aatacagaga     180
accgattctt ttttatgata catccaagca cacatttaac acaatccagg caaaccccga     240
atttcacagt cacaagcact gtttgtacaa gagctttgcc taaggacaca cagtctctat     300
aagtccaggt cgttggtttc actcttattt taaacatgtg acatttttcc tgccatcctg     360
tcttaggctg ctgtttgctt cattccatgt cacattaaat tcctcagtag cacctttttac    420
acacacagcc aatcttttcc agaaaattca attgctttga agagataatg tgtgaacaaa    480
tccatttaga aaaggaaaat taagaatttg taaaatcatc tgtaaattgt tggcattctt    540
ctgtatatga acatcacatc atttacaggt aaaggtctgg tcattaatta tatgacaatt    600
tactggtatt attttgtgaa aggggctatt ttcaatgcgt tcatccatcc ttttcatccc    660
tcaaatctct cattcacgtc ccctcccca tctgcacact ttatctcatt ttccaccctg     720
ctggaatctg agcacttgtg cagttatcag ggctcctgta tttaggaggc tctgggtgtc    780
catgtagggg acgaacagaa acactgcaga cctttataga agaacaattg ataagagtcc    840
tcatacataa agactccatt agtaagccag tgacccagga gcccagacca acagcaaagc    900
agacagtgac catggtgagc aagggcgagg agctgttcac cggggtggtg cccatcctgg    960
tcgagctgga cggcgacgta aacggccaca agttcagcgt gtccggcgag ggcgagggcg   1020
atgccaccta cggcaagctg accctgaagt tcatctgcac caccggcaag ctgcccgtgc   1080
cctggcccac cctcgtgacc accctgacct acggcgtgca gtgcttcagc cgctaccccg   1140
accacatgaa gcagcacgac ttcttcaagt ccgccatgcc cgaaggctac gtccaggagc   1200
gcaccatctt cttcaaggac gacggcaact acaagacccg cgccgaggtg aagttcgagg   1260
gcgacaccct ggtgaaccgc atcgagctga agggcatcga cttcaaggag gacggcaaca   1320
tcctggggca aagctggag tacaactaca acagccacaa cgtctatatc atggccgaca   1380
agcagaagaa cggcatcaag gtgaacttca agatccgcca caacatcgag gacggcagcg   1440
tgcagctcgc cgaccactac cagcagaaca cccccatcgg cgacggcccc gtgctgctgc   1500
ccgacaacca ctacctgagc acccagtccg ccctgagcaa agaccccaac gagaagcgcg   1560
atcacatggt cctgctggag ttcgtgaccg ccgccgggat cactctcggc atggacgagc   1620
tgtacaagta gtaaacgttg cagcaagatt aca                                 1653
```

<210> SEQ ID NO 408
<211> LENGTH: 100
<212> TYPE: DNA
<213> ORGANISM: Artificial
<220> FEATURE:
<223> OTHER INFORMATION: PCR Product

<400> SEQUENCE: 408
cagcaaagca gacagtgacc atggtgagca agggcgagga gctgttcacc ggggtggtgc    60
ccatcctggt cgagctggac ggcgacgtaa acggccacaa    100

<210> SEQ ID NO 409
<211> LENGTH: 20
<212> TYPE: DNA
<213> ORGANISM: Artificial
<220> FEATURE:
<223> OTHER INFORMATION: Forward Primer

<400> SEQUENCE: 409
cagcaaagca gacagtgacc    20

<210> SEQ ID NO 410
<211> LENGTH: 18
<212> TYPE: DNA
<213> ORGANISM: Artificial
<220> FEATURE:
<223> OTHER INFORMATION: Reverse Primer

<400> SEQUENCE: 410
ttgtggccgt ttacgtcg    18

<210> SEQ ID NO 411
<211> LENGTH: 49
<212> TYPE: DNA
<213> ORGANISM: Artificial
<220> FEATURE:
<223> OTHER INFORMATION: Digested PCR Product(1)

<400> SEQUENCE: 411
cagcaaagca gacagtgacc atggtgagca agggcgagga gctgttcac    49

<210> SEQ ID NO 412
<211> LENGTH: 51
<212> TYPE: DNA
<213> ORGANISM: Artificial
<220> FEATURE:
<223> OTHER INFORMATION: Digested PCR Product(2)

<400> SEQUENCE: 412
cggggtggtg cccatcctgg tcgagctgga cggcgacgta aacggccaca a    51

<210> SEQ ID NO 413
<211> LENGTH: 18
<212> TYPE: DNA
<213> ORGANISM: Artificial
<220> FEATURE:
<223> OTHER INFORMATION: MmeI digested product(1)

<400> SEQUENCE: 413
gggcgaggag ctgttcac    18

<210> SEQ ID NO 414
<211> LENGTH: 18
<212> TYPE: DNA
<213> ORGANISM: Artificial
<220> FEATURE:
<223> OTHER INFORMATION: MmeI digested product(2)

<400> SEQUENCE: 414
gggtggtgcc catcctgg    18

-continued

```
<210> SEQ ID NO 415
<211> LENGTH: 29
<212> TYPE: DNA
<213> ORGANISM: Artificial
<220> FEATURE:
<223> OTHER INFORMATION: T7 Promoter
<220> FEATURE:
<221> NAME/KEY: misc_feature
<222> LOCATION: (28)..(29)
<223> OTHER INFORMATION: n is a, c, g, or t

<400> SEQUENCE: 415
cggcgaaatt aatacgactc actatagnn                                    29

<210> SEQ ID NO 416
<211> LENGTH: 102
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: n is a, c, g, or u

<400> SEQUENCE: 416
nnnnnnnnnn nnnnnnnnnn guuuuagagc uagaaauagc aaguuaaaau aaggcuaguc    60
cguuaucaac uugaaaaagu ggcaccgagu cggugcuuuu uu                     102

<210> SEQ ID NO 417
<211> LENGTH: 102
<212> TYPE: DNA
<213> ORGANISM: Streptococcus pyogenes
<220> FEATURE:
<221> NAME/KEY: misc_feature
<222> LOCATION: (1)..(20)
<223> OTHER INFORMATION: n is a, c, g, or t

<400> SEQUENCE: 417
nnnnnnnnnn nnnnnnnnnn gttttagagc tagaaatagc aagttaaaat aaggctagtc    60
cgttatcaac ttgaaaaagt ggcaccgagt cggtgctttt tt                     102

<210> SEQ ID NO 418
<211> LENGTH: 102
<212> TYPE: DNA
<213> ORGANISM: Streptococcus pyogenes
<220> FEATURE:
<221> NAME/KEY: misc_feature
<222> LOCATION: (1)..(20)
<223> OTHER INFORMATION: n is a, c, g, or t

<400> SEQUENCE: 418
nnnnnnnnnn nnnnnnnnnn caaaatctcg atctttatcg ttcaatttta ttccgatcag    60
gcaatagttg aacttttca ccgtggctca gccacgaaaa aa                      102

<210> SEQ ID NO 419
<211> LENGTH: 102
<212> TYPE: DNA
<213> ORGANISM: Artificial Sequence
<220> FEATURE:
<223> OTHER INFORMATION: polynucleotides encoding for a sgRNA and having
      non-palindromic recognition sites
<220> FEATURE:
<221> NAME/KEY: misc_feature
<222> LOCATION: (1)..(20)
<223> OTHER INFORMATION: n is a, c, g, or t

<400> SEQUENCE: 419
nnnnnnnnnn nnnnnnnnnn gttggagagc tagaaatagc aagttccaat aaggctagtc    60
```
cgttatcaac ttgaaaaagt ggcaccgagt cggtgctttt tt                           102

<210> SEQ ID NO 420
<211> LENGTH: 102
<212> TYPE: DNA
<213> ORGANISM: Artificial Sequence
<220> FEATURE:
<223> OTHER INFORMATION: polynucleotides encoding for a sgRNA and having
      non-palindromic recognition sites
<220> FEATURE:
<221> NAME/KEY: misc_feature
<222> LOCATION: (1)..(20)
<223> OTHER INFORMATION: n is a, c, g, or t

<400> SEQUENCE: 420
nnnnnnnnnn nnnnnnnnnn caacctctcg atctttatcg ttcaaggtta ttccgatcag        60
gcaatagttg aacttttca ccgtggctca gccacgaaaa aa                            102

<210> SEQ ID NO 421
<211> LENGTH: 102
<212> TYPE: DNA
<213> ORGANISM: Artificial Sequence
<220> FEATURE:
<223> OTHER INFORMATION: polynucleotides encoding for a sgRNA and having
      non-palindromic recognition sites
<220> FEATURE:
<221> NAME/KEY: misc_feature
<222> LOCATION: (1)..(20)
<223> OTHER INFORMATION: n is a, c, g, or t

<400> SEQUENCE: 421
nnnnnnnnnn nnnnnnnnnn cggttggagc tagaaatagc aagtcaacct aaggctagtc        60
cgttatcaac ttgaaaaagt ggcaccgagt cggtgctttt tt                           102

<210> SEQ ID NO 422
<211> LENGTH: 102
<212> TYPE: DNA
<213> ORGANISM: Artificial Sequence
<220> FEATURE:
<223> OTHER INFORMATION: polynucleotides encoding for a sgRNA and having
      non-palindromic recognition sites
<220> FEATURE:
<221> NAME/KEY: misc_feature
<222> LOCATION: (1)..(20)
<223> OTHER INFORMATION: n is a, c, g, or t

<400> SEQUENCE: 422
nnnnnnnnnn nnnnnnnnnn gccaacctcg atctttatcg ttcagttgga ttccgatcag        60
gcaatagttg aacttttca ccgtggctca gccacgaaaa aa                            102

<210> SEQ ID NO 423
<211> LENGTH: 101
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: n is a, c, g, or u

<400> SEQUENCE: 423
nnnnnnnnnn nnnnnnnnnn guuuuagagc uagaaauagc aaguuaaaau aaggcuaguc        60
cguuaucaac uugaaaaagu ggcaccgagu cggugcuuuu u                            101

<210> SEQ ID NO 424
<211> LENGTH: 101

```
<212> TYPE: DNA
<213> ORGANISM: Streptococcus pyogenes
<220> FEATURE:
<221> NAME/KEY: misc_feature
<222> LOCATION: (1)..(20)
<223> OTHER INFORMATION: n is a, c, g, or t

<400> SEQUENCE: 424
nnnnnnnnnn nnnnnnnnnn gttttagagc tagaaatagc aagttaaaat aaggctagtc    60
cgttatcaac ttgaaaaagt ggcaccgagt cggtgctttt t                       101

<210> SEQ ID NO 425
<211> LENGTH: 101
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(20)
<223> OTHER INFORMATION: n is a, c, g, or t

<400> SEQUENCE: 425
nnnnnnnnnn nnnnnnnnnn gttttagagc tagaaatagc aagttaaaat aaggctagtc    60
cgttatcaac ttgaaaaagt ggcaccgagt cggtgctttt t                       101

<210> SEQ ID NO 426
<211> LENGTH: 100
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(19)
<223> OTHER INFORMATION: n is a, c, g, or t

<400> SEQUENCE: 426
nnnnnnnnnn nnnnnnnnng gttggaagct agaaatagca agtccaacta aggctagtcc    60
gttatcaact tgaaaagtg gcaccgagtc ggtgctttt                           100

<210> SEQ ID NO 427
<211> LENGTH: 99
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(18)
<223> OTHER INFORMATION: n is a, c, g, or t

<400> SEQUENCE: 427
nnnnnnnnnn nnnnnnnngt gttggagcta gaaatagcaa gtcaacataa ggctagtccg    60
ttatcaactt gaaaagtgg caccgagtcg gtgctttt                             99

<210> SEQ ID NO 428
<211> LENGTH: 99
<212> TYPE: DNA
<213> ORGANISM: Artificial Sequence
<220> FEATURE:
```

```
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(17)
<223> OTHER INFORMATION: n is a, c, g, or t

<400> SEQUENCE: 428
nnnnnnnnnn nnnnnnnccg gttggagcta gaaatagcaa gtcaacctaa ggctagtccg      60
ttatcaactt gaaaaagtgg caccgagtcg gtgcttttt                             99

<210> SEQ ID NO 429
<211> LENGTH: 99
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 429
nnnnnnnnnn nnnnnnccng gttggagcta gaaatagcaa gtcaacctaa ggctagtccg      60
ttatcaactt gaaaaagtgg caccgagtcg gtgcttttt                             99

<210> SEQ ID NO 430
<211> LENGTH: 99
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(17)
<223> OTHER INFORMATION: n is a, c, g, or t

<400> SEQUENCE: 430
nnnnnnnnnn nnnnnnncta gttggagcta gaaatagcaa gtcaacctaa ggctagtccg      60
ttatcaactt gaaaaagtgg caccgagtcg gtgcttttt                             99

<210> SEQ ID NO 431
<211> LENGTH: 101
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(20)
<223> OTHER INFORMATION: n is a, c, g, or t

<400> SEQUENCE: 431
nnnnnnnnnn nnnnnnnnnn gtcggagagc tagaaatagc aagttccgat aaggctagtc      60
cgttatcaac ttgaaaaagt ggcaccgagt cggtgctttt t                         101
```

<210> SEQ ID NO 432
<211> LENGTH: 100
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(19)
<223> OTHER INFORMATION: n is a, c, g, or t

<400> SEQUENCE: 432
nnnnnnnnnn nnnnnnnnng gtcggaagct agaaatagca agtccgacta aggctagtcc    60
gttatcaact tgaaaaagtg gcaccgagtc ggtgcttttt                         100

<210> SEQ ID NO 433
<211> LENGTH: 99
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(18)
<223> OTHER INFORMATION: n is a, c, g, or t

<400> SEQUENCE: 433
nnnnnnnnnn nnnnnnnngt gtcggagcta gaaatagcaa gtcgacataa ggctagtccg    60
ttatcaactt gaaaaagtgg caccgagtcg gtgcttttt                           99

<210> SEQ ID NO 434
<211> LENGTH: 99
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(17)
<223> OTHER INFORMATION: n is a, c, g, or t

<400> SEQUENCE: 434
nnnnnnnnnn nnnnnnnccg gtcggagcta gaaatagcaa gtcgacctaa ggctagtccg    60
ttatcaactt gaaaaagtgg caccgagtcg gtgcttttt                           99

<210> SEQ ID NO 435
<211> LENGTH: 99
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 435
nnnnnnnnnn nnnnnnccng gtcggagcta gaaatagcaa gtcgacctaa ggctagtccg        60
ttatcaactt gaaaaagtgg caccgagtcg gtgcttttt                              99

<210> SEQ ID NO 436
<211> LENGTH: 99
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(17)
<223> OTHER INFORMATION: n is a, c, g, or t

<400> SEQUENCE: 436
nnnnnnnnnn nnnnnnncta gtcggagcta gaaatagcaa gtcgacctaa ggctagtccg        60
ttatcaactt gaaaaagtgg caccgagtcg gtgcttttt                              99

<210> SEQ ID NO 437
<211> LENGTH: 101
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(20)
<223> OTHER INFORMATION: n is a, c, g, or t

<400> SEQUENCE: 437
nnnnnnnnnn nnnnnnnnnn ctcggcgagc tagaaatagc aagtgccgat aaggctagtc        60
cgttatcaac ttgaaaaagt ggcaccgagt cggtgctttt t                          101

<210> SEQ ID NO 438
<211> LENGTH: 100
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(19)
<223> OTHER INFORMATION: n is a, c, g, or t

<400> SEQUENCE: 438
nnnnnnnnnn nnnnnnnnng ctcggcagct agaaatagca agtccgagta aggctagtcc        60
gttatcaact tgaaaagtg gcaccgagtc ggtgcttttt                             100

<210> SEQ ID NO 439
<211> LENGTH: 99
<212> TYPE: DNA
<213> ORGANISM: Artificial Sequence
<220> FEATURE:
<223> OTHER INFORMATION: polynucleotides encoding for an sgRNA or crRNA
      recognized by a CRIPSR Cas9 protein and having non-palindromic
      recognition site
<220> FEATURE:
<221> NAME/KEY: misc_feature
<222> LOCATION: (1)..(18)
<223> OTHER INFORMATION: n is a, c, g, or t

<400> SEQUENCE: 439

```
nnnnnnnnnn nnnnnnnngt ctcggcgcta gaaatagcaa gtcgagataa ggctagtccg    60
ttatcaactt gaaaaagtgg caccgagtcg gtgcttttt                           99
```

<210> SEQ ID NO 440
<211> LENGTH: 39
<212> TYPE: RNA
<213> ORGANISM: Artificial Sequence
<220> FEATURE:
<223> OTHER INFORMATION: Francisella novicida
<220> FEATURE:
<221> NAME/KEY: misc_feature
<222> LOCATION: (20)..(39)
<223> OTHER INFORMATION: n is a, c, g, or u

<400> SEQUENCE: 440

```
aauucuacu guuguagaun nnnnnnnnnn nnnnnnnn                             39
```

<210> SEQ ID NO 441
<211> LENGTH: 38
<212> TYPE: DNA
<213> ORGANISM: Artificial Sequence
<220> FEATURE:
<223> OTHER INFORMATION: Francisella novicida cRNA for CRISPR Cpf1
<220> FEATURE:
<221> NAME/KEY: misc_feature
<222> LOCATION: (20)..(38)
<223> OTHER INFORMATION: n is a, c, g, or t

<400> SEQUENCE: 441

```

<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (20)..(38)
<223> OTHER INFORMATION: n is a, c, g, or t

<400> SEQUENCE: 444
aattgttggt gttccgactn nnnnnnnnn nnnnnnn                              38

<210> SEQ ID NO 445
<211> LENGTH: 37
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (20)..(37)
<223> OTHER INFORMATION: n is a, c, g, or t

<400> SEQUENCE: 445
aatttgttgt gtccgacatn nnnnnnnnn nnnnnnn                              37

<210> SEQ ID NO 446
<211> LENGTH: 38
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (20)..(38)
<223> OTHER INFORMATION: n is a, c, g, or t

<400> SEQUENCE: 446
aattctcggt gtgccgagtn nnnnnnnnn nnnnnnn                              38

<210> SEQ ID NO 447
<211> LENGTH: 37
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (20)..(37)
<223> OTHER INFORMATION: n is a, c, g, or t

<400> SEQUENCE: 447
aatttctcgt ggccgagatn nnnnnnnnn nnnnnnn                              37

<210> SEQ ID NO 448
<211> LENGTH: 38
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (22)..(38)
<223> OTHER INFORMATION: n is a, c, g, or t

<400> SEQUENCE: 448
aattgttggt gttccaacta tnnnnnnnnn nnnnnnn                              38

<210> SEQ ID NO 449
<211> LENGTH: 37
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (22)..(37)
<223> OTHER INFORMATION: n is a, c, g, or t

<400> SEQUENCE: 449
aatttgttgt gtccaacata tnnnnnnnnn nnnnnnn                              37

<210> SEQ ID NO 450
<211> LENGTH: 38
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (22)..(38)
<223> OTHER INFORMATION: n is a, c, g, or t

<400> SEQUENCE: 450
aattgttggt gttccgacta tnnnnnnnnn nnnnnnn                              38

<210> SEQ ID NO 451
<211> LENGTH: 37
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (22)..(37)
<223> OTHER INFORMATION: n is a, c, g, or t

<400> SEQUENCE: 451
aatttgttgt gtccgacata tnnnnnnnnn nnnnnnn                              37

<210> SEQ ID NO 452
<211> LENGTH: 38
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (22)..(38)
<223> OTHER INFORMATION: n is a, c, g, or t

<400> SEQUENCE: 452
aattctcggt gtgccgagta tnnnnnnnnn nnnnnnn                              38

```
<210> SEQ ID NO 453
<211> LENGTH: 37
<212> TYPE: DNA
<213> ORGANISM: Artificial Sequence
<220> FEATURE:
<223> OTHER INFORMATION: polynucleotides encoding for an sgRNA or crRNA
      recognized by a CRISPR Cpf1 protein and having non-palindromic
      recognition site.
<220> FEATURE:
<221> NAME/KEY: misc_feature
<222> LOCATION: (22)..(37)
<223> OTHER INFORMATION: n is a, c, g, or t

<400> SEQUENCE: 453
aatttctcgt ggccgagata tnnnnnnnnn nnnnnnn                                37
```